(12) United States Patent
Moon

(10) Patent No.: US 11,937,936 B2
(45) Date of Patent: Mar. 26, 2024

(54) THYROID FUNCTION MONITORING METHOD ACCORDING TO MEDICATION, AND MONITORING SERVER AND USER TERMINAL PERFORMING THE SAME

(71) Applicant: THYROSCOPE INC., Ulsan (KR)

(72) Inventor: Jae Hoon Moon, Seoul (KR)

(73) Assignee: THYROSCOPE INC., Ulsan (KR)

( * ) Notice: Subject to any disclaimer, the term of this patent is extended or adjusted under 35 U.S.C. 154(b) by 0 days.

(21) Appl. No.: 17/514,952

(22) Filed: Oct. 29, 2021

(65) Prior Publication Data
US 2022/0104752 A1 Apr. 7, 2022

Related U.S. Application Data

(63) Continuation of application No. PCT/KR2021/002707, filed on Mar. 4, 2021.

(30) Foreign Application Priority Data

Jun. 10, 2020 (KR) .................. 10-2020-0069999

(51) Int. Cl.
*A61B 5/00* (2006.01)
*A61B 5/024* (2006.01)
(Continued)

(52) U.S. Cl.
CPC .......... *A61B 5/4227* (2013.01); *A61B 5/0002* (2013.01); *A61B 5/02405* (2013.01);
(Continued)

(58) Field of Classification Search
CPC ........ G16H 50/30; G16H 50/20; G16H 40/67; G16H 70/40; A61B 5/7275; A61B 5/7264;
(Continued)

(56) References Cited

U.S. PATENT DOCUMENTS

2017/0068790 A1* 3/2017 Fuerst .................... G16H 50/30
2017/0235912 A1* 8/2017 Moturu .................. G16H 40/67
705/2

(Continued)

FOREIGN PATENT DOCUMENTS

JP 2005-523426 A 8/2005
JP 2006-501534 A 1/2006
(Continued)

OTHER PUBLICATIONS

English translation of WO2019054553, obtained Mar. 30, 2022 (Year: 2019).*

(Continued)

*Primary Examiner* — Yi-Shan Yang
*Assistant Examiner* — Kyle W. Kretzer
(74) *Attorney, Agent, or Firm* — K&L Gates LLP

(57) ABSTRACT

According to an embodiment of the present application, as a method of determining whether to output an alert of a user's thyroid dysfunction, there may be provided a thyroid dysfunction monitoring method including receiving a user's medication information from an external device; selecting a monitoring algorithm to be used to determine whether to output the alert on the basis of the medication information; and determining whether to output the alert on the basis of the selected monitoring algorithm.

14 Claims, 43 Drawing Sheets

(51) Int. Cl.
*A61B 5/0531* (2021.01)
*G16H 40/67* (2018.01)
*G16H 70/40* (2018.01)

(52) U.S. Cl.
CPC .......... *A61B 5/0531* (2013.01); *A61B 5/4848* (2013.01); *A61B 5/7465* (2013.01); *G16H 40/67* (2018.01); *G16H 70/40* (2018.01)

(58) Field of Classification Search
CPC . A61B 5/4227; A61B 5/0002; A61B 5/02405; A61B 5/7465; A61B 5/0531; A61B 5/4848; A61B 5/02438; A61B 5/681; A61B 5/746
See application file for complete search history.

(56) References Cited

U.S. PATENT DOCUMENTS

2018/0365385 A1* 12/2018 Cooney ............... G16H 20/60
2020/0305713 A1* 10/2020 Sipe ................... G16H 40/67

FOREIGN PATENT DOCUMENTS

| JP | 2016-146622 A | 8/2016 | |
| JP | 6058585 B2 | 1/2017 | |
| KR | 10-2017-0017648 A | 2/2017 | |
| KR | 10-2017-0061263 A | 6/2017 | |
| KR | 10-2019-0032668 A | 3/2019 | |
| KR | 10-2019-0059422 A | 5/2019 | |
| WO | WO-2019054553 A1 * | 3/2019 | ............... A61B 5/00 |

OTHER PUBLICATIONS

Meghan Holohan, "It saved my life: How a smartwatch stopped a woman's health crisis", Apr. 12, 2018, Today (Year: 2018).*
Aaron B. Neinstein, Michael Blum, and Umesh Masharani. Clinical Thyroidology. May 2020.242-244.http://doi.org/10.1089/ct.2020;32. 242-244 (Year: 2020).*
English Machine Translation of WO-2019054553-A1, 17 pages. (Year: 2019).*
Udovcic M, Pena RH, Patham B, Tabatabai L, Kansara A. Hypothyroidism and the Heart. Methodist Debakey Cardiovasc J. Apr.-Jun. 2017;13(2):55-59. doi: 10.14797/mdcj-13-2-55. PMID: 28740582; PMCID: PMC5512679. (Year: 2017).*
International Search Report from corresponding International Patent Application No. PCT/KR2021/002707, dated Jul. 1, 2021.
Written Opinion from corresponding International Patent Application No. PCT/KR2021/002707, dated Jul. 1, 2021.
Office Action in Korean Patent Application No. 10-2020-0128685 dated Jun. 23, 2022.
Notice of Allowance dated Mar. 23, 2023 in Korean Patent Application No. 10-2020-0128685.
Decision of Refusal dated Mar. 24, 2023 in Japanese Patent Application No. 2021-576255.

* cited by examiner

Table 1. Baseline characteristics before total thyroidectomy

| Characteristics | Hypothyroidism (n = 30) | Control (n = 14) | P value |
|---|---|---|---|
| Age (years) | 38.1 ± 8.4 | 42.4 ± 7.4 | 0.112[a] |
| Gender, n (%) | | | |
| Male | 15 (50.0) | 2 (14.3) | 0.044[b] |
| Female | 15 (50.0) | 14 (85.7) | |
| Body mass index (kg/m2) | 25.2 ± 4.6 | 23.2 ± 4.8 | 0.204[a] |
| Systolic blood pressure | 127.4 ± 12.5 | 122.7 ± 9.4 | 0.221[a] |
| Diastolic blood pressure | 77.9 ± 10.2 | 72.8 ± 10.2 | 0.130[a] |
| On-site resting heart rate (bpm) | 74.0 ± 9.5 | 73.4 ± 9.9 | 0.850[a] |
| Thyroid function test | | | |
| Free T4 (ng/dL) | 1.32 ± 0.24 | 1.37 ± 0.14 | 0.470[a] |
| TSH (mIU/L) | 1.91 (1.27) | 1.44 (0.95) | 0.332[c] |
| Glucose (mg/dL) | 97.9 ± 22.9 | 93.7 ± 7.2 | 0.514[a] |
| BUN (mg/dL) | 14.5 ± 10.8 | 12.1 ± 3.9 | 0.434[a] |
| Creatinine (mg/dL) | 0.74 ± 0.18 | 0.64 ± 0.09 | 0.049[a] |
| Total cholesterol (mg/dL) | 181.3 ± 32.3 | 172.1 ± 32.9 | 0.389[a] |
| Total protein (g/dL) | 7.3 ± 0.4 | 7.4 ± 0.6 | 0.637[a] |
| Albumin (g/dL) | 4.4 ± 0.3 | 4.3 ± 0.4 | 0.885[a] |
| AST (mg/dL) | 23.5 ± 8.1 | 23.4 ± 4.6 | 0.940[a] |
| ALT (mg/dL) | 24.9 ± 16.7 | 22.9 ± 9.9 | 0.685[a] |
| WBC (no/mm3) | 6838 ± 1966 | 5049 ± 2384 | 0.023[a] |
| Hemoglobin (mg/dL) | 13.8 ± 1.8 | 13.2 ± 1.0 | 0.190[a] |
| Platelet (no/mm3) | 283 ± 56 | 281 ± 61 | 0.913[a] |

Data are expressed as mean ± SD or median (interquartile range).
bpm, beats per minute; T4, thyroxine; TSH, thyroid stimulating hormone;
BUN, blood urea nitrogen; AST, aspartate aminotransferase;
ALT, alanine aminotransferase; WBC, white blood cell

[a]Derived from Student t test.
[b]Derived from Fisher exacr probability test.
[c]Derived from Mann Whitney U test.

FIG. 13

Table 2. Change of thyroid function and associating parameters during the study period

| Thyroid function test results and associated parameters | Visit 1 or 3[a] | Visit 2 (RAI Tx) | P value |
|---|---|---|---|
| Hypothyroidism group | | | |
| Free T4 (ng/dL) | 1.74 ± 0.23 | 0.08 ± 0.06 | <0.001[b] |
| TSH (mIU/L) | 0.19 (0.87) | 84.40 (46.74) | <0.001[c] |
| Zulewski's clinical score | 1 (2) | 1 (2) | 0.089[c] |
| On-site rHR (bpm) | 84.9 ± 10.4 | 73.0 ± 10.9 | <0.001[b] |
| WD-rHR (bpm) | 68.5 ± 8.3 | 60.2 ± 6.4 | <0.001[b] |
| WD-sleepHR (bpm) | 63.0 ± 9.0 | 55.3 ± 6.1 | <0.001[b] |
| WD-2to6HR (bpm) | 64.5 ± 8.2 | 56.7 ± 6.7 | <0.001[b] |
| Control group | | | |
| Free T4 (ng/dL) | 1.68 ± 0.19 | 1.56 ± 0.18 | 0.021[b] |
| TSH (mIU/L) | 0.22 (0.44) | 157.63 (50.61) | 0.332[c] |
| Zulewski's clinical score | 2 (2) | 2 (1) | 0.926[c] |
| On-site rHR (bpm) | 83.0 ± 14.5 | 79.5 ± 12.5 | 0.262[b] |
| WD-rHR (bpm) | 67.1 ± 7.0 | 64.5 ± 6.2 | 0.026[b] |
| WD-sleepHR (bpm) | 63.5 ± 6.2 | 61.0 ± 6.4 | 0.010[b] |
| WD-2to6HR (bpm) | 63.6 ± 6.0 | 61.2 ± 7.0 | 0.027[b] |

Data are expressed as mean ± SD or median (interquartile range).
RAI Tx, radioactive iodine therapy; T4, thyroxine; TSH, thyroid stimulating hormone; rHR, resting heart rate; bpm, beats per minute; WD-rHR, rHR from wearable device; WD-sleepHR, HR during sleep from wearable device; WD-2to6HR, HR during 2am to 6am from wearable device

[a] In case of missing data at visit 2, data at visit 3 were included in the analyses
[b] Derived from paired $t$ test
[c] Derived from Wilcoxon signed-rank test

FIG. 14

Table 3. Linear model generalized equation analyses for association between free T4 and HR parameters

| HR parameters | Unstandardized beta | 95% CI | P value |
|---|---|---|---|
| On-site rHR (bpm) | 0.015 | 0.009 to 0.021 | <0.001 |
| WD-rHR (bpm) | 0.041 | 0.026 to 0.056 | <0.001 |
| WD-sleepHR (bpm) | 0.047 | 0.030 to 0.063 | <0.001 |
| WD-2to6HR (bpm) | 0.042 | 0.025 to 0.059 | <0.001 |

T4, thyroxine; HR, heart rate; CI, confidence interval; rHR, resting HR;
WD-rHR, rHR from wearable device; WD-sleepHR, HR during sleep from
wearable device; WD-2to6HR, HR during 2am to 6am from wearable device

FIG. 15

Table 4. Binary logistic model generalized equation analyses for association between hypothyroidism and HR parameters

| HR parameters | Odds ratio | 95% CI | P value |
|---|---|---|---|
| On-site rHR (bpm) | 1.039 | 1.008 to 1.071 | 0.015 |
| WD-rHR (bpm) | 1.171 | 1.075 to 1.275 | <0.001 |
| WD-sleepHR (bpm) | 1.178 | 1.083 to 1.283 | <0.001 |
| WD-2to6HR (bpm) | 1.165 | 1.069 to 1.270 | 0.001 |

T4, thyroxine; HR, heart rate; CI, confidence interval; rHR, resting HR; WD-rHR, rHR from wearable device; WD-sleepHR, HR during sleep from wearable device; WD-2to6HR, HR during 2am to 6am from wearable device

[a]Parameters were multiplied by -1 to see the odd ratio of hypothyroidism when the parameters decrease were included in the analyses

THYROID FUNCTION MONITORING METHOD ACCORDING TO MEDICATION, AND MONITORING SERVER AND USER TERMINAL PERFORMING THE SAME

TECHNICAL FIELD

An embodiment relates to a thyroid function monitoring method according to medication.

An embodiment relates to a monitoring server for performing thyroid function monitoring according to medication.

An embodiment relates to a user terminal for performing thyroid function monitoring according to medication.

An embodiment relates to a thyroid function monitoring method based on skin conductance data.

BACKGROUND ART

According to one statistic, 12 percent of the US population will experience thyroid dysfunction during their lifetime, and it is known that about 20 million Americans suffer from diseases caused by thyroid dysfunction. Thyroid dysfunction is a disease that requires attention and continuous monitoring as it causes inconvenience and complications in life for many people in the United States and worldwide.

However, in the past, patients had to visit a hospital and perform blood tests to monitor thyroid dysfunction, so tests were often delayed according to hospital appointments, which made systematic monitoring impossible. Also, since visiting a hospital for medical treatment was actually a loss of time for patients, there were a significant number of patients who did not perform the tests until symptoms due to thyroid dysfunction appeared.

The lack of monitoring for thyroid dysfunction has caused several negative phenomena, such as worsened symptoms in patients and increased burden of treatment costs. Accordingly, there has been a need to provide a thyroid function monitoring method that is continuous and that can be easily used by patients.

Also, in the case of patients with thyroid dysfunction, most are undergoing therapy with medication, but they have concerns about the appropriateness of the amount of medication and about whether side effects are currently occurring in their bodies. Accordingly, there is a need to develop a thyroid function monitoring method that can be provided to patients who take medicine.

DISCLOSURE

Technical Problem

An embodiment provides a monitoring method for detecting the occurrence of thyroid dysfunction as a side effect for patients taking medicine.

An embodiment provides a monitoring method for preventing patients from taking an overdose of medication and inducing patients to visit hospitals.

An embodiment provides a method of predicting a user's thyroid dysfunction on the basis of skin conductance data acquired through a wearable device.

Technical Solution

According to an embodiment of the present application, a method for determining whether to output an alert of a user's thyroid abnormality, the method comprising: receiving the user's drug taking information from an external device, wherein the drug taking information includes at least one of a prescription date, name, type, dose or dosing cycle of the drug related to thyroid function; selecting a monitoring algorithm being used for determining whether to output the alert based on the drug taking information, wherein the monitoring algorithm is a first monitoring algorithm or a second monitoring algorithm, wherein the second monitoring algorithm is different from the first monitoring algorithm; and determining whether to output the alert based on the selected monitoring algorithm; wherein the determining whether to output the alert comprises: if the selected monitoring algorithm is the first monitoring algorithm, determining to output the alert when a monitoring heart rate is greater than a reference heart rate by a first threshold or more; and if the selected monitoring algorithm is the second monitoring algorithm, determining to output the alert when the monitoring heart rate is smaller than the reference heart rate by a second threshold or more, wherein the reference heart rate is calculated based on the thyroid hormone level of the user and the heart rate of the user, or is calculated based on the heart rate of the user for a plurality of consecutive days, wherein the monitoring heart rate is calculated based on the heart rate of the user in a resting period, wherein the resting period is selected based on information about state of movement of the user.

Advantageous Effects

According to an embodiment, in order to ensure that patients who are concerned about side effects due to medication can continue to receive treatment in a stable state, there is provided a monitoring method for monitoring thyroid dysfunction that may occur as a side effect of the medication for the patients.

According to an embodiment, by monitoring whether patients continue to take prescribed medicine along with prolonged medication even though the patients have already been treated, there is provided a monitoring method for preventing patients from overdosing of their medicine and inducing patients to visit a hospital.

According to an embodiment, there is provided a method of defining a resting period in skin conductance data acquired through a wearable device and predicting a user's thyroid dysfunction on the basis of the skin conductance data in the resting period.

Advantageous effects of the present application are not limited to the aforementioned effects, and other advantageous effects that are not described herein will be clearly understood by those skilled in the art from the following description and the accompanying drawings.

DESCRIPTION OF DRAWINGS

FIG. 12 is a diagram showing characteristics of each clinical group for clinical subjects participating in a clinical study process.

FIG. 13 is a diagram showing changes in thyroid function parameters between a first hospital visit and a second hospital visit for clinical subjects participating in a clinical study process.

FIG. 14 is a diagram showing a result of analyzing the association between a free T4 thyroid hormone concentration and a heart rate parameter on the basis of the changes in thyroid function parameters shown in FIG. 13.

FIG. 15 is a diagram showing a result of analyzing the associations between hypothyroidism and heart rate parameters on the basis of the changes in thyroid function parameters shown in FIG. 13.

MODE(S) FOR CARRYING OUT THE INVENTION

Figure 1:
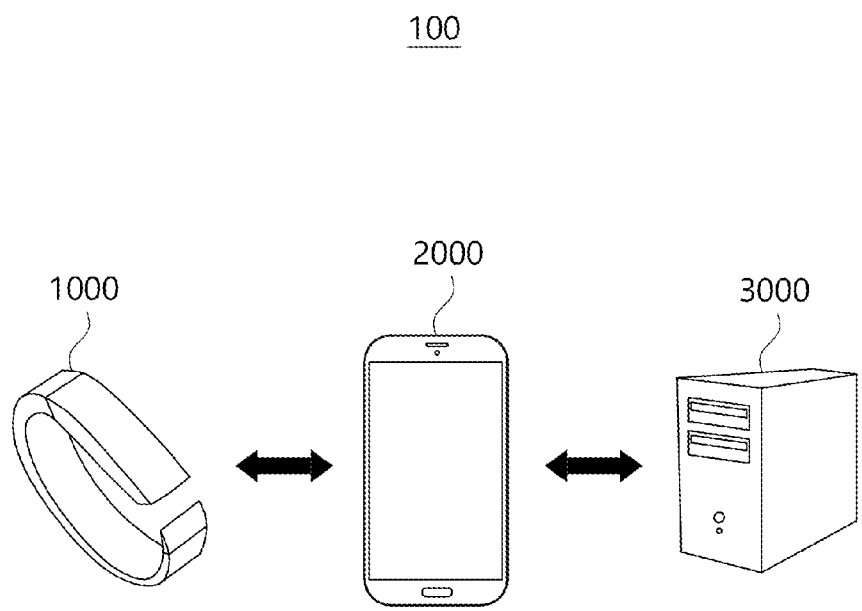
FIG. 1 is a schematic diagram of a thyroid function monitoring system according to an embodiment of the present application.

The above objects, features, and advantages of the present disclosure will become more apparent from the following detailed description taken in conjunction with the accompanying drawings. However, since the present disclosure may be variously modified and have several exemplary embodiments, specific exemplary embodiments will be shown in the accompanying drawings and described in detail.

In the drawings, the thickness of layers and regions is exaggerated for clarity. Also, when it is mentioned that an element or layer is "on" another element or layer, the element or layer may be formed directly on another element or layer, or a third element or layer may be interposed therebetween. Like reference numerals refer to like elements throughout the specification. Further, like reference numerals will be used to designate like elements within the same scope shown in the drawings of the embodiments.

Detailed descriptions about well-known functions or configurations associated with the present application will be omitted in order not to unnecessarily obscure the subject matter of the present application. Also, ordinal numbers (e.g., first, second, etc.) used in the following description are merely identification symbols for distinguishing one element from another element.

The suffixes "module" and "unit" for elements used in the following description are given or used interchangeably only for the ease of writing this specification, and thus do not themselves have distinct meanings or roles.

According to an embodiment of the present application, a method for determining whether to output an alert of a user's thyroid abnormality, the method comprising: receiving the user's drug taking information from an external device, wherein the drug taking information includes at least one of a prescription date, name, type, dose or dosing cycle of the drug related to thyroid function; selecting a monitoring algorithm being used for determining whether to output the alert based on the drug taking information, wherein the monitoring algorithm is a first monitoring algorithm or a second monitoring algorithm, wherein the second monitoring algorithm is different from the first monitoring algorithm; and determining whether to output the alert based on the selected monitoring algorithm; wherein the determining whether to output the alert comprises: if the selected monitoring algorithm is the first monitoring algorithm, determining to output the alert when a monitoring heart rate is greater than a reference heart rate by a first threshold or more; and if the selected monitoring algorithm is the second monitoring algorithm, determining to output the alert when the monitoring heart rate is smaller than the reference heart rate by a second threshold or more, wherein the reference heart rate is calculated based on the thyroid hormone level of the user and the heart rate of the user, or is calculated based on the heart rate of the user for a plurality of consecutive days, wherein the monitoring heart rate is calculated based on the heart rate of the user in a resting period, wherein the resting period is selected based on information about state of movement of the user.

According to a method for determining whether to output an alert of a user's thyroid abnormality, wherein selecting the monitoring algorithm comprises: classifying the user into a hyperthyroidism treatment group or a hypothyroidism treatment group based on the drug taking information.

According to a method for determining whether to output an alert of a user's thyroid abnormality, wherein selecting the monitoring algorithm comprises: selecting the first monitoring algorithm if the user is classified as a hypothyroidism treatment group.

According to a method for determining whether to output an alert of a user's thyroid abnormality, wherein selecting the monitoring algorithm comprises: selecting the second monitoring algorithm if the user is classified as a hyperthyroidism treatment group.

According to a method for determining whether to output an alert of a user's thyroid abnormality, wherein determining whether to output the alert comprises: if the selected monitoring algorithm is the first monitoring algorithm, determining whether a predetermined period has elapsed based on the prescription date when the monitoring heart rate is lower than the reference heart rate by a second threshold or more; and determining to output the alert when the predetermined period has elapsed.

According to a method for determining whether to output an alert of a user's thyroid abnormality, wherein determining whether to output the alert comprises: if the selected monitoring algorithm is the second monitoring algorithm, determining whether a predetermined period has elapsed based on the prescription date when the monitoring heart rate is greater than the reference heart rate by a first threshold or more; and determining to output of the alert when the predetermined period has elapsed.

According to a method for determining whether to output an alert of a user's thyroid abnormality, the method further comprises: before receiving the user's drug taking information from an external device, determining to output the alert when the monitoring heart rate is greater than the reference heart rate by a first threshold or more; and determining to output the alert when the monitoring heart rate is smaller than the reference heart rate by a second threshold or more.

According to a method for determining whether to output an alert of a user's thyroid abnormality, wherein the resting period is determined based on a period lasting more than a predetermined time in a state where the number of steps of the user is 0, or is determined based on a period lasting more than a predetermined time in a state where the user's acceleration is 0.

According to a method for determining whether to output an alert of a user's thyroid abnormality, the method further comprises calculating the reference heart rate, wherein calculating the reference heart rate comprises: confirming, when the thyroid hormone level is received, the received thyroid hormone level is within a normal range; and computing, when the thyroid hormone level is in the normal range, the reference heart rate based on the resting heart rate of a plurality of consecutive days including a test day of the thyroid hormone level.

According to a method for determining whether to output an alert of a user's thyroid abnormality, wherein the calculating the reference heart rate comprises: if the thyroid hormone level is not in the normal range, calculating the current heart rate based on the resting heart rate of a plurality of consecutive days including the test day of the thyroid hormone level; and estimating the reference heart rate, when the thyroid function of the user is normal, based on the thyroid hormone level and the calculated current heart rate.

According to a method for determining whether to output an alert of a user's thyroid abnormality, wherein selecting the monitoring algorithm is performed whenever the drug taking information is received, wherein determining whether to output the alert is performed every day after selecting the monitoring algorithm is performed, and wherein determining whether to output the alert is performed more than a number of times the monitoring algorithm is performed.

According to a method for determining whether to output an alert of a user's thyroid abnormality, the method further comprises determining to output a drug taking notification based on the dosing cycle of the drug, wherein determining to output the drug taking notification is performed more than the number of times the determining whether to output the alert.

According to a method for determining whether to output an alert of a user's thyroid abnormality, the method further comprises receiving heart rate information of the user at every second period from the external device that measures the heart rate of the user at every first period, wherein the second period is longer than the first period.

According to a method for determining whether to output an alert of a user's thyroid abnormality, the method further comprises transmitting a signal to the external device for outputting the alert on a display unit of the external device, when the alert is determined to be output.

A non-statutory recording medium storing an executable code read by a computer on which a program is recorded for performing the method of any one of claims 1 to 14.

According to a monitoring server comprising: a communication unit configured to receive biometric information obtained from a user of a wearable device from an external device; and a control unit is configured to select a monitoring algorithm based on the user's drug taking information received from the communication unit, determine whether to output an alert based on the selected monitoring algorithm, and transmit a signal through the communication unit when the alert is determined to be output; and wherein the drug taking information includes at least one of a prescription date, name, type, dose or dosing cycle of the drug related to thyroid function, wherein the monitoring algorithm is a first monitoring algorithm or a second monitoring algorithm, wherein the first monitoring algorithm is an algorithm that determines the output of the alert when a monitoring heart rate is greater than a reference heart rate by a first threshold or more, wherein the second monitoring algorithm is an algorithm that determines the output of the alert when the monitoring heart rate is smaller than the reference heart rate by a second threshold or more, wherein the reference heart rate is calculated based on the thyroid hormone level of the user and the heart rate of the user, or is calculated based on the heart rate of the user for a plurality of consecutive days, wherein the monitoring heart rate is calculated based on the heart rate of the user in a resting period, and wherein the resting period is selected based on information about state of movement of the user.

According to a user terminal comprising: a communication unit configured to receive biometric information obtained from a user of a wearable device from an external device; an input unit configured to receive the user's drug taking information, wherein the drug taking information includes at least one of a prescription date, name, type, dose or dosing cycle of the drug related to thyroid function; a control unit is configured to select a monitoring algorithm based on the drug taking information, determine whether to output an alert based on the selected monitoring algorithm, and control to output the alert of the user's thyroid abnormality through an output unit when the alert is determined to be output, wherein the monitoring algorithm is a first monitoring algorithm or a second monitoring algorithm, wherein the first monitoring algorithm is an algorithm that determines the output of the alert when a monitoring heart rate is greater than a reference heart rate by a first threshold or more, wherein the second monitoring algorithm is an algorithm that determines the output of the alert when the monitoring heart rate is smaller than the reference heart rate by a second threshold or more, wherein the reference heart rate is calculated based on the thyroid hormone level of the user and the heart rate of the user, or is calculated based on the heart rate of the user for a plurality of consecutive days, wherein the monitoring heart rate is calculated based on the heart rate of the user in a resting period, and wherein the resting period is selected based on information about state of movement of the user.

According to an embodiment of the present application, as a method of predicting a user's thyroid dysfunction using a wearable device worn on the user's body part, there may be provided a thyroid dysfunction prediction method including acquiring the user's skin conductance data through the wearable device for measuring the user's skin conductance, extracting, based on the skin conductance data, a resting period in which the skin conductance data changes within a threshold range for a predetermined period, and comparing reference skin conductance and monitoring skin conductance to predict the user's thyroid dysfunction, and the resting period is a period that starts after a decreasing period in which the skin conductance data decreases beyond the size of the threshold range, the reference skin conductance is calculated based on the skin conductance data in the resting period for a reference period, the monitoring skin conductance is calculated based on the skin conductance data in the resting period for a monitoring period, which is a period for determining whether the user's thyroid function is abnormal, and the reference period and the monitoring period do not overlap each other.

Here, the monitoring period may include at least one day.

Here, an interval at which the wearable device measures the skin conductance may be shorter than the predetermined period.

Here, the size of the threshold range may be less than or equal to 2 μS.

Here, the thyroid dysfunction prediction method may include transmitting a message to the wearable device on the basis of a result of the prediction operation. The message may include a first alert when the monitoring skin conductance is greater than the reference skin conductance by a first value and a second alert when the monitoring skin conductance is smaller than the reference skin conductance by a second value, the first alert may include information related to hyperthyroidism, and the second alert may include information related to hypothyroidism.

Here, the first value and the second value may be different from each other.

Here, when the number of times the first alert or the second alert is output for a predetermined period exceeds a predetermined number, the message may include a comment proposing to seek an expert's opinion.

Here, the monitoring period may be based on the user's sleep period.

Here, the monitoring period may include a plurality of rapid eye movement (REM) sleep periods of the user.

Here, the monitoring skin conductance may be obtained based on at least one resting period.

Here, the reference skin conductance may be obtained based on at least one resting period when the user's thyroid function is normal.

Here, the message may include a questionnaire for self-diagnosis.

Here, the skin conductance data during the resting period may be less than or equal to a predetermined value.

Here, the average of the skin conductance data before the decreasing period may be greater than the average of the skin conductance data after the decreasing period.

Here, the change frequency of the skin conductance data before the decreasing period may be greater than the change frequency of the skin conductance data after the decreasing period, and the change frequency may be based on a derivative of the skin conductance data.

Here, the change frequency of the skin conductance before the decreasing period may be greater than the change frequency of the skin conductance during the decreasing period, and the change frequency may be based on a derivative of the skin conductance data.

Here, the change frequency of the skin conductance data during a wearing period is greater than the change frequency of the skin conductance data during the resting period, the wearing period may be a predetermined period after the user wears the wearable device, and the change frequency may be based on a derivative of the skin conductance data.

Here, a difference in the skin conductance between before and after the wearing period may be greater than a difference between the skin conductance between before and after the resting period, and the wearing period may be a predetermined period after the user wears the wearable device.

Here, a first time point included in the reference period may be earlier than a second time point included in the monitoring period.

There may be provided a recording medium in which a program is recorded to perform the method of any one of the preceding claims and in which a code that is readable and executable by a computer is stored.

A thyroid function monitoring system 100 according to an embodiment of the present application will be described below.

The thyroid function monitoring system 100 is a system for detecting a user's bio-signal through a wearable device 1000 and predicting the user's thyroid function of the wearable device 1000 on the basis of the detected bio-signal.

<Thyroid Function Monitoring System 100>

FIG. 1 is a schematic diagram of a thyroid function monitoring system 100 according to an embodiment of the present application.

Referring to FIG. 1, the thyroid function monitoring system 100 may include a wearable device 1000, a user terminal 2000, and a monitoring server 3000.

However, the components shown in FIG. 1 are not essential, and the thyroid function monitoring system 100 may have more components or fewer components.

The wearable device 1000 may be worn on a user's body to detect the user's bio-signal.

The wearable device 1000 may detect a user's biometric information. As an example, the wearable device 1000 may detect a user's heart rate information. As another example, the wearable device 1000 may detect a user's heart rate information and a user's movement information. As another example, the wearable device 1000 may detect a user's heart rate information and a user's temperature information. As another example, the wearable device 1000 may detect a user's skin conductance information. However, the present invention is not limited to examples described herein, and the wearable device 1000 may detect one or more pieces of biometric information corresponding to a user's bio-signal.

The wearable device 1000 may transmit the detected biometric information to a user terminal 2000 and/or a monitoring server 3000. As an example, the wearable device 1000 may transmit the detected biometric information to the user terminal 2000, and the user terminal 2000 may transmit the received biometric information to the monitoring server 3000.

As an example, the wearable device 1000 may transmit the user's heart rate information to the user terminal 2000. As another example, the wearable device 1000 may transmit the user's movement information to the user terminal 2000. As another example, the wearable device 1000 may transmit the user's temperature to the user terminal 2000. As another example, the wearable device 1000 may transmit the user's skin conductance information to the user terminal 2000.

The wearable device 1000 may transmit detected first biometric information to the user terminal 2000 in association with information on an external environment.

As an example, the wearable device 1000 may transmit information on a detected first bio-signal to the user terminal 2000 in association with time information. As a specific example, the wearable device 1000 may transmit the user's heart rate information mapped to time information to the user terminal 2000.

As another example, the wearable device 1000 may transmit the information on the detected first bio-signal to the user terminal 2000 in association with external temperature information. As a specific example, the wearable device 1000 may transmit the user's skin conductance information mapped to external temperature information to the user terminal 2000.

The wearable device 1000 may transmit the detected first biometric information to the user terminal 2000 in association with second biometric information different from the first biometric information.

As an example, the wearable device 1000 may transmit a plurality of kinds of bio-signals (e.g., heart rate information and temperature information) to the user terminal 2000 in the form of a data set linked with time.

The user terminal 2000 may perform an operation determined based on biometric information received from the wearable device 1000.

As an example, when a user's thyroid state information is input through a terminal input unit 2100, the user terminal 2000 may transmit the user's thyroid state information to the monitoring server 3000.

As another example, the user terminal 2000 may transmit received biometric information to the monitoring server 3000 according to a determined condition. As a specific example, when biometric information is received, the user terminal 2000 may transmit the biometric information to the monitoring server 3000. As a specific example, the user terminal 2000 may store the received biometric information and transmit the stored biometric information to the monitoring server 3000 at predetermined intervals.

The monitoring server 3000 may perform thyroid function monitoring on the basis of the received biometric information. The thyroid function monitoring method according to the present application will be described in detail below.

The monitoring server 3000 may transmit result information corresponding to the thyroid function monitoring to the user terminal 2000. The user terminal 2000 may output information corresponding to the result information through a terminal output unit 2200 on the basis of the result information received from the monitoring server 3000.

The monitoring server 3000 may transmit an alert to the user terminal 2000 on the basis of the result of the thyroid function monitoring. The user terminal 2000 may allow an alert about the user's thyroid function through the terminal output unit 2200 on the basis of a signal received from the monitoring server 3000.

So far, the thyroid function monitoring system 100 according to an embodiment of the present application has been schematically described.

FIG. 1 shows a schematic diagram of a system in which the wearable device 1000 and the user terminal 2000 are communicatively connected and in which the user terminal 2000 is communicatively connected to the monitoring server 3000, but the connection relationship between the components may be modified and implemented.

As an example, the thyroid function monitoring system 100 may be implemented such that the connection relationship between the user terminal 2000 and the monitoring server 3000 is switched so that the monitoring server 3000 directly communicates with the wearable device 1000 and the user terminal 2000 receives information having passed through the monitoring server 3000. As another example, the monitoring server 3000 may be implemented in the form of a program installed in the user terminal 2000, and thus the monitoring system 100 may be implemented in which only bilateral communication between the user terminal 2000 and the wearable device 1000 is performed. As still another example, the wearable device 1000 may be implemented to directly communicate with the monitoring server 3000 and output information received from the monitoring server 3000 to a user through the wearable device 1000, and thus the monitoring system 100 may be implemented in which only bilateral communication between the wearable device 1000 and the monitoring server 3000 is performed.

Also, although one user terminal 2000 is shown in FIG. 1, the monitoring server 3000 may be connected to respective user terminals 2000 of a plurality of users. Also, one user can use one user terminal 2000 to use the thyroid function monitoring system 100, one user can use a plurality of user terminals 2000 to use the thyroid function monitoring system 100, and a plurality of users can use one user terminal 2000 to use the thyroid function monitoring system 100.

The components of the thyroid function monitoring system 100 according to an embodiment of the present application will be described in detail below.

<Components of Thyroid Function Monitoring System 100>

1. Wearable Device 1000

Figure 2:
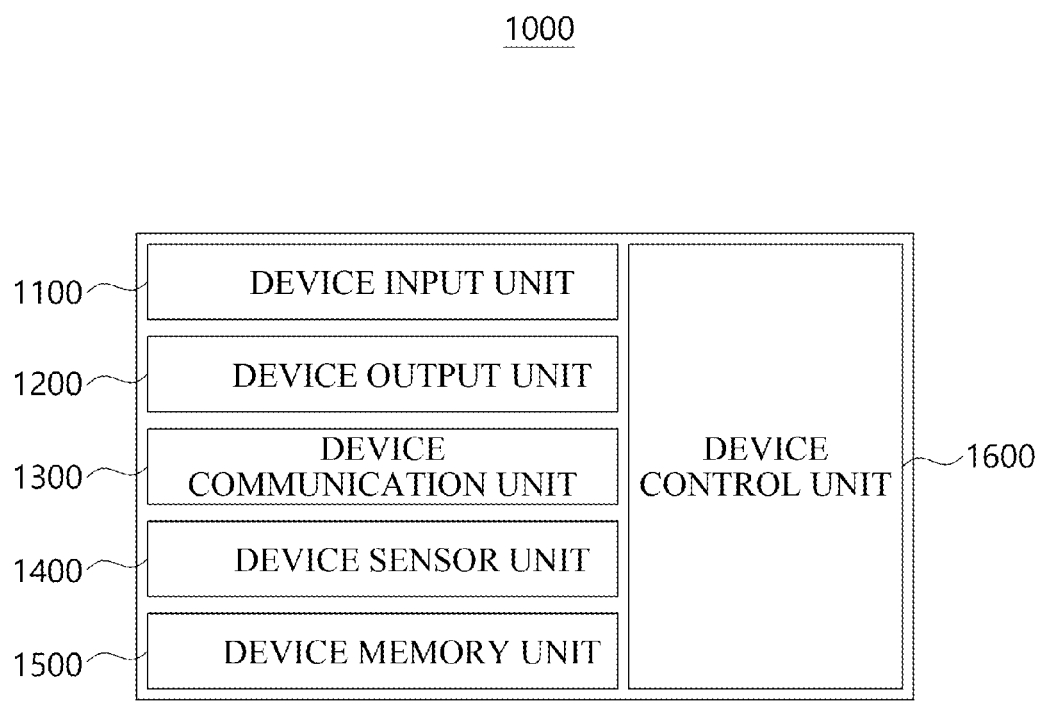
FIG. 2 is a block diagram of a wearable device according to an embodiment of the present application.

FIG. 2 is a block diagram of a wearable device 1000 according to an embodiment of the present application.

Referring to FIG. 2, the wearable device 1000 may include a device input unit 1100, a device output unit 1200, a device communication unit 1300, a device sensor unit 1400, a device memory unit 1500, and a device control unit 1600. However, the components shown in FIG. 2 are not essential, and the wearable device 1000 may have more components or fewer components.

The device input unit 1100 may perform a function of acquiring information from a user. The device input unit 1100 may receive a user input from a user. The user input may be a key input, a touch input, and/or a voice input. However, the present invention is not limited thereto, and the user input may be formed in various forms.

The device input unit 1100 may be implemented as a generally used user input device. As an example, the device input unit 1100 may be implemented as a touch sensor configured to detect a user's touch, a microphone configured to receive a voice signal, a camera configured to recognize a gesture or the like through image recognition, a proximity sensor composed of an illumination sensor or infrared sensor for detecting a user's approach, a motion sensor configured to recognize a user's motion through an acceleration sensor, a gyro sensor or the like, and various input units configured to detect or receive various user inputs in addition to typical keypads, keyboards, and mice.

Here, the term "touch sensor" may refer to a piezoelectric or capacitive touch sensor that senses a touch through a touch panel or a touch film attached to a display panel, an optical touch sensor that senses a touch by an optical method, and the like.

Alternatively, the device input unit 1100 may be implemented in the form of an input interface (a Universal Serial Bus (USB) port, a PS/2 port, etc.) configured to connect an external input device for receiving a user input to the wearable device 1000 instead of sensing a user input by itself.

Alternatively, the device input unit 1100 may include an imaging device such as a camera that inputs acquired imaging region data to the wearable device 1000 in addition to a means for detecting a user's intentional input.

The device output unit 1200 may perform a function of outputting information so that a user can confirm the information. The device output unit 1200 may output information acquired from a user, information acquired from an external device, and/or information processed by an external device. The information may be output visually, audibly, and/or tactilely. However, the present invention is not limited thereto, and the information may be output in various forms.

The device output unit 1200 may be implemented as a display configured to output images, a speaker configured to output sounds, a haptic device configured to generate vibration, and/or various other types of output means.

Here, the term "display" may refer to a liquid crystal display (LCD), a light-emitting diode (LED) display, an organic light-emitting diode (OLED) display, a flat panel display (FPD), and a transparent display, a curved display, a flexible display, a three-dimensional (3D) display, a holographic display, a projector, and/or an image display device in a broad sense including various types of devices capable of performing an image output function.

Alternatively, the device output unit 1200 may be implemented in the form of an output interface (a Universal Serial Bus (USB) port, a PS/2 port, etc.) configured to connect an external output device for outputting information to the wearable device 1000 instead of a device configured to output information by itself.

The device output unit 1200 may be integrally formed with the device input unit 1100. As an example, when the device output unit 1200 is a display, the device output unit 1200 may be in the form of a touch display integrally formed with a touch sensor, which is the device input unit 1100.

The device communication unit 1300 may enable the wearable device 1000 to transmit and receive data to and from an external device. According to an embodiment of the present application, the device communication unit 1300 may communicate with the user terminal 2000 and/or the monitoring server 3000.

The device communication unit 1300 may include one or more modules that enable communication. The device communication unit 1300 may include a module that enables communication with an external device in a wired manner. Alternatively, the device communication unit 1300 may include a module that enables communication with an external device in a wireless manner. Alternatively, the device communication unit 1300 may include a module that enables communication with an external device in a wireless manner and a module that enables communication with an external device in a wired manner.

As a specific example, the device communication unit 1300 may include a wired communication module that accesses the Internet through a local area network (LAN), a mobile communication module, such as the long term evolution (LTE), that accesses a mobile communication network through a mobile communication base station to transmit and receive data, a short-range communication module that uses a communication scheme based on a wireless local area network (WLAN) such as Wi-Fi or a communication scheme based on a wireless personal area network (WPAN) such as Bluetooth and Zigbee, a satellite communication module that uses a Global Navigation Satellite System (GNSS) such as Global Positioning System (GPS), or a combination thereof.

The device sensor unit 1400 may perform a function of acquiring biometric information of the user of the wearable device 1000. According to an embodiment of the present application, the device sensor unit 1400 may acquire the user's heart rate information.

The device sensor unit 1400 may include one or more modules that enable the acquisition of the user's biometric information. As a specific example, the device sensor unit

1400 may include a photoplethysmogram (PPG) sensor module that acquires heart rate information (e.g., a heart rate) using an optical scheme, an electrocardiogram (ECG) sensor module that acquires heart rate information (e.g., an electrocardiogram) through an electrical scheme, a temperature sensor module that acquires temperature information in a contact/non-contact manner, a motion sensor module that acquires information about a user's movement using an acceleration sensor, a gyro sensor, and/or a step detection sensor, etc., an electrodermal activity (EDA) sensor module that acquires information on sympathetic nervous system activity using skin conductance, or a combination thereof. However, the present invention is not limited thereto, and the device sensor unit 1400 may be implemented as various sensors for acquiring the user's biometric information.

According to an embodiment of the present application, the device sensor unit 1400 may perform a function of acquiring information on the external environment of the wearable device 1000. As an example, the device sensor unit 1400 may include a temperature sensor module configured to measure the external temperature of the wearable device 1000.

The device memory unit 1500 may store various kinds of data and programs required for the wearable device 1000 to operate. The device memory unit 1500 may store information acquired by the wearable device 1000.

As an example, the device memory unit 1500 may store biometric information acquired by the device sensor unit 1400. As another example, the device memory unit 1500 may store an operating system for driving the wearable device 1000, various kinds of programs driven or used by the wearable device 1000 to perform thyroid function monitoring, various kinds of data regarding media to be referenced by these programs, etc.

The device memory unit 1500 may temporarily or semi-permanently store data. Examples of the device memory unit 1500 may include a hard disk drive (HDD), a solid-state drive (SSD), a flash memory, a read-only memory (ROM), a random access memory (RAM), a cloud storage, etc. However, the present invention is not limited thereto, and the device memory unit 1500 may be implemented as various modules for storing data.

The device memory unit 1500 may be built into or detachable from the wearable device 1000.

The device control unit 1600 may perform a function of overseeing and controlling the overall operation of the wearable device 1000. The device control unit 1600 may compute and process various kinds of information and may control operations of the elements of a terminal.

The device control unit 1600 may be implemented with a computer or the like in hardware, software, or a combination thereof. The device control unit 1600 in hardware may be provided in the form of an electronic circuit for processing electrical signals to perform a control function, such as a CPU chip, and the device control unit 1600 in software may be provided in the form of a program for driving the device control unit 1600 in hardware.

According to an embodiment, the device control unit 1600 may perform control such that the device sensor unit 1400 senses a user's bio-signal.

According to an embodiment, the device control unit 1600 may perform control such that the device memory unit 1500 temporarily stores a sensed bio-signal and deletes the stored bio-signal after biometric information based on the bio-signal is transmitted through the device communication unit 1300.

In the following description, unless otherwise specified, the operation of the wearable device 1000 may be interpreted as being performed by control of the device control unit 1600.

The wearable device 1000 according to an embodiment of the present application may include a wearable wristband that is worn on a user's wrist to acquire biometric information, a wearable sock that is worn on a user's foot in the form of a sock to acquire biometric information, a wearable ring that is put on a user's finger to acquire biometric information, a wearable patch that is attached to a user's skin to acquire biometric information, a wearable headband that is worn on a user's head to acquire biometric information, a wearable device that is worn on a user's ear in the form of an earring or is fitted in the form of an earphone, and a wearable lens that is put on a user's eye. However, the present invention is not limited to the examples listed herein and may be implemented in various forms.

2. User Terminal 2000

Figure 3:
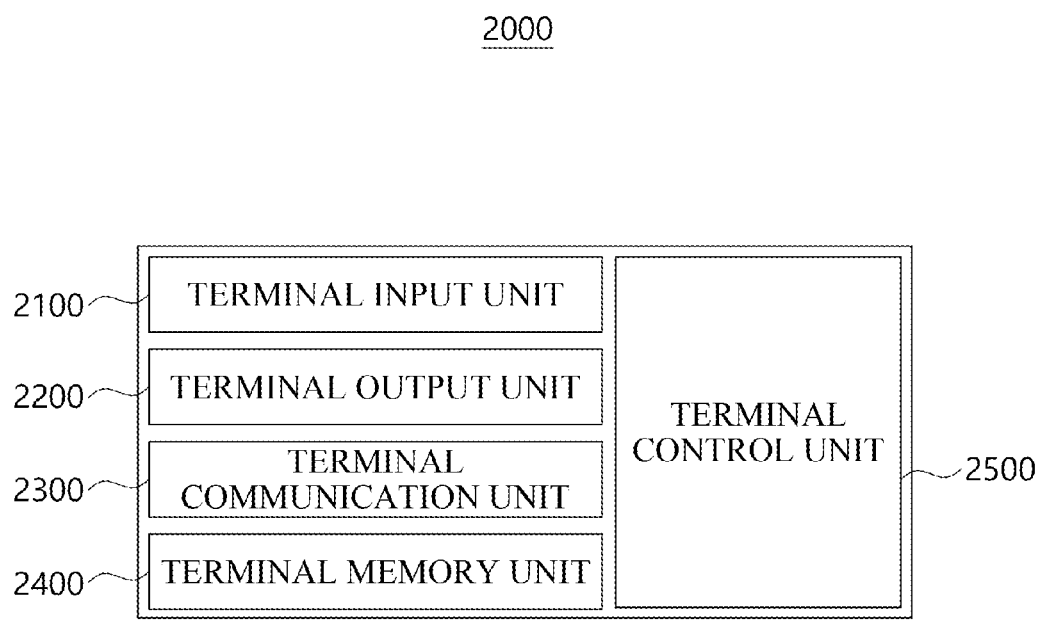
FIG. 3 is a block diagram of a user terminal according to an embodiment of the present application.

FIG. 3 is a block diagram of a user terminal 2000 according to an embodiment of the present application.

Referring to FIG. 3, the user terminal 2000 may include a terminal input unit 2100, a terminal output unit 2200, a terminal communication unit 2300, a terminal memory unit 2400, and a terminal control unit 2500. However, the components shown in FIG. 3 are not essential, and the user terminal 2000 may have more components or fewer components.

Similar to the device input unit 1100 of the wearable device 1000, the terminal input unit 2100 may perform a function of receiving information from a user.

Similar to the device output unit 1200 of the wearable device 1000, the terminal output unit 2200 may perform a function of outputting information so that a user can confirm the information.

Similar to the device communication unit 1300 of the wearable device 1000, the terminal communication unit 2300 may perform a function of transmitting or receiving data to or from an external device.

Similar to the device memory unit 1500 of the wearable device 1000, the terminal memory unit 2400 may store various kinds of data and programs required for the user terminal 2000 to operate.

Similar to the device control unit 1600 of the wearable device 1000, the terminal control unit 2500 may perform a function of overseeing and controlling the overall operation of the user terminal 2000.

According to an embodiment, the terminal control unit 2500 may perform control such that information is processed based on a user input entered through the terminal input unit 2100 and transmit the processed information to the monitoring server 3000 through the terminal communication unit 2300. As a specific example, the terminal control unit 2500 may acquire thyroid state information and/or medication information through the terminal input unit 2100, process the corresponding information according to a format for communication with the monitoring server 3000, and transmit the processed information through the terminal communication unit 2300.

According to another embodiment, the terminal control unit 2500 may process information received from the monitoring server 3000 through the terminal communication unit 2300 and provide the processed information to a user through the terminal output unit 2200. As a specific example, the terminal control unit 2500 may receive information corresponding to a thyroid function monitoring result through the terminal communication unit 2300 and output a result of determination about thyroid dysfunction through the terminal output unit 2200 in order to warn a user through thyroid function.

In the following description, unless otherwise specified, the operation of the user terminal 2000 may be interpreted as being performed by control of the terminal control unit 2500.

Accordingly, the redundant description of modules for the terminal input unit 2100, the terminal output unit 2200, the terminal communication unit 2300, the terminal memory unit 2400, and the terminal control unit 2500 will be omitted.

The user terminal 2000 according to an embodiment of the present application may include mobile terminals, such as a cellular phone, a smartphone, a tablet PC, a laptop computer, a personal digital assistant (PDA), a portable multimedia player (PMP), and a navigation device, and also stationary terminals, such as a digital TV, a desktop computer, and a kiosk. More generally, anything that can be connected to other electronic devices and/or servers over a network to exchange information may become the user terminal 2000 in the specification of the present application.

3. Monitoring Server 3000

Figure 4:
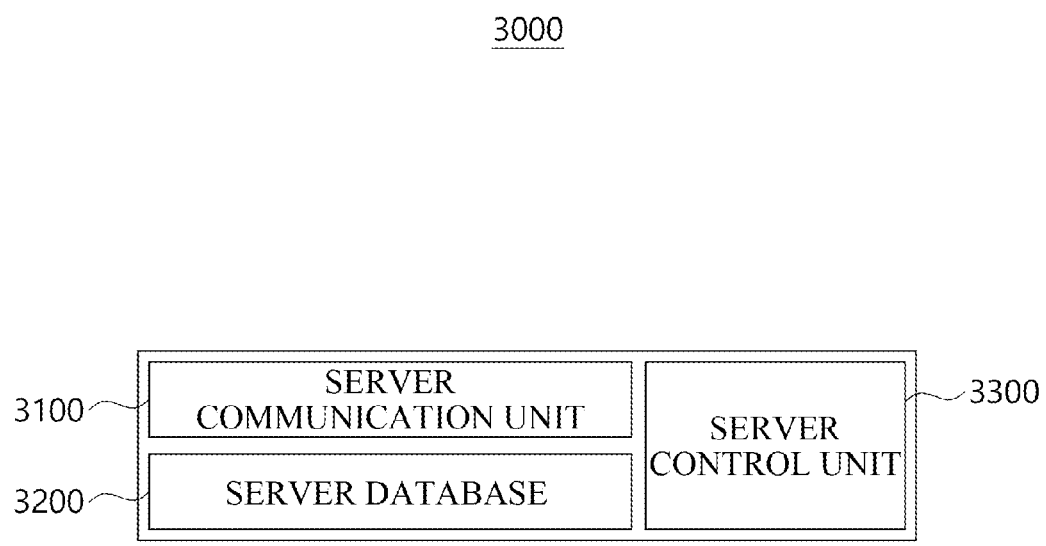
FIG. 4 is a block diagram of a monitoring server according to an embodiment of the present application.

FIG. 4 is a block diagram of a monitoring server 3000 according to an embodiment of the present application.

Referring to FIG. 4, the monitoring server 3000 may include a server communication unit 3100, a server database 3200, and a server control unit 3300. However, the components shown in FIG. 4 are not essential, and the monitoring server 3000 may have more components or fewer components. Also, the components of the monitoring server 3000 may be physically included in one server or may be a distributed server in which the components are distributed by function.

Similar to the device communication unit 1300 of the wearable device 1000, the server communication unit 3100 may perform a function of transmitting or receiving data to or from an external device. Accordingly, the redundant description of modules for the server communication unit 3100 will be omitted.

According to an embodiment of the present application, the server communication unit 3100 may receive information regarding a user's biometric information of the wearable device 1000 from the user terminal 2000. According to an embodiment of the present application, the server communication unit 3100 may receive a user's thyroid state information acquired through the user terminal 2000.

Similar to the device memory unit 1500 of the wearable device 1000, the server database 3200 may store various kinds of data and programs required for the monitoring server 3000 to operate. Accordingly, the redundant description of modules for the server database 3200 will be omitted.

According to an embodiment of the present application, the server database 3200 may store a monitoring algorithm, user information, and/or a user's biometric information used for thyroid function prediction.

Similar to the device control unit 1600 of the wearable device 1000, the server control unit 3300 may perform a function of overseeing and controlling the overall operation of the monitoring server 3000. Accordingly, the redundant description of modules for the server control unit 3300 will be omitted.

According to an embodiment, the server control unit 3300 may predict a user's thyroid function on the basis of the user's biometric information received through the server communication unit 3100 using the monitoring algorithm stored in the server database 3200. Specifically, the server control unit 3300 may calculate reference data on the basis of the thyroid state information and the biometric information received through the server communication unit 3100. Also, the server control unit 3300 may calculate monitoring data on the basis of the biometric information received through the server communication unit 3100.

According to another embodiment, the server control unit 3300 may select a specific monitoring algorithm from among monitoring algorithms stored in the server database 3200 on the basis of medication information received through the server communication unit 3100. The server control unit 3300 may perform thyroid function monitoring on the basis of the selected monitoring algorithm.

In the following description, unless otherwise specified, the operation of the monitoring server 3000 may be interpreted as being performed by control of the server control unit 3300.

The monitoring server 3000 according to an embodiment of the present application may include computer hardware in which a thyroid function monitoring program is executed or a computer program that provides a service to another program and/or an electronic device.

The monitoring server 3000 according to an embodiment of the present application may manage or control a network to which an external terminal and a server are connected and may share software resources such as data used for thyroid function monitoring. The monitoring server 3000 may be physically a single server or a distributed server in which a plurality of servers have distributed throughputs or roles.

The operation of the thyroid function monitoring system 100 according to an embodiment of the present application will be described in detail below.

In describing the operation of the thyroid function monitoring system 100 in detail, except where otherwise noted, the thyroid function monitoring system 100 includes a wearable device 1000, a user terminal 2000, and a monitoring server 3000. In the following description, the wearable device 1000 is a wearable watch, the user terminal 2000 is a smartphone with a display, and the monitoring server 3000 is a single server.

However, this merely discloses a detailed description based on an embodiment for convenience of description and does not mean that the scope of the present application should be construed as being limited by the embodiments disclosed in this specification. The scope of the present application should be determined according to the principles of interpretation of the claims.

<Operation of Thyroid Function Monitoring System 100>

1. Operation of Thyroid Dysfunction Monitoring S100

1.1 Thyroid Dysfunction Monitoring S100

The thyroid function monitoring system 100 of the present application may predict a user's thyroid dysfunction on the basis of a user's bio-signal. According to an embodiment of the present application, the thyroid function monitoring system 100 may determine thyroid dysfunction on the basis of a user's heart rate information.

Here, the term "thyroid dysfunction" may refer to the development of any one of hyperthyroidism, hypothyroidism, and thyrotoxicosis.

Here, the phrase "prediction of thyroid dysfunction" may refer to the acquisition of information on a result of monitoring thyroid dysfunction based on the user's biometric information and may be used herein interchangeably with the phrase "determination of thyroid dysfunction" or "diagnosis of thyroid dysfunction."

Figure 5:
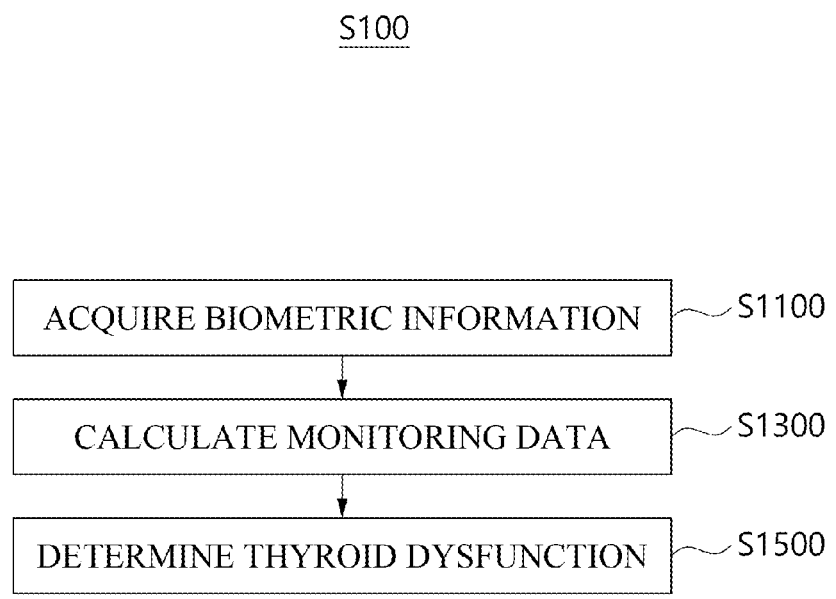
FIG. 5 is a flowchart illustrating a thyroid function monitoring method according to an embodiment of the present application.

FIG. 5 is a flowchart illustrating a thyroid function monitoring method S100 according to an embodiment of the present application.

Referring to FIG. 5, when biometric information is acquired (S1100), monitoring data may be calculated (S1300), and a user's thyroid dysfunction may be determined (S1500). According to an embodiment, the above-described operations S1100, S1300, and S1500 may be performed by the monitoring server 3000.

1.1.1 Acquisition of Biometric Information (S1100).

The wearable device 1000 may acquire a user's biometric information. The wearable device 1000 may acquire biometric information of a user who wears the wearable device 1000.

The acquisition of the user's biometric information through the wearable device 1000 may be performed at predetermined intervals.

As an example, the device sensor unit 1400 of the wearable device 1000 may include a PPG sensor, and the wearable device 1000 may acquire the user's heart rate information using the PPG sensor at a first interval. The device sensor unit 1400 of the wearable device 1000 may include a motion sensor, and the wearable device 1000 may acquire the user's motion information using a motion sensor at a second interval. The first interval may be the same as the second interval. The first interval may be different from the second interval.

The wearable device 1000 may transmit the user's biometric information to the user terminal 2000. As an example, as soon as the user's biometric information is acquired, the wearable device 1000 may transmit the acquired biometric information to the user terminal 2000. As another example, the wearable device 1000 may transmit the user's acquired set of biometric information to the user terminal 2000 at predetermined intervals. In this case, the interval at which the wearable device 1000 acquires the user's biometric information may be shorter than the interval at which the wearable device 1000 transmits the user's biometric information.

The wearable device 1000 may transmit one or more kinds of biometric information of the user to the user terminal 2000. As an example, the biometric information transmitted to the user terminal 2000 may be heart rate information. As another example, the biometric information transmitted to the user terminal 2000 may be heart rate information or motion information.

The biometric information transmitted by the wearable device 1000 may be associated with other information. As an example, the biometric information transmitted by the wearable device 1000 may be heart rate information associated with time. As another example, the biometric information transmitted by the wearable device 1000 may be heart rate information associated with time and motion information associated with time. As another example, the biometric information transmitted by the wearable device 1000 may be in a form in which time, heart rate information, and motion information are associated with each other.

The user terminal 2000 may transmit the received biometric information to the monitoring server 3000. As an example, as soon as the user's biometric information is received, the user terminal 2000 may transmit the received biometric information to the monitoring server 3000. As another example, the user terminal 2000 may transmit a received set of biometric information of a plurality of users to the monitoring server 3000 at predetermined intervals. In this case, the interval at which the user terminal 2000 acquires a set of biometric information may be shorter than the interval at which the user terminal 2000 transmits the set of biometric information.

The monitoring server 3000 may acquire biometric information from the user terminal 2000 (S1100). The server communication unit 3100 may acquire biometric information from the user terminal 2000 (S1100). The monitoring server 3000 may receive, through the user terminal 2000, biometric information sensed by the wearable device 1000 that has been transformed into an appropriate form.

1.1.2 Calculation of Monitoring Data (S1300)

The monitoring server 3000 may calculate monitoring data on the basis of acquired biometric information (S1300). The server control unit 3300 may calculate monitoring data (S1300).

Here, the term "monitoring data" may refer to a user's state data for a monitoring period that is subject to thyroid function determination in one operation of determining thyroid dysfunction (S1500).

As an example, the "monitoring data" may be calculated based on a user's state data of the monitoring period (e.g., a plurality of consecutive days before the thyroid dysfunction determination S1500). As another example, the "monitoring data" may be calculated based on the user's state data for one or more periods (e.g., a resting period) satisfying a predetermined criterion in the monitoring period.

According to an embodiment of the present application, the monitoring data may be calculated based on the user's state data when the user is in a stable state in the monitoring period. According to another embodiment of the present application, the monitoring data may be calculated based on the user's state data when the user is in a resting state in the monitoring period.

Figure 6:
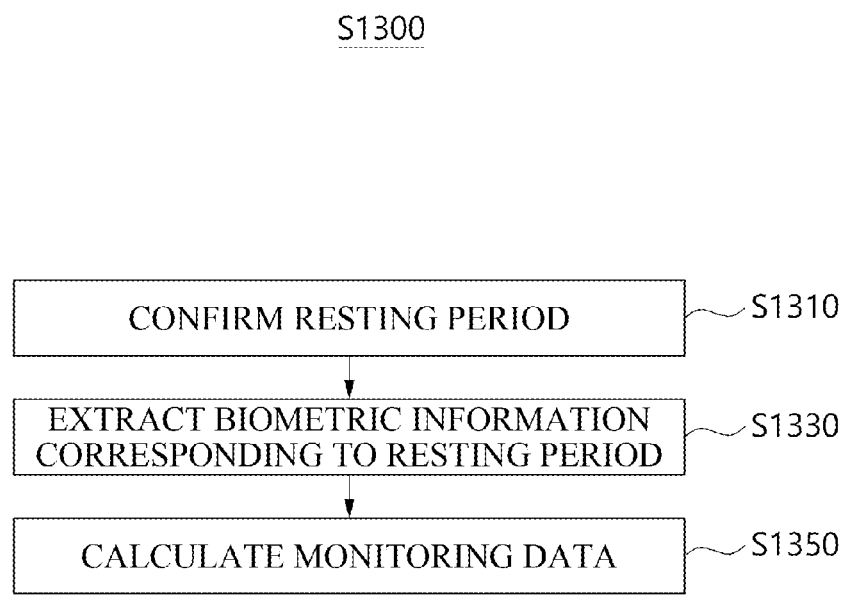
FIG. 6 is a flowchart illustrating a monitoring data calculation method according to an embodiment of the present application.

FIG. 6 is a flowchart illustrating a monitoring data calculation method S1300 according to an embodiment of the present application.

The monitoring data calculation method S1300 may include confirming a resting period (S1310), extracting biometric information corresponding to the resting period (S1330), and calculating monitoring data (S1350). According to an embodiment, the above-described operations S1310, S1330, and S1350 may be performed by the monitoring server 3000.

The monitoring server 3000 may confirm the resting period (S1310). The server control unit 3300 may confirm the resting period (S1310). The monitoring server 3000 may confirm at least one resting period during a predetermined period (e.g., a monitoring period) (S1310). As an example, the monitoring period may be one day (24 hours). As another example, the predetermined period may be a plurality of days (e.g., five days). As another example, the monitoring period may be shorter than one day.

The monitoring server 3000 may confirm a resting period corresponding to a predetermined criterion during the predetermined period (S1310). As an example, the monitoring server 3000 may confirm the resting period in the monitoring period on the basis of the user's exercise information (S1310).

The predetermined criterion for confirming the resting period may be associated with the user's motion information. As a specific example, the resting period may be determined as a period where it is determined that a predetermined time (e.g., five minutes) has elapsed without the user's movement according to the user's motion information. As another example, the predetermined criterion may be associated with the user's skin conductance information. As a specific example, the resting period may be determined as a period where it is determined that a user is sleeping, according to the user's skin conductance information.

There are a plurality of resting periods confirmed through operation S1310. A plurality of resting periods may be included in the monitoring period. The plurality of resting periods may be discontinuous from one another. As an example, between one resting period and another resting period, there may be a period in which the user's movement is sensed. In other words, one resting period, another resting period, and a period where a user's movement is sensed may be included in the monitoring period.

The monitoring server 3000 may extract biometric information corresponding to the resting period (S1330). The server control unit 3300 may extract biometric information corresponding to the resting period (S1330). The monitoring server 3000 may extract biometric information corresponding to one or more confirmed resting periods (S1330). The monitoring server 3000 may extract biometric information corresponding to the one or more confirmed resting periods included in the monitoring period (S1330).

The monitoring server 3000 may extract heart rate information corresponding to the confirmed resting period included in the monitoring period. Alternatively, the monitoring server 3000 may extract temperature information corresponding to the confirmed resting period included in the monitoring period. Alternatively, the monitoring server 3000 may extract skin conductance information corresponding to the confirmed resting period included in the monitoring period.

According to an embodiment of the present application, the monitoring server 3000 may extract a plurality of pieces of heart rate information corresponding to a plurality of confirmed resting periods included in the monitoring period.

The monitoring server 3000 may calculate monitoring data (S1350). The server control unit 3300 may calculate monitoring data (S1350). The monitoring server 3000 may calculate monitoring data on the basis of the extracted biometric information (S1350).

As an example, the monitoring server 3000 may calculate, as the monitoring data, the average of the plurality of pieces of heart rate information corresponding to the plurality of confirmed resting periods included in the monitoring period. As another example, the monitoring server 3000 may calculate, as the monitoring data, the median of the medians of the plurality of pieces of heart rate information corresponding to the plurality of resting periods included in the monitoring period. As another example, the monitoring server 3000 may calculate, as the monitoring data, an arithmetic operation value of the remaining heart rate information other than the maximum and the minimum of the plurality of pieces of heart rate information corresponding to the plurality of resting periods included in the monitoring period.

1.1.3 Calculation of Reference Data (S200)

1.1.3.1 Reference Data

The monitoring server 3000 according to an embodiment of the present application may use reference data. Here, the term "reference data" may refer to reference data that is compared to monitoring data when an operation of determining thyroid dysfunction is performed.

According to an embodiment of the present application, the reference data may be determined based on a user's biometric information when state information regarding the user's thyroid function is normal. According to another embodiment of the present application, the reference data may be determined based on a user's biometric information in a corresponding period when the user's biometric information corresponds to a predetermined criterion.

1.1.3.2 Method of Calculating Reference Data

Figure 7:
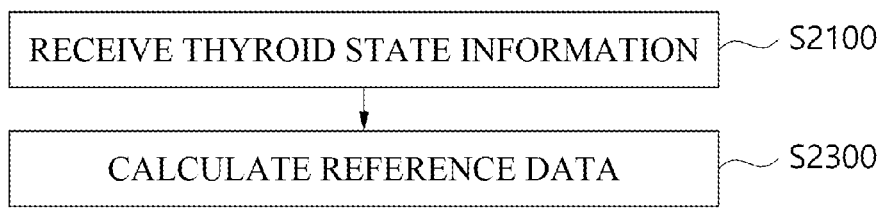
FIG. 7 is a flowchart illustrating a reference data calculation method according to an embodiment of the present application.

FIG. 7 is a flowchart illustrating a reference data calculation method S200 according to an embodiment of the present application.

Referring to FIG. 7, the monitoring server 3000 may calculate reference data (S2300) when the thyroid state information is received (S2100).

The monitoring server 3000 may receive thyroid state information from the user terminal 2000 (S2100). The server communication unit 3100 may receive thyroid state information from the terminal communication unit 2300 (S2100).

According to an embodiment of the present application, the user terminal 2000 may receive a user's thyroid state information through the terminal input unit 2100. In this case, the thyroid state information may be information regarding a thyroid hormone level acquired through the user's blood test or the like. Alternatively, the thyroid state information may be information regarding a thyroid state acquired through a questionnaire about the user's symptoms.

The user terminal 2000 may transmit the received thyroid state information to the monitoring server 3000.

The monitoring server 3000 may calculate reference data (S2300) when the thyroid state information is received (S2100). The server control unit 3300 may calculate reference data (S2300) when the thyroid state information is received.

Figure 8:
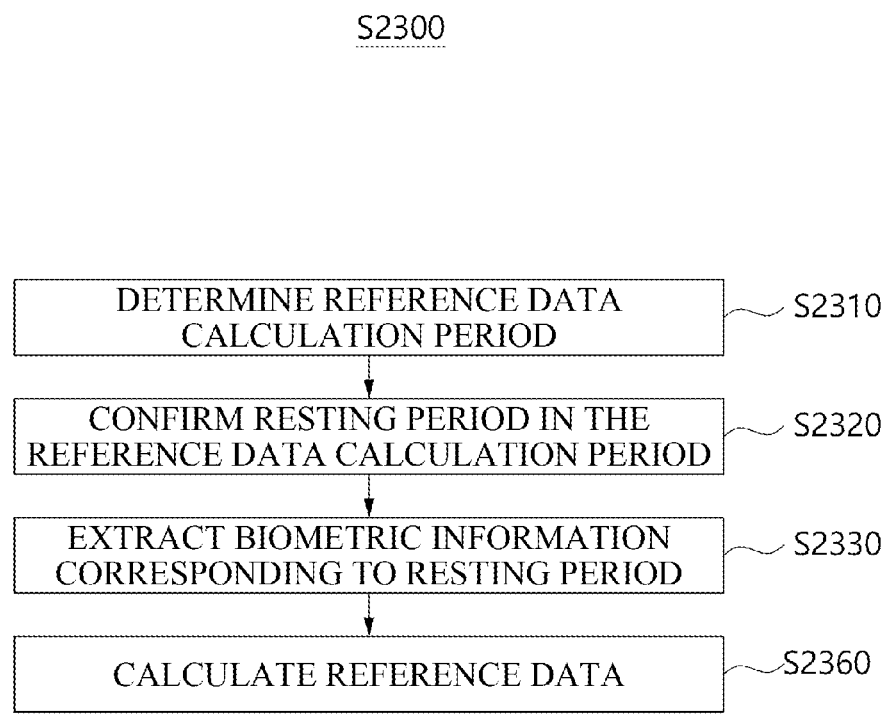
FIG. 8 is a flowchart illustrating a reference data calculation method according to an embodiment of the present application.

FIG. 8 is a flowchart illustrating a reference data calculation method S2300 according to an embodiment of the present application.

The reference data calculation method S2300 may include determining a reference data calculation period (S2310), confirming a resting period in the reference data calculation period (S2320), extracting biometric information corresponding to the resting period (S2330), and calculating reference data (S2360). According to an embodiment, the operations S2310, S2320, S2330, and S2360 may be performed by the monitoring server 3000.

The monitoring server 3000 may determine a reference data calculation period (S2310). The server control unit 3300 may determine a reference data calculation period (S2310). The server control unit 3300 may determine the reference data calculation period on the basis of information stored in the server database 3200 (S2310).

The monitoring server 3000 may determine a reference data calculation period on the basis of received thyroid state information (S2310). According to this specification, the reference data calculation period may be used interchangeably with a reference period.

The reference data calculation period may be a period in which the user's thyroid function corresponds to "normal" according to the thyroid state information.

As an example, when the received thyroid state information corresponds to a normal range, a predetermined period before and after the thyroid state information is input may be determined as the reference data calculation period.

As another example, when there are a plurality of inputs of thyroid state information, predetermined periods before and after the thyroid state information corresponding to "normal" is input may be determined as the reference data calculation period. As a specific example, when thyroid state information on normal thyroid hormone levels is input on March $1^{st}$, thyroid state information on abnormal thyroid hormone levels is input on June $1^{st}$, and thyroid state information on normal thyroid hormone levels is input on September $1^{st}$, then a predetermined period with respect to March $1^{st}$ (e.g., five days from February $27^{th}$ to March $3^{rd}$) and a predetermined period with respect to September $1^{st}$ (e.g., five days from August 30$^{th}$ to September 3$^{rd}$) may be determined as a reference data calculation period.

The monitoring server 3000 may confirm a resting period corresponding to the determined reference data calculation period (S2320). The server control unit 3300 may confirm a resting period corresponding to the determined reference data calculation period (S2320). The server control unit 3300 may confirm a resting period corresponding to the determined reference data calculation period on the basis of a condition stored in the server database 3200 (S2320).

The resting period in operation S2320 may be determined as a criterion corresponding to a criterion where a resting period is confirmed upon calculation of the monitoring data. As an example, when the resting period in operation S1310 is determined as a period in which a predetermined time (e.g., five minutes) has elapsed while the user does not move, the resting period in S2320 may be determined as a period in which a predetermined time (e.g., five minutes) has elapsed while the user does not move.

There are a plurality of resting periods confirmed through operation S2320. A plurality of resting periods may be included in the reference data calculation period. The plurality of resting periods may be discontinuous from one another. As an example, between one resting period and another resting period, there may be a period in which the user's movement is sensed. In other words, one resting period, another resting period, and a period where a user's movement is sensed may be included in the reference data calculation period.

The monitoring server 3000 may extract biometric information corresponding to the resting period (S2330). The server control unit 3300 may extract biometric information corresponding to the resting period (S2330). The monitoring server 3000 may extract biometric information corresponding to one or more confirmed resting periods (S2330). The monitoring server 3000 may extract biometric information corresponding to one or more confirmed resting periods included in the reference data calculation period (S2330).

The monitoring server 3000 may extract heart rate information corresponding to a confirmed resting period included in the reference data calculation period. Alternatively, the monitoring server 3000 may extract temperature information corresponding to a confirmed resting period included in the reference data calculation period. Alternatively, the monitoring server 3000 may extract skin conductance information corresponding to a confirmed resting period included in the reference data calculation period.

According to an embodiment of the present application, the monitoring server 3000 may extract a plurality of pieces of heart rate information corresponding to a plurality of confirmed resting periods included in the reference data calculation period.

The biometric information in the period (S2330) may correspond to biometric information extracted upon the calculation of monitoring data. As an example, when a heart rate is extracted as the biometric information in operation S1330, a heart rate may be extracted as the biometric information in operation S2330. As another example, when skin conductance is extracted as the biometric information in operation S1330, skin conductance may be extracted as the biometric information in operation S2330.

The monitoring server 3000 may calculate reference data (S2360). The server control unit 3300 may calculate reference data (S2360). The monitoring server 3000 may calculate reference data on the basis of the extracted biometric information (S2360).

As an example, the monitoring server 3000 may calculate, as the reference data, the average of the plurality of pieces of heart rate information corresponding to the plurality of confirmed resting periods included in the reference data calculation period. As another example, the monitoring server 3000 may calculate, as the reference data, the median of the medians of the plurality of pieces of heart rate information corresponding to the plurality of resting periods included in the reference data calculation period. As another example, the monitoring server 3000 may calculate, as the reference data, an arithmetic operation value of the remaining heart rate information other than the maximum and the minimum of the plurality of pieces of heart rate information corresponding to the plurality of resting periods included in the reference data calculation period.

Figure 9:
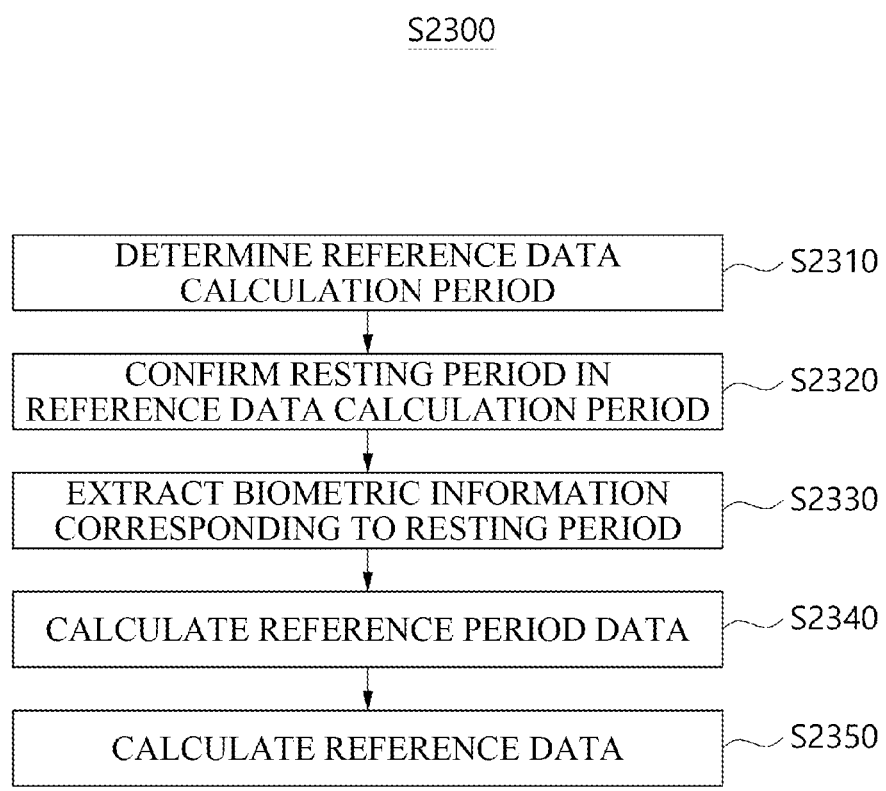
FIG. 9 is a diagram illustrating a reference data calculation method when a monitoring server receives thyroid state information outside a normal range according to an embodiment of the present application.

FIG. 9 is a diagram illustrating a reference data calculation method when a monitoring server 3000 receives thyroid state information outside a normal range according to an embodiment of the present application.

The monitoring server 3000 may determine a reference data calculation period (S2310), confirm a resting period in the reference data calculation period (S2320), and extract biometric information in the confirmed resting period (S2330).

In S2310, the reference data calculation period may be a period in which a user's thyroid function corresponds to "normal" according to the received thyroid state information, as described above.

In S2310, the reference data calculation period may be a period in which a user's thyroid function corresponds to "abnormal" according to the received thyroid state information when the monitoring server 3000 does not receive the user's thyroid state information in the normal range (i.e., when the thyroid state information received by the monitoring server 3000 is outside the normal range).

As an example, when the received thyroid state information does not correspond to a normal range, a predetermined period before and after the thyroid state information is input may be determined as the reference data calculation period.

The monitoring server 3000 may confirm a resting period corresponding to the determined reference data calculation period (S2320) and extract biometric information corresponding to the resting period (S2330). Operations S2320 and S2330 have already been described in detail, and thus a redundant description will be omitted.

The monitoring server 3000 may calculate reference period data (S2340). The server control unit 3300 may calculate reference period data (S2340). The monitoring server 3000 may calculate reference period data on the basis of the biometric information corresponding to the resting period included in the reference data calculation period.

As an example, the monitoring server 3000 may calculate, as the reference time data, the average of the plurality of pieces of heart rate information corresponding to the plurality of confirmed resting periods included in the reference data calculation period. As another example, the monitoring server 3000 may calculate, as the reference period data, the median of the medians of the plurality of pieces of heart rate information corresponding to the plurality of resting periods included in the reference data calculation period. As another example, the monitoring server 3000 may calculate, as the reference period data, an arithmetic operation value of the remaining heart rate information other than the maximum and the minimum of the plurality of pieces of heart rate information corresponding to the plurality of resting periods included in the reference data calculation period.

In this case, the reference period data calculated in operation S2340 may be data calculated using biometric information when a user's thyroid function is estimated as "abnormal."

The monitoring server 3000 may calculate reference data (S2350). The server control unit 3300 may calculate reference data (S2350). The monitoring server 3000 may calculate reference data on the basis of the received thyroid state information (S2350). The monitoring server 3000 may calculate reference data by correcting the reference period data on the basis of the received thyroid state information (S2350).

As an example, the monitoring server 3000 may compute by which ng/dL the user's hormone level corresponding to the received thyroid state information should be increased or decreased in order to match the hormone level to a normal range and may estimate the amount of change in biometric information corresponding to the increase or the decrease. The monitoring server 3000 may calculate the reference data by adding or subtracting the estimated amount of change in biometric information to or from the reference period data (S2350).

The monitoring server 3000 may store data necessary to correct the reference period data. As an example, data on the associations between resting heart rates and hormone levels of multiple users may be stored in the monitoring server 3000. As a specific example, statistical data on roughly how many times the heart rate increases when the hormone level increases by 0.1 ng/dL may be stored in the monitoring server 3000.

So far, the method of the monitoring server 3000 calculating the reference data when the thyroid state information is received from the user terminal 2000 has been described in detail.

According to an embodiment of the present application, when the user's thyroid state information is not stored, the monitoring server 3000 may transmit a signal to the user terminal 2000 in order to receive thyroid state information through the user terminal 2000. As an example, the monitoring server 3000 may transmit a necessary signal to the user terminal 2000 so that an input interface for receiving the thyroid state information is output through the terminal output unit 2200 of the user terminal 2000.

According to an embodiment of the present application, when the user's thyroid state information is not stored, the monitoring server 3000 may calculate reference data on the basis of the monitoring data calculated in operation S1300. As a specific example, the monitoring server 3000 may calculate reference data on the basis of the user's heart rate acquired for a predetermined number of days. The monitoring server 3000 may calculate reference data on the basis of a heart rate of each user in a plurality of resting periods acquired for a predetermined number of days. In this case, the predetermined number of days may be a period longer than the monitoring period.

1.1.3.3 when Reference Data is Calculated

According to an embodiment of the present application, reference data may be calculated by using reception of thyroid state information as a trigger. According to another embodiment of the present application, reference data may be calculated by the monitoring server 3000 at predetermined intervals. According to another embodiment of the present application, reference data may be calculated when the monitoring server 3000 receives a signal for calculating the reference data from an external device (e.g., the user terminal 2000).

According to another embodiment of the present application, reference data may be calculated whenever monitoring data is calculated. In other words, the monitoring server 3000 may calculate monitoring data and then newly calculate reference data. Alternatively, before calculating the monitoring data, the monitoring server 3000 may newly calculate reference data and compare the two pieces of data.

1.1.4 Determination of Thyroid Dysfunction (S1500)

Following FIG. 5, the thyroid function monitoring S100 according to an embodiment of the present application may be performed through biometric information acquisition S1100, monitoring data calculation S1300, and thyroid dysfunction determination S1500.

Figure 10:
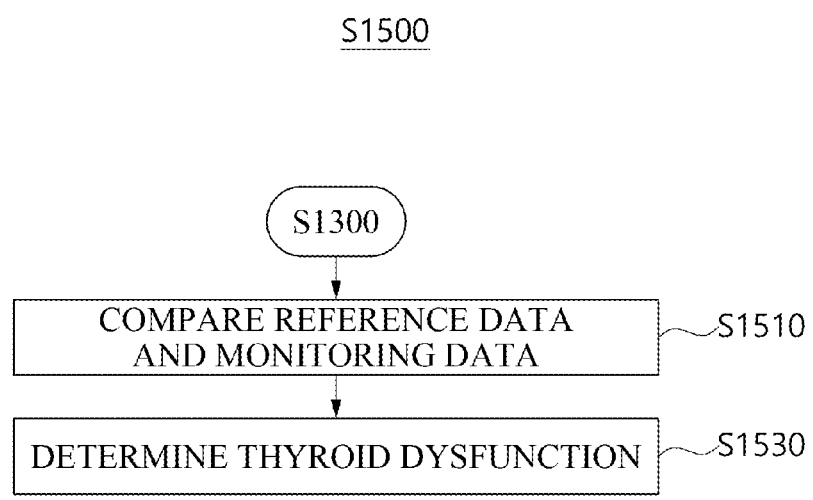
FIG. 10 is a flowchart illustrating a thyroid dysfunction determination method according to an embodiment of the present application.

FIG. 10 is a flowchart illustrating a method for thyroid dysfunction determination S1500 according to an embodiment of the present application.

Referring to FIG. 10, the monitoring server 3000 may calculate monitoring data (S1300) and then compare the monitoring data to reference data (S1510). The server control unit 3300 may compare the monitoring data and the reference data (S1510).

An algorithm for comparing the monitoring data and the reference data may be variously designed. The algorithm for comparing the reference data and the monitoring data may be stored in the server database 3200 of the monitoring server 3000.

As an example, the algorithm for comparing the reference data and the monitoring data may be designed to perform the thyroid dysfunction determination (S1530) when the monitoring data is greater than the reference data beyond a predetermined numerical range. As another example, the algorithm for comparing the reference data and the monitoring data may be designed to perform the thyroid dysfunction determination (S1530) when the monitoring data is smaller than the reference data beyond a predetermined numerical range. As another example, the algorithm for comparing the reference data and the monitoring data may be designed to perform the thyroid dysfunction determination (S1530) when the monitoring data is smaller than or greater than the reference data beyond a predetermined numerical range.

By comparing the reference data and the monitoring data in operation S1510, when it is determined that a preset condition is satisfied, the monitoring server 3000 may determine that a user's thyroid function is abnormal (S1530). The server control unit 3300 may compare the monitoring data and the reference data (S1510) and may determine that the thyroid function is abnormal when the comparison result corresponds to a predetermined criterion (S1530).

When, in operation S1530, it is determined that the user's thyroid function is abnormal, the monitoring server 3000 may transmit a signal to the user terminal 2000 such that an alert of the user's thyroid dysfunction is output through the terminal output unit 2200 of the user terminal 2000. As an example, the user terminal 2000 may perform control such that an alert of the user's hyperthyroidism is output through the terminal output unit 2200 in response to a signal received from the monitoring server 3000. As another example, the user terminal 2000 may perform control such that an alert of the user's hypothyroidism is output through the terminal output unit 2200 in response to a signal received from the monitoring server 3000. As another example, the user terminal 2000 may perform control such that an alert of the user's thyrotoxicosis is output through the terminal output unit 2200 in response to a signal received from the monitoring server 3000. As another example, when the user terminal 2000 receives a signal corresponding to S1530 from the monitoring server 3000 more than a predetermined number of times for a predetermined period, the user terminal 2000 may perform control such that a comment suggesting that an expert's opinion be given is output through the terminal output unit 2200 in addition to the alert of the user's thyrotoxicosis.

The alert related to the thyroid dysfunction may be a alert about whether or not a disease has developed, an alert about the possibility (or risk) of a disease, or an inducement to visit a hospital.

The alert related to the thyroid dysfunction may be a visual output through a display panel or the like or an audible output through a speaker or the like, but the present invention is not limited thereto.

Figure 11:
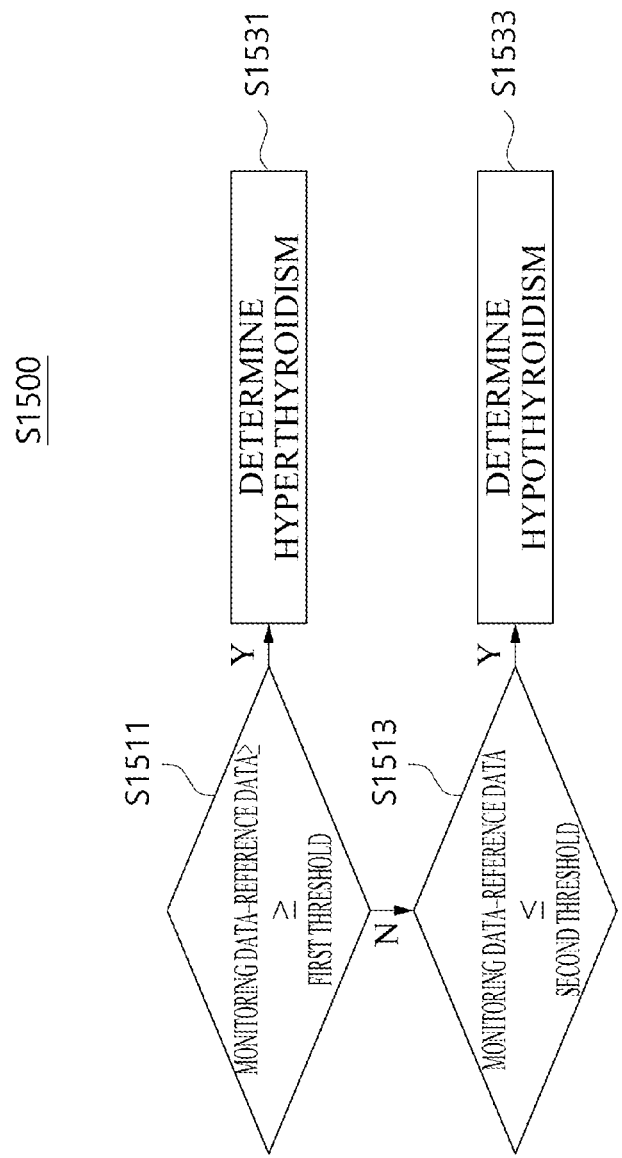
FIG. 11 is a flowchart illustrating an algorithm for comparing reference data and monitoring data according to an embodiment of the present application.

FIG. 11 is a flowchart illustrating an algorithm for comparing reference data and monitoring data according to an embodiment of the present application.

The monitoring server 3000 may compare the monitoring data and the reference data. The monitoring server 3000 may compare whether the monitoring data is greater than the reference data by a first threshold or more (S1511).

When the monitoring data is greater than the reference data by the first threshold or more, the monitoring server 3000 may determine that the user's thyroid function is abnormal. As an example, when a monitoring heart rate is greater than a reference heart rate by a first threshold (e.g., 10) or more, the monitoring server 3000 may determine that the user's thyroid function is abnormal. The monitoring server 3000 may predict the user's hyperthyroidism (S1531). The monitoring server 3000 may diagnose the user's hyperthyroidism (S1531). The monitoring server 3000 may determine the user's hyperthyroidism (S1531).

When, in operation S1531, it is determined that the user's thyroid function is abnormal, the monitoring server 3000 may transmit a signal to the user terminal 2000 such that an alert related to the user's thyroid dysfunction is output through the terminal output unit 2200 of the user terminal 2000.

When the monitoring data is not greater than the reference data by the first threshold or more, the monitoring server 3000 may compare whether the monitoring data is smaller than the reference data by a second threshold or more (S1513).

When the monitoring data is smaller than the reference data by the second threshold or more, the monitoring server 3000 may determine that the user's thyroid function is abnormal. As an example, when a monitoring heart rate is smaller than a reference heart rate by a second threshold (e.g., 8) or more, the monitoring server 3000 may determine that the user's thyroid function is abnormal. The monitoring server 3000 may predict the user's hypothyroidism (S1531). The monitoring server 3000 may diagnose the user's hypothyroidism (S1531). The monitoring server 3000 may determine the user's hypothyroidism (S1531).

When, in operation S1533, it is determined that the user's thyroid function is abnormal, the monitoring server 3000 may transmit a signal to the user terminal 2000 such that an alert related to the user's thyroid dysfunction is output through the terminal output unit 2200 of the user terminal 2000.

FIGS. 12 to 16 show the contents of a clinical study on the correlation between hypothyroidism and heart rate as a basis for a monitoring system according to an embodiment of the present application to predict thyroid dysfunction.

In this clinical study, in order to confirm the association between hypothyroidism and a heart rate, 44 hypothyroid patients (the clinical subjects below) after thyroidectomy were recruited to wear a wearable device and continuously monitor their heart rates. The wearable device used in the clinical study was Fitbit Charge 2™. The clinical subjects wearing the wearable device visited the hospital three times, and the concentration of thyroid hormone that changed according to the discontinuation and maintenance of a thyroid hormone drug during thyroid hormone drug treatment was compared to the change in heart rate measured with the wearable device.

Specifically, the patients participating in this clinical study were classified into two clinical groups. The first clinical group consisted of 30 clinical subjects, and the clinical subjects classified into the first clinical group visited the hospital three times and were induced to take a thyroid hormone drug before the first visit and from the second visit to the third visit and not to take a thyroid hormone drug one month before the second visit for a period between the first visit and the second visit. As a result, the patients had a normal thyroid function upon the first visit and the third visit and had hypothyroidism upon the second visit, so the first clinical group was classified as a hypothyroidism group. The second clinical group consisted of 14 clinical subjects, and the clinical subjects classified into the second clinical group visited the hospital three times and were induced to take a thyroid hormone drug from before the first visit to the third visit. As a result, the patients had a normal thyroid function upon the first visit, the second visit, and the third visit, so the second clinical group was classified as a control group.

FIG. 12 is a diagram showing characteristics of each clinical group of clinical subjects participating in a clinical study process. In FIG. 12, "Age" is age, "Gender" is gender, "Body mass index" is a body mass index, "Systolic blood pressure" is a systolic blood pressure, "Diastolic blood pressure" is diastolic blood pressure, "On-site resting heart rate" is a heart rate measured with an automatic sphygmomanometer at the time of a patient visit, "Thyroid function test" indicates thyroid hormone concentrations measured at the time of a patient visit, "Free T4" is thyroid hormone, "TSH" is thyroid stimulating hormone, "Glucose" is glucose, "BUN" is blood urea nitrogen, "Creatinine" is creatine, "Total cholesterol" is total cholesterol, "Total Protein" is total protein, "Albumin" is albumin, "AST" is aspartate transaminase, "ALT" is alanine transaminase, "WBC" is white blood cell, "Hemoglobin" is hemoglobin, and "Platelet" is platelet. Values shown for each characteristic in FIG. 12 represent the average and standard deviation of values corresponding to values corresponding to each characteristic of a plurality of clinical subjects belonging to the clinical group and are expressed as (mean)±(standard deviation).

FIG. 13 is a diagram showing changes in thyroid function parameters between a first hospital visit and a second hospital visit for clinical subjects participating in a clinical study process. In FIG. 13, "Free T4" is a thyroid hormone concentration, "TSH" is a thyroid stimulating hormone concentration, "Zulewski's clinical score" is Zulewski's clinical score for hypothyroidism, "On-site rHR" is a resting heart rate measured in a conventional method after 15 minutes of rest at the time of a hospital visit, "WD-rHR" is the average of resting heart rates measured by a wearable device during a period of five days before a hospital visit, "WD-sleepHR" is the average of sleeping heart rates measured by a wearable device for a period of five days before a hospital visit, and "WD-2to6HR" is the average of heart rates measured by a wearable device from 2:00 AM to 6:00 AM for a period of five days before a hospital visit.

In FIG. 13, Visit 1 or 3 indicates the values of characteristics based on data on the first visit of clinical subjects belonging to each clinical group. When data on the first visit of each clinical subject was missing, the data on the first visit of the corresponding clinical subject was substituted with data on the third visit to proceed with an analysis. In FIG. 13, Visit 2 indicates the values of characteristics based on data on the second visit of clinical subjects belonging to each clinical group.

In FIG. 13, it can be seen that the level of thyroid hormone (free T4) of the hypothyroidism group measured at the second visit fell below the normal range (0.8-1.8 ng/dL) compared to that of the first visit and the clinical subjects belonging to the clinical group have hypothyroidism at the second visit. In FIG. 13, it can be seen that the levels of thyroid hormone (free T4) of the control group measured at the first and second visits fell within the normal range (0.8-1.8 ng/dL) and the clinical subjects belonging to the clinical group have a normal thyroid function at the first and second visits. In FIG. 13, the levels of thyroid hormone (free T4) of the control group were within the normal range at Visit 1 or 3 and Visit 2, but the level of free T4 thyroid hormone at the second visit was statistically significantly decreased compared to that of the first visit. On-site rHR did not reflect the difference in the significantly decreased level of thyroid hormone (free T4) of the control group, but parameters measured by a wearable device (i.e., WD-rHR, WD-sleepHR, and WD-2to6HR) may be a relatively more sensitive indicator that reflects the difference in the significantly decreased level of thyroid hormone (free T4) of the control group.

FIG. 14 is a diagram showing a result of analyzing the association between the concentration of free T4 thyroid hormone and a heart rate parameter on the basis of the changes in thyroid function parameters shown in FIG. 13. In FIG. 14, "Unstandardized beta of On-site rHR" is the association between a free T4 thyroid hormone concentration and a resting heart rate measured after 15 minutes of rest at the time of a hospital visit, "Unstandardized beta of WD-rHR" is the association between a free T4 thyroid hormone concentration and the average of resting heart rates measured by a wearable device for a period of five days before a hospital visit, "Unstandardized beta of WD-sleepHR" is the association between a free T4 thyroid hormone concentration and the average of sleeping heart rates measured by a wearable device for a period of five days before a hospital visit, and "Unstandardized beta of WD-2to6HR" is the association between a free T4 thyroid hormone concentration and the average of heart rates measured by a wearable device from 2:00 AM to 6:00 AM for a period of five days before a hospital visit.

In FIG. 14, it was confirmed that the associations between the free T4 thyroid hormone concentration and some parameters calculated using the heart rate acquired by the wearable device were greater than the association between the free T4 thyroid hormone concentration and the resting heart rate at the hospital visit.

FIG. 15 is a diagram showing a result of analyzing the associations between hypothyroidism and heart rate parameters on the basis of the changes in thyroid function parameters shown in FIG. 13. Here, hypothyroidism may refer to a result of a doctor's diagnosis of thyroid dysfunction through hormone levels measured at the time of a hospital visit. In FIG. 15, "Unstandardized beta of On-site rHR" is the association between a hypothyroidism diagnosis and a resting heart rate measured after 15 minutes of rest at the time of a hospital visit, "Unstandardized beta of WD-rHR" is the association between a hypothyroidism diagnosis and the average of resting heart rates measured by a wearable device for a period of five days before a hospital visit, "Unstandardized beta of WD-sleepHR" is the association between a hypothyroidism diagnosis and the average of sleeping heart rates measured by a wearable device for a period of five days before a hospital visit, and "Unstandardized beta of WD-2to6HR" is the association between a hypothyroidism diagnosis and the average of heart rates measured by a wearable device from 2:00 AM to 6:00 AM for a period of five days before a hospital visit.

In FIG. 15, it was confirmed that the associations between the hypothyroidism diagnosis and some parameters calculated using the heart rate acquired by the wearable device were greater than the association between the hypothyroidism diagnosis and the resting heart rate at the hospital visit.

In FIGS. 14 and 15, it was confirmed that the associations between hypothyroidism and parameters calculated using the heart rate acquired by the wearable device were greater than the association between hypothyroidism and the resting heart rate at the hospital visit. According to the characteristics of the wearable device, by predicting thyroid dysfunction on the basis of heart rate information acquired through the wearable device, thyroid dysfunction is predicted not based on "short-term" heart rate information at the time of a hospital visit but based on relatively "long-term" heart rate information acquired during daily life, and thus it is determined that relatively accurate predictions are possible.

Figure 16:
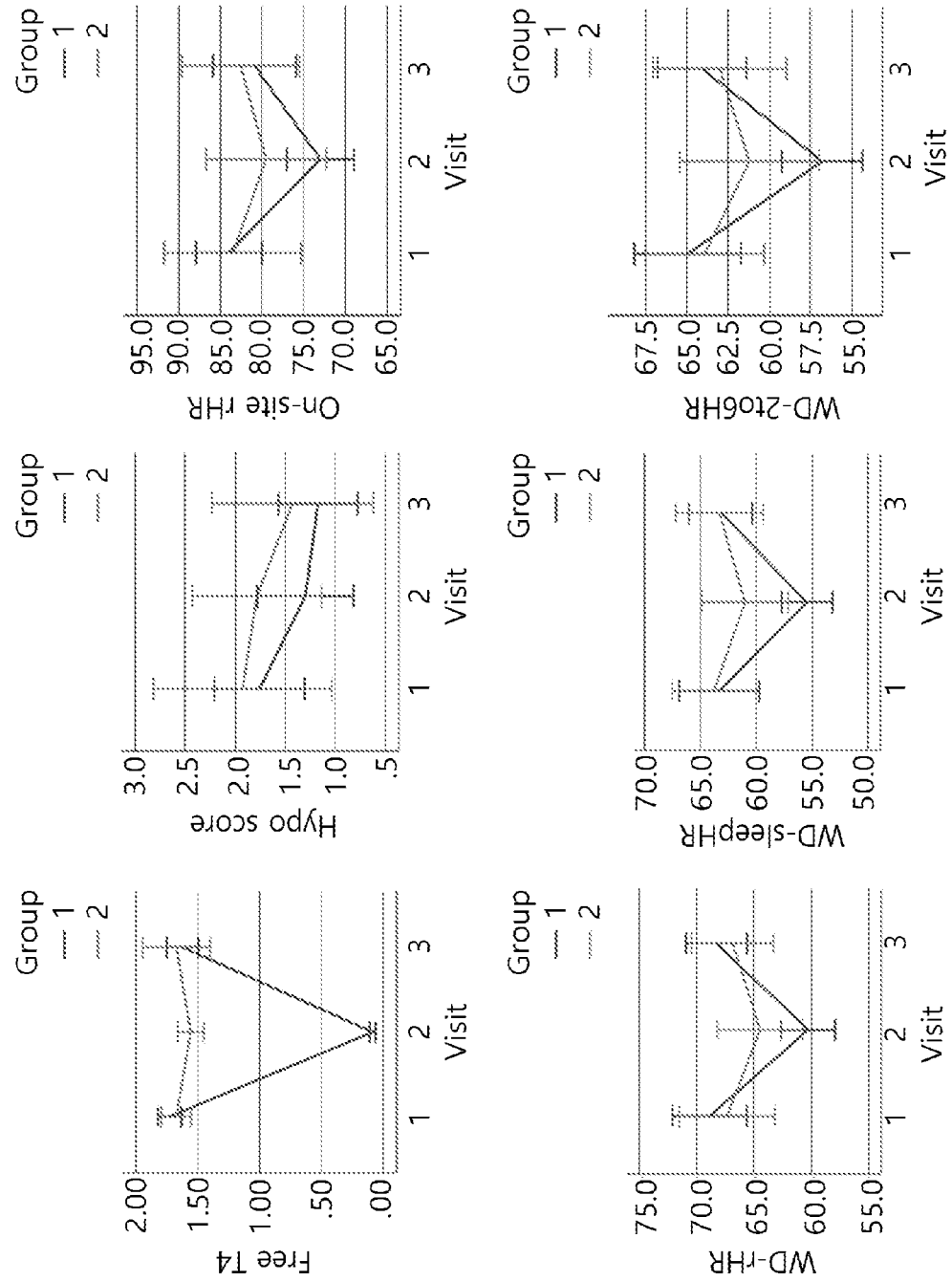
FIG. 16 is a diagram showing the change in average free T4 according to the hospital visit, the change in hypothyroidism symptom score according to the hospital visit, the change in on-site HR according to the hospital visit, the change in WD-rHR according to the hospital visit, the change in WD-sleepHR according to the hospital visit, and the change in WD-2to6HR according to the hospital visit.

FIG. 16 is a diagram showing the change in average free T4 according to the hospital visit, the change in hypothyroidism symptom score according to the hospital visit, the change in on-site HR according to the hospital visit, the change in WD-rHR according to the hospital visit, the change in WD-sleepHR according to the hospital visit, and the change in WD-2to6HR according to the hospital visit on the basis of the changes in thyroid function parameters, which are shown in FIG. 3, for each hospital visit (from the upper left corner to the right, 95% CI error bars). In FIG. 16, "On-site Rhr" is a resting heart rate measured in a conventional method after 15 minutes of rest at the time of a hospital visit, "WD-rHR" is the average of resting heart rates measured by a wearable device during a period of five days before a hospital visit, "WD-sleepHR" is the average of sleeping heart rates measured by a wearable device for a period of five days before a hospital visit, and "WD-2to6HR" is the average of heart rates measured by a wearable device from 2:00 AM to 6:00 AM for a period of five days before a hospital visit. Among the heart rate-related parameters acquired in FIG. 16, WD-rHR, WD-sleepHR, and WD-2to6HR were calculated based on biometric information and/or time, motion, and sleep information acquired using a wearable device.

In FIG. 16, the change in symptom score according to the time of a hospital visit showed that the error bar of the hypothyroidism group overlapped the average of the control group and thus it was actually difficult to use the "symptom score" as a single indicator to distinguish between hypothyroidism and normal levels. On the other hand, in FIG. 16, the heart rate-related parameters On-site rHR, WD-rHR, WD-sleepHR, and WD-2to6HR according to the time of a hospital visit showed that the error bar of the hypothyroidism group is located below and is also significantly different from the average of the control group and thus the heart rate-related parameters On-site rHR, WD-rHR, WD-sleepHR, or WD-2to6HR can be used as a single indicator to distinguish between hypothyroidism and normal levels.

As a result, it has been demonstrated that heart rate-based parameters measured by a wearable device can be used as an indicator for predicting hypothyroidism and shows stronger predictive power than the conventionally used symptom score. Also, the "association between a heart rate measured by a wearable device and the prevalence or recurrence of hypothyroidism" which are confirmed based on this clinical study shows that it is possible to evaluate the degree of control of hyperthyroidism from changes in resting heart rate and to predict recurrence easily even if a patient only wears a wearable device without visiting a hospital by using a monitoring system according to an embodiment of the present application.

The contents of a clinical study on the correlation between hypothyroidism and a heart rate have not been described herein as a basis for the monitoring system according to an embodiment of the present application to predict thyroid dysfunction. This is disclosed in Korean Patent No. 10-2033696 so that even if a redundant description is not provided herein, those skilled in the art can fully understand that hyperthyroidism can be predicted based on heart rate information using a wearable device.

1.1.5 Period of Thyroid Dysfunction Monitoring S100

According to an embodiment of the present invention, the thyroid function monitoring method S100 according to an embodiment of the present application may include biometric information acquisition S1100, monitoring data calculation S1300, and thyroid dysfunction determination S1500.

The biometric information acquisition S1100 may be performed at first intervals. The interval of the biometric information acquisition S1100 may be determined according to the data transmission interval of the user terminal 2000. The interval of the biometric information acquisition S1100 may be determined according to the biometric information transmission interval of the user terminal 2000. The biometric information acquisition S1100 may be performed at predetermined intervals (i.e., the previous first interval).

The interval at which the monitoring server 3000 acquires biometric information from the user terminal 2000 (S1100) (i.e., the previous first interval) may be different from an interval at which the wearable device 1000 acquires biometric information. The interval at which the monitoring server 3000 acquires biometric information from the user terminal 2000 (S1100) may be longer than or equal to the interval at which the wearable device 1000 acquires biometric information. Since this has already been described above, a redundant description thereof will be omitted.

The monitoring data calculation S1300 may be performed at second intervals. The monitoring data calculation S1300 may be performed using the biometric information acquisition S1100 as a trigger. The monitoring data calculation S1300 may be performed at intervals preset in the monitoring server 3000 (i.e., the previous second interval). Alternatively, the monitoring data calculation S1300 may be performed when a signal for performing operation S1300 is received from an external device (e.g., the user terminal 2000).

The interval at which the monitoring server 3000 calculates the monitoring data (i.e., the previous second interval) (S1300) may be different from the interval at which the monitoring server 3000 acquires the biometric information (i.e., the previous first interval) (S1100). The interval at which the monitoring server 3000 calculates the monitoring data (i.e., the previous second interval) (S1300) may be longer than or equal to the interval at which the monitoring server 3000 acquires the biometric information (i.e., the previous first interval) (S1100).

The thyroid dysfunction determination S1500 may be performed at third intervals. The thyroid dysfunction determination (S1300) may be performed using the monitoring data calculation S1300 as a trigger. The thyroid dysfunction determination S1500 may be performed at intervals preset in the monitoring server 3000 (i.e., the previous third interval).

The interval at which the monitoring server 3000 determines thyroid dysfunction (i.e., the previous third interval) (S1500) may be different from the interval at which the monitoring server 3000 calculates the monitoring data (i.e., the previous second interval) (S1300). The interval at which the monitoring server 3000 determines thyroid dysfunction (i.e., the previous third interval) (S1500) may be longer than or equal to the interval at which the monitoring server 3000 calculates the monitoring data (i.e., the previous second interval) (S1300).

Figure 17:
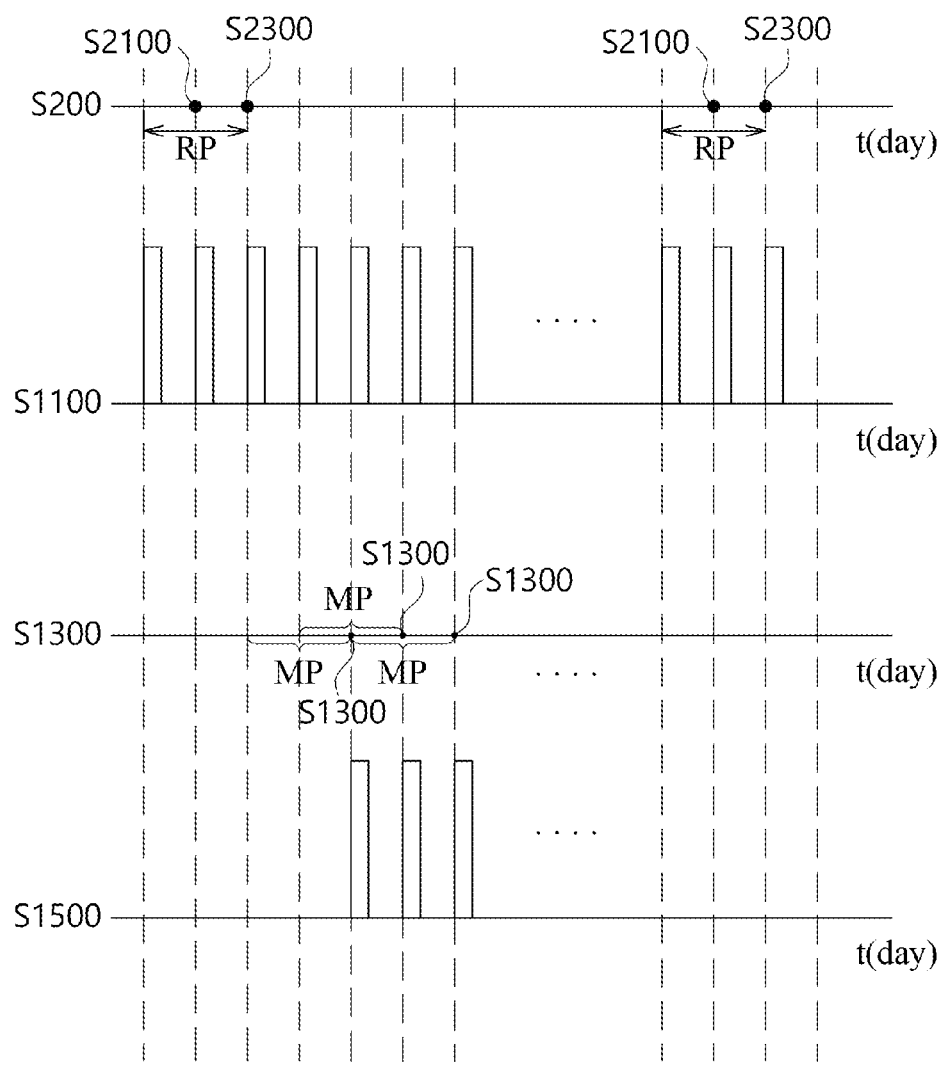
FIG. 17 is a diagram illustrating an operation timing of a thyroid dysfunction monitoring method according to an embodiment of the present application.

FIG. 17 is a diagram illustrating an operation timing of a thyroid dysfunction monitoring method S100 according to an embodiment of the present application.

According to an embodiment of the present application, reference data may be calculated by using reception of thyroid state information as a trigger. The biometric information may be acquired at first intervals. The monitoring data may be calculated at second intervals. The thyroid dysfunction determination may be performed in response to calculation of monitoring data.

Referring to FIG. 12, when the thyroid state information is received by the monitoring server 3000 (S2100), reference data for a reference data calculation period RP may be calculated (S2300).

The reference data may be calculated based on biometric information for at least one resting period included in the reference data calculation period RP. The reference data may be calculated based on a heart rate for at least one resting period included in the reference data calculation period RP. When reference data is calculated according to the reference data calculation method described herein and biometric information used for the calculation includes a heart rate, the reference data may be disclosed as a reference heart rate.

As an example, after a resting period is extracted during a period including a date at which the user's thyroid hormone level is in the normal range, the reference heart rate may be determined based on a heart rate during the resting period.

As another example, after a resting period is extracted during a period including a date at which the user's thyroid hormone level is outside the normal range, the reference heart rate may be determined using estimated data for reference period data determined based on a heart rate during the resting period.

As another example, when the user's thyroid hormone level is not present, the reference heart rate may be calculated based on the user's heart rate for a plurality of consecutive days.

The reference data calculation period RP may also include a period before the thyroid state information is received (S2100). As an example, the reference data calculation period RP may be determined as a total of five days, including two days before and two days after the date at which the thyroid state information is received (S2100).

The monitoring server 3000 may acquire biometric information at first intervals (S1100). The period in which the biometric information is acquired (S1100) may include a period overlapping the reference data calculation period RP. The period in which the biometric information is acquired (S1100) may overlap the period in which the monitoring data is calculated (S1300).

The biometric information acquired at first intervals may be stored in the monitoring server 3000. The biometric information acquired at first intervals may be stored in the monitoring server 3000 for a predetermined period.

The monitoring server 3000 may calculate monitoring data at second intervals (S1300). The monitoring server 3000 may calculate monitoring data for a monitoring period MP at second intervals (S1300).

The monitoring data may be calculated based on biometric information for at least one resting period included in the monitoring period MP. The monitoring data may be calculated based on a heart rate for at least one resting period included in the monitoring period MP. When monitoring data is calculated according to the monitoring data calculation method described herein and biometric information used for the calculation includes a heart rate, the monitoring data may be disclosed as a monitoring heart rate.

As an example, after a resting period of the monitoring period is extracted, the monitoring heart rate may be determined based on a heart rate of the resting period. The resting period may be chosen based on information on the user's exercise state. The resting period may be chosen based on a period in which the user's step count is zero for a predetermined time or longer. The resting period may be chosen based on a period in which the user's acceleration is zero for a predetermined timer or longer.

As another example, after a sleeping period of the monitoring period is extracted, the monitoring heart rate may be determined based on a heart rate of the sleeping period. The sleeping period may be chosen based on information on the user's exercise state. Alternatively, the sleeping period may be selected based on information on breathing, information on noise, biometric information other than a heart rate, etc. through the device sensor unit 1400.

The monitoring server 3000 may calculate first monitoring data for a first monitoring period MP at a first time point. The monitoring server 3000 may calculate second monitoring data for a second monitoring period MP at a second time point when a second period has elapsed from the first time point.

The first monitoring period MP and the second monitoring period MP may include an overlapping period. The first monitoring period MP and the second monitoring period MP may have the same length. In other words, when the first monitoring period MP is five days, the second monitoring period MP may be five days.

Although not essential, the reference data calculation period RP and the monitoring period MP may have the same length. In other words, when the reference data calculation period RP is five days, the monitoring period MP may be five days.

According to an embodiment of the present application, the period in which the monitoring server 3000 calculates the monitoring data (S1300) may be longer than the period in which the monitoring server 3000 acquires the biometric information (S1100). As a specific example, the monitoring server 3000 may acquire biometric information every three hours and may calculate monitoring data every day.

The time point at which the monitoring data is calculated (S1300) may be close to the end point of the monitoring period MP of the monitoring data. The time point at which the monitoring data is calculated (S1300) may be the same as the end point of the monitoring period MP of the monitoring data. The time point at which the monitoring data is calculated (S1300) may be substantially the same as the end point of the monitoring period MP of the monitoring data.

The monitoring server 3000 may perform thyroid dysfunction determination S1500 at third intervals. When the monitoring data is calculated (S1300), the monitoring server 3000 may perform thyroid dysfunction determination S1500.

When the monitoring data is calculated (S1300), the monitoring server 3000 may compare the monitoring data to reference data (S1510). When a result of comparing the monitoring data to the reference data satisfies a predetermined criterion, the monitoring server 3000 may determine that the thyroid function is abnormal (S1530) and perform an appropriate operation for outputting an alert.

The number of instances of performing operation S1510 may be greater than or equal to the number of instances of performing operation S1530.

The period in which the monitoring server 3000 calculates the reference data (S200) may be longer than the period in which the monitoring server 3000 monitors the monitoring data (S1300).

The reference data according to an embodiment of the present application may be stored in the server database 3200 of the monitoring server 3000 before the monitoring data is calculated (S1300). The monitoring server 3000 may confirm reference data stored when the monitoring data is calculated (S1300) and when thyroid dysfunction is determined (S1500). Accordingly, until a new event is generated and the reference data is updated, the reference data value stored in the server database 3200 may be maintained. When the thyroid state information is received, the monitoring server 3000 may calculate reference data (S200) and store the new reference data in the server database 3200.

When the reference data is calculated (S200), thyroid dysfunction determination using the corresponding reference data (S1500) may be performed multiple times. Until the reference data is calculated (S200) and another event is generated, thyroid dysfunction monitoring S100 may be performed multiple times.

According to an embodiment of the present application, the time point at which the reference data is calculated (S2300) and the time point at which the thyroid dysfunction is determined (S1500) may not overlap each other. The reference data calculation period RP and the monitoring period MP may not overlap each other.

According to an embodiment of the present application, first reference data for a first reference data calculation period RP calculated in response to the reception of the thyroid state information (S2100) may be calculated (S2300). Second reference data for a second reference data calculation period RP calculated in response to the reception of new thyroid state information (S2100) may be calculated (S2300).

Here, the first reference data calculation period RP and the second reference data calculation period RP may not overlap each other. Alternatively, the first reference data calculation period RP may be included in the second reference data calculation period RP.

2. User Interface of Thyroid Dysfunction Monitoring System 100

Figure 18:
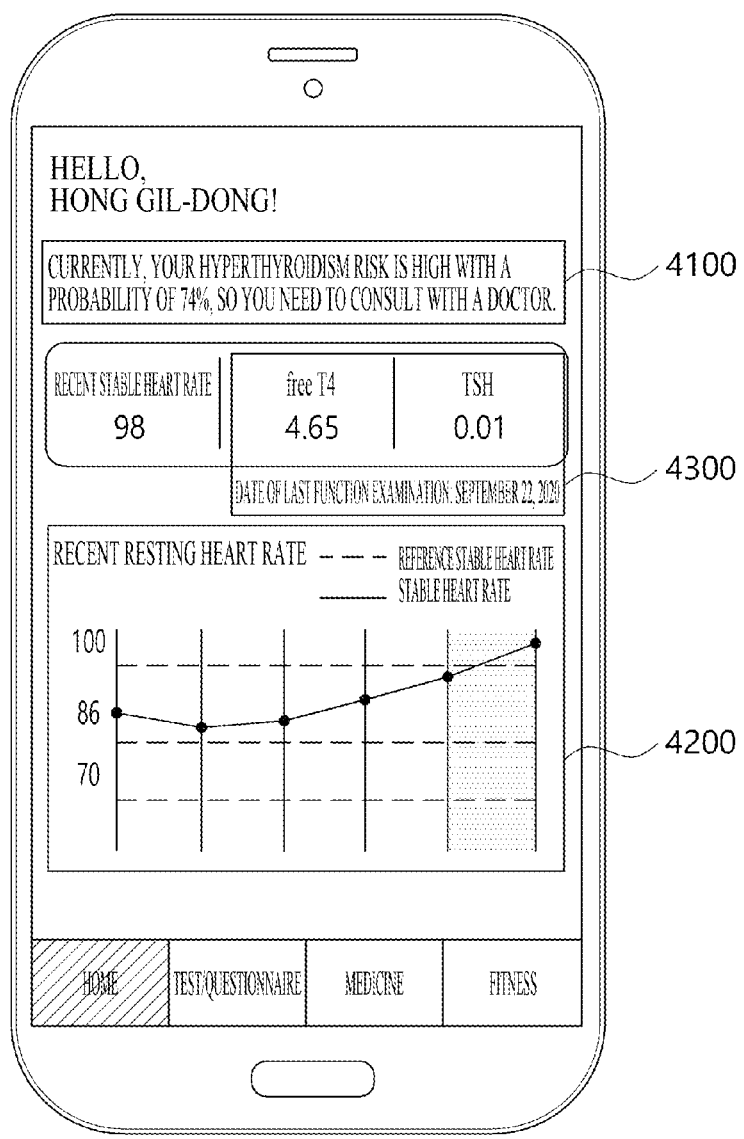
FIGS. 18 and 19 are diagrams illustrating a user interface in a thyroid dysfunction monitoring system according to an embodiment of the present application.
Figure 19:
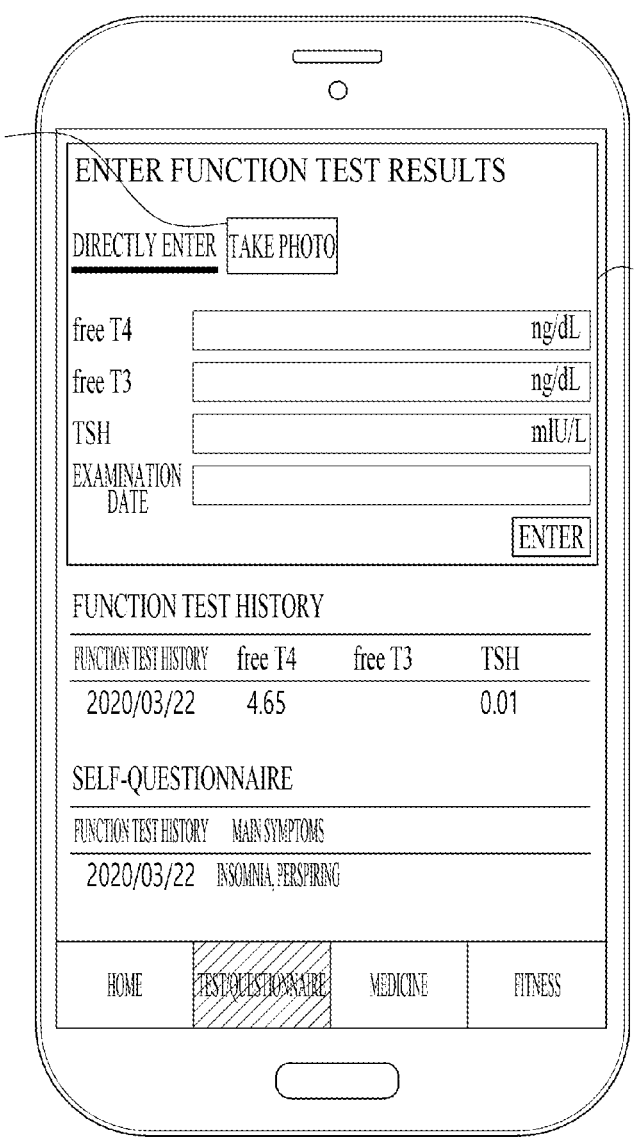

FIGS. 18 and 19 are diagrams illustrating a user interface 400 in a thyroid dysfunction monitoring system 100 according to an embodiment of the present application.

According to an embodiment of the present application, the user terminal 2000 may output a result corresponding to the thyroid dysfunction monitoring S100. According to an embodiment of the present application, the user terminal 2000 may output a result corresponding to the thyroid dysfunction determination S1500. According to an embodiment of the present application, the user terminal 2000 may output a result corresponding to the thyroid dysfunction determination S1530.

The terminal output unit 2200 of the user terminal 2000 may output appropriate information to a user on the basis of information received from the monitoring server 3000.

Referring to FIG. 18, the user terminal 2000 may output a user interface 400 including a thyroid information interface 4100, a heart rate information interface 4200, and a hormone information interface 4300.

Through the thyroid information interface 4100, information based on the thyroid dysfunction determination S1500 may be output. As an example, through the thyroid information interface 4100, information on the risk of thyroid dysfunction may be output. As a specific example, through the thyroid information interface 4100, information indicating that the risk of thyroid dysfunction is high, i.e., 74%, may be output. Through the thyroid information interface 4100, information for driving hospital visits may be further output. As a specific example, through the thyroid information interface 4100, a message instructing to consult with a doctor because the risk of hyperthyroidism is high may be output. As a specific example, through the thyroid information interface 4100, a questionnaire for self-diagnosis may be output.

The "alert" described herein may include providing information to a user on the basis of the thyroid dysfunction determination S1500. The "alert" described herein may include providing information to a user on the basis of the thyroid dysfunction determination S1500 in a visual, auditory, tactile, olfactory, and/or gustatory manner.

Through the heart rate information interface 4200, information based on the monitoring data calculation S1300 may be output. As an example, through the heart rate information interface 4200, monitoring heart rate information may be output. As a specific example, through the heart rate information interface 4200, monitoring heart rate information may be output such that its change pattern is expressed over time.

Through the heart rate information interface 4200, information based on the reference data calculation S200 may also be output. As an example, through the heart rate information interface 4200, reference heart rate information may be output. As a specific example, through the heart rate information interface 4200, the reference heart rate information, first threshold heart rate information, which will be a criterion for determining thyroid dysfunction that is greater than the reference heart rate by a first threshold, and second threshold heart rate information, which will be a criterion for determining thyroid dysfunction that is smaller than the reference heart rate by a second threshold, may also be output.

Through the heart rate information interface 4200, other information may be output in addition to the monitoring heart rate information. As a specific example, through the heart rate information interface 4200, monitoring heart rate information and a hormone level corresponding to a user's blood test may be output such that their change patterns are expressed over time.

Through the hormone information interface 4300, a hormone level corresponding to a user's blood test which is input through the terminal input unit 2100 may be output. As an example, through the hormone information interface 4300, a hormone level corresponding to a user's blood test, which is most recently input, may be output. As a specific example, through the hormone information interface 4300, free T4 and TSH hormone levels corresponding to a user's blood test, which are most recently input, may be output.

Through the hormone information interface 4300, the date of the user's blood test may also be output. Through the hormone information interface 4300, the number of days that have passed from the date of the user's most recent blood test may also be output.

Referring to FIG. 19, the user terminal 2000 may output a user interface 400 including a test information input interface 4400.

Through the test information input interface 4400, an interface for inputting a user's blood test result may be output. As an example, through the test information input interface 4400, separate interfaces may be output such that the user's blood test result can be input for each hormone.

The test information input interface 4400 may further include a photo input interface 4420. When the photo input interface 4420 is clicked, the user terminal 2000 may provide an interface for imaging the user's test result sheet. When the user's test result sheet is imaged, the user terminal 2000 may confirm the user's hormone information by performing an optical character reader (OCR) operation.

The user interface 400 may further include a self-examination input interface for receiving a user's symptom information. Symptom information such as insomnia, headache, hand tremor, and reduced concentration may be input through the self-examination input interface.

3. Modified Embodiment of Thyroid Dysfunction Monitoring System 100

According to an embodiment of the present application, the thyroid dysfunction monitoring system 100 may predict a user's thyroid dysfunction on the basis of a biometric signal. The thyroid dysfunction monitoring system 100 may predict a user's thyroid dysfunction by monitoring the user's heart rate information.

When the user's thyroid dysfunction is predicted by the thyroid dysfunction monitoring system 100, it is necessary to distinguish thyroid diseases from other diseases in which similar symptoms (i.e., similar bio-signals) are expressed in order to more accurately determine the thyroid function. For example, when the thyroid dysfunction monitoring system 100 predicts a user's thyroid function based on the user's heart rate information, it is important to distinguish thyroid diseases from atrial fibrillation, in which a heart rate is significantly higher than usual.

To this end, the thyroid dysfunction monitoring system 100 may predict thyroid dysfunction in further comparison to a second factor different from a heart rate. A modified embodiment of the thyroid dysfunction monitoring system 100 for more accurately predicting a user's thyroid dysfunction will be disclosed in detail below.

According to a thyroid dysfunction monitoring method which will be described below, it is possible to provide more accurate thyroid dysfunction monitoring even for a user who has never had hyperthyroidism or hypothyroidism or who has a small genetic factor.

Figure 20:
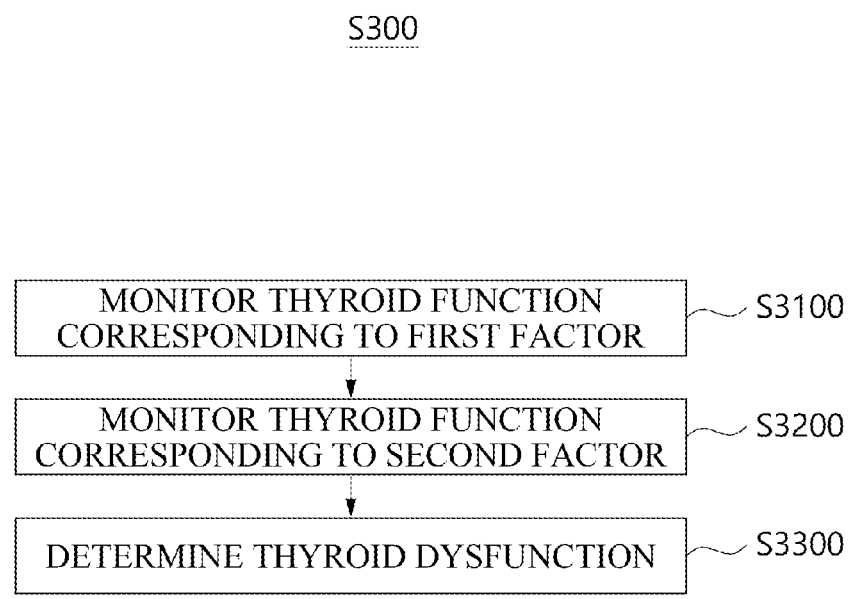
FIG. 20 is a flowchart illustrating thyroid dysfunction monitoring according to an embodiment of the present application.

FIG. 20 is a flowchart illustrating thyroid dysfunction monitoring S300 according to an embodiment of the present application.

Referring to FIG. 20, the thyroid dysfunction monitoring method S300 according to the present application may include first-factor-based thyroid function monitoring S3100, second-factor-based thyroid function monitoring S3200, and thyroid dysfunction determination S3300. According to an embodiment, the operations S3100, S3200, and S3300 may be performed by the monitoring server 3000.

The first-factor-based thyroid function monitoring S3100 may be performed similarly to the above-described thyroid dysfunction monitoring S100. As an example, the first-factor-based thyroid function monitoring S3100 may be performed similarly to the above-described thyroid dysfunction monitoring S100 method of obtaining acquiring heart rate information (S1100), calculating a monitoring heart rate (S1300) and determining thyroid dysfunction (S1500) through comparison to a reference heart rate.

Therefore, a redundant description of the first-factor-based thyroid function monitoring S3100 will be omitted.

The second-factor-based thyroid function monitoring S3200 may be performed by analyzing PPG data acquired through the device sensor unit 1400. As an example, the acquired PPG data may be data acquired to extract a heart rate used for the first-factor-based thyroid function monitoring S3100.

Figure 21:
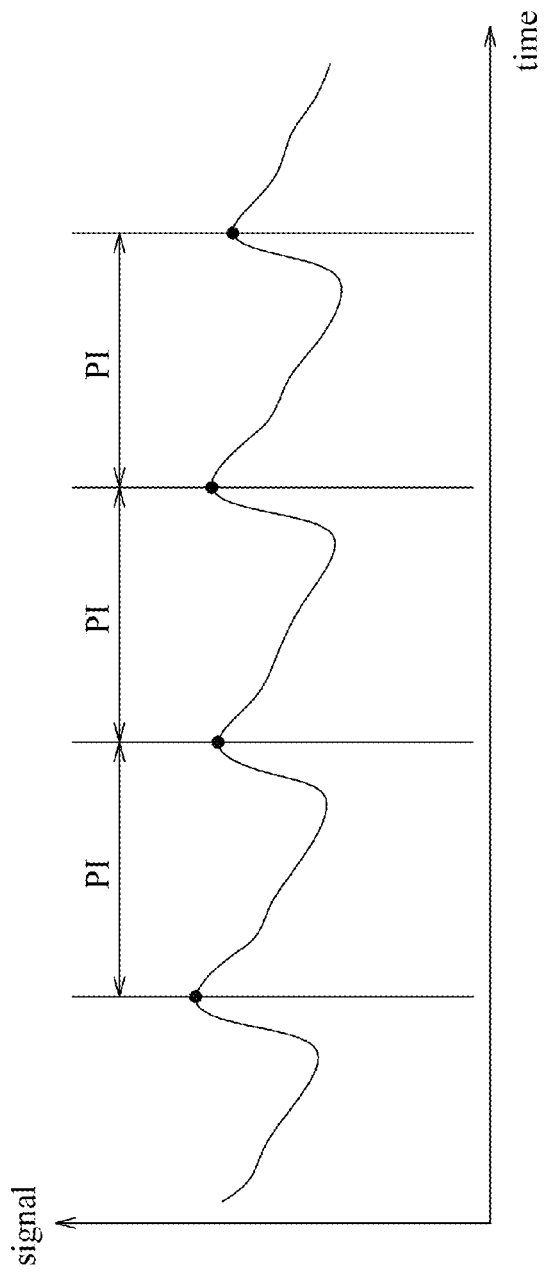
FIG. 21 is a diagram illustrating the analysis of photoplethysmogram (PPG) data acquired through a wearable device and PPG data performed through a monitoring server.

FIG. 21 is a diagram illustrating the analysis of PPG data acquired through a wearable device 1000 and PPG data performed through a monitoring server 3000.

The monitoring server 3000 may receive PPG data acquired through the device sensor unit 1400 of the wearable device 1000. The server communication unit 3100 may receive the acquired PPG data from the user terminal 2000 and/or the wearable device 1000. The wearable device 1000 may transmit the acquired PPG data to the user terminal 2000, and the user terminal 2000 may transmit the received PPG data to the monitoring server 3000. Through the user terminal 2000, the monitoring server 3000 may receive PPG data acquired through the device sensor unit 1400.

Referring to FIG. 21, the monitoring server 3000 may confirm a peak interval PI on the basis of the PPG data. The monitoring server 3000 may confirm a peak interval PI, which is a time interval between a point where a PPG peak is confirmed and a point where a subsequent PPG peak is confirmed, of the PPG data. The monitoring server 3000 may confirm a change in peak interval PI on the basis of the PPG data.

In the case of thyroid dysfunction, a heart rate tends to steadily increase or decrease for a long time, but in the case of atrial fibrillation, irregular heartbeats tend to repeat while many parts of an atrial muscle contract irregularly and uncontrollably at the same time. Thus, by classifying the peak interval PI of PPG data, it is possible to improve the accuracy of thyroid dysfunction determination.

According to an embodiment of the present application, the monitoring server 3000 may confirm the peak interval PI of the PPG data in operation S3200 and may determine that the risk of atrial fibrillation is higher than the risk of thyroid dysfunction when the peak interval PI changes significantly over time. As an example, when it is determined that there is a thyroid dysfunction in operation S3100, the monitoring server 3000 may confirm the peak interval PI of the PPG data in operation S3200 and may determine that the risk of atrial fibrillation is high when the peak interval PI changes significantly over time (S3300). The operations S3200 and S3300 may be performed by the server control unit 3300.

The monitoring server 3000 may confirm the peak interval PI of the PPG data in operation S3200 and may determine that the risk of thyroid dysfunction is higher than the risk of atrial fibrillation when the peak interval PI remains nearly constant. As an example, when it is determined that there is a thyroid dysfunction in operation S3100, the monitoring server 3000 may confirm the peak interval PI of the PPG data in operation S3200 and may determine that the risk of thyroid dysfunction is high when the peak interval PI remains nearly constant independent of changes over time (S3300).

When the thyroid dysfunction monitoring S300 according to the present embodiment is performed, an advantage of more accurately predicting thyroid dysfunction without additional hardware may be derived.

Continuing from FIG. 20, the second-factor-based thyroid function monitoring S3200 may be performed by analyzing biometric information acquired through the device sensor unit 1400 in addition to heart rate information. As an example, the wearable device 1000 may acquire a user's temperature information. The device sensor unit 1400 may sense a user's temperature, and the device communication unit 1300 may transmit temperature information to the monitoring server 3000.

The monitoring server 3000 may calculate a reference temperature and a monitoring temperature. The reference temperature may be acquired similarly to the method in which the reference data is acquired in the above-described operation S2300. The monitoring temperature may be acquired similarly to the method in which the monitoring data is acquired in the above-described operation S1300.

The monitoring server 3000 may perform thyroid function monitoring S3200 by comparing the reference temperature and the monitoring temperature.

According to an embodiment of the present application, the monitoring server 3000 may determine a user's thyroid dysfunction on the basis of the user's heart rate information and temperature information. The monitoring server 3000 may perform the user's thyroid function monitoring corresponding to the heart rate information and the user's function monitoring corresponding to the temperature information in parallel. In other words, the monitoring server 3000 may calculate the monitoring temperature information and the monitoring heart rate for the monitoring period, compare the monitoring heart rate and the reference heart rate, compare the monitoring temperature and the reference temperature, and perform the user's thyroid dysfunction determination S3300 on the basis of the two comparison result values.

According to another embodiment of the present application, the monitoring server 3000 may perform the user's thyroid function monitoring corresponding to the heart rate information and the user's function monitoring corresponding to the temperature information in sequence. In other words, when thyroid dysfunction is determined by comparing the monitoring heart rate and the reference heart rate (S3100), the monitoring server 3000 may perform the user's thyroid dysfunction determination S3200 based on the two result values to perform the user's final thyroid dysfunction determination S3300 by comparing the monitoring temperature and the reference temperature. When it is determined that there is no thyroid dysfunction by comparing the monitoring heart rate and the reference heart rate (S3100), the thyroid function monitoring S3200 in which the monitoring temperature and the reference temperature are compared may not be performed.

According to an embodiment of the present application, a reference period in which the reference heart rate is calculated and a reference period in which the reference temperature is calculated may overlap each other. If necessary, the reference period in which the reference heart rate is calculated may be the same as the reference period in which the reference temperature is calculated. If necessary, a monitoring period in which the monitoring heart rate is calculated and a monitoring period in which the monitoring temperature is calculated may overlap each other. If necessary, the monitoring period in which the monitoring heart rate is calculated may be longer than the monitoring period in which the monitoring temperature is calculated.

Continuing from FIG. 20, the second-factor-based thyroid function monitoring S3200 may be performed by requesting additional biometric information through the device sensor unit 1400. As an example, when, through the result according to operation S3100, it is determined that there is a possibility of thyroid dysfunction, the monitoring server 3000 may request transmission of additional ECG waveform data, analyze the corresponding data, and perform second-factor-based thyroid function monitoring S3200.

Figure 22:
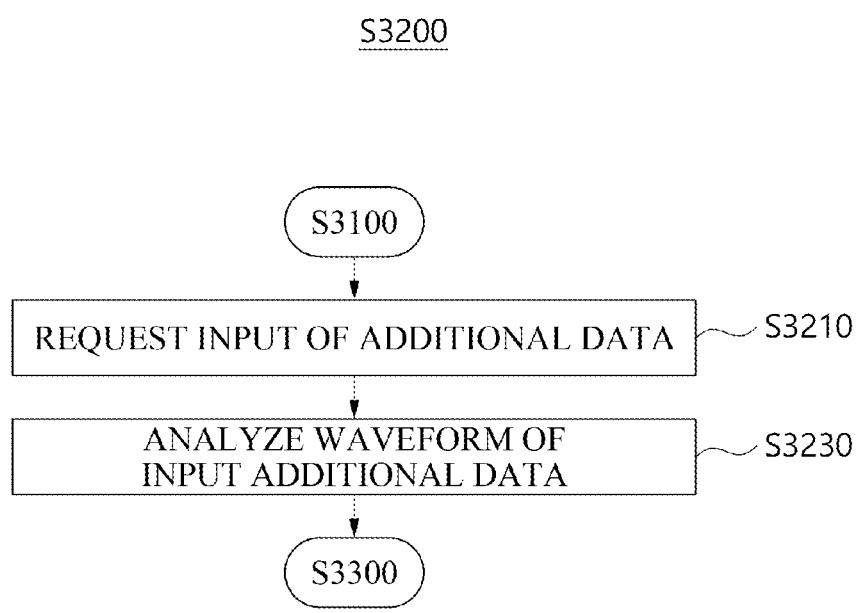
FIG. 22 is a flowchart illustrating second-factor-based thyroid function monitoring according to an embodiment of the present application.

FIG. 22 is a flowchart illustrating second-factor-based thyroid function monitoring S3200 according to an embodiment of the present application.

When it is determined that there is a possibility that a user's thyroid function is abnormal through the first-factor-based thyroid function monitoring S3100, the monitoring server 3000 may request input of additional data (S3210). In order to receive additional data, the monitoring server 3000 may transmit a request for the additional data to the user terminal 2000. Operation S3210 may be an operation that the server control unit 3300 performs through the server communication unit 3100.

As an example, the user terminal 2000 may request additional data from the wearable device 1000 in response to the request of the monitoring server 3000. The wearable device 1000 may output, to a user, a notification requesting input of additional data through the device output unit 1200 in response to the request of the user terminal 2000. As another example, the user terminal 2000 may output, to a user, a notification requesting input of additional data through the wearable device 1000, through the terminal output unit 2200.

When the additional data is ECG data, the user may need to connect both hands to at least two electrodes formed in the wearable device 1000.

Figure 23:
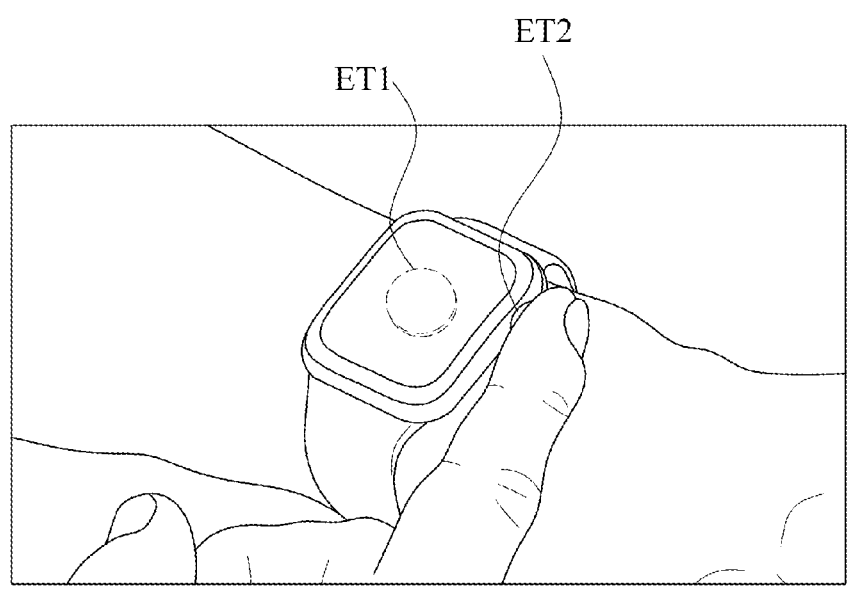
FIG. 23 is a conceptual diagram illustrating an electrocardiogram (ECG) data acquisition method using a wearable device according to an embodiment of the present application.

FIG. 23 is a conceptual diagram illustrating an ECG data acquisition method using a wearable device 1000 according to an embodiment of the present application.

In order to acquire ECG data through the wearable device 1000, it may be required to form a physical electrical closed loop based on both of the electrodes by bringing the left or right hand into contact with a first electrode ET1 and bringing the other hand into contact with a second electrode ET2.

In the wearable device 1000 shown in FIG. 23, the first electrode ET1 is formed on the rear surface of the display brought into contact with the wrist, and the second electrode ET2 is formed on a scroll for adjusting the display or the like.

In this case, when the left hand is brought into contact with the first electrode ET1 in a form in which the first electrode ET1 is formed on the wrist of the left hand and a right finger is brought into contact with the second electrode ET2, it is possible to perform ECG sensing through the wearable device 1000.

Continuing from FIG. 22, in response to an input request for additional data by the monitoring server 3000 (S3210), a user may be induced to bring his or her right finger into contact with the second electrode ET2. When the additional data is input by the user's specific operation, the wearable device 1000 may transmit the acquired additional data to the monitoring server 3000 through the user terminal 2000.

The monitoring server 3000 may analyze the waveform of the input additional data (S3230). As an example of analyzing the waveform of the additional data, it is possible to check whether the P wave can be distinguished.

Figure 24A:
FIGS. 24A and 24B are diagrams illustrating an ECG data waveform analysis method according to an embodiment of the present application.
Figure 24B:
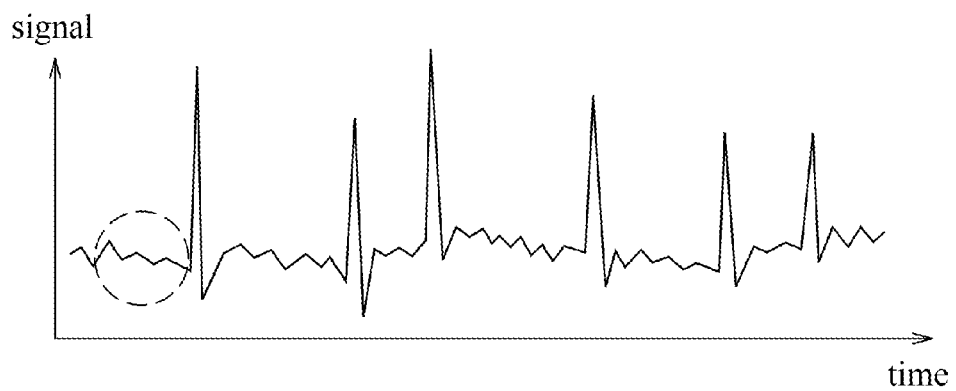

FIGS. 24A and 24B are diagrams illustrating a method for ECG data waveform analysis S3230 according to an embodiment of the present application.

When a user exhibits symptoms of atrial fibrillation, the user may not be able to accurately distinguish the P wave from among the PQRS waves. Referring to FIG. 24A, the PQRS waves are all clearly shown in the ECG data of a person distinguished as a normal person. However, referring to FIG. 24B, in the ECG data of a person distinguished as having atrial fibrillation, values other than the maximum peak value are not accurately distinguished, and in particular, the P wave is not distinguished.

Continuing from FIG. 22, the monitoring server 3000 may analyze the waveform of the input additional data (S3230). When it is determined that the user's P wave is not significantly distinguished, the monitoring server 3000 may determine that the risk of atrial fibrillation is greater than the risk of thyroid dysfunction (S3300).

The monitoring server 3000 may analyze the waveform of the input additional data (S3230). When it is determined that the user's P wave is well distinguished, the monitoring server 3000 may determine that the risk of thyroid dysfunction is greater than the risk of atrial fibrillation (S3300).

4. Thyroid Dysfunction Monitoring Considering Medication (S400)

In the case of patients with thyroid dysfunction, most of them are undergoing therapy with medication. However, it is also necessary to monitor thyroid dysfunction even for patients who take medicine.

Patients have concerns about the adequacy of the medication dose they are taking and whether their body is currently experiencing side effects. Therefore, the present application will disclose a thyroid dysfunction monitoring method that may be provided to patients who take medicine.

In order to provide thyroid dysfunction monitoring to patients who take medicine, it is necessary to consider the following details.

As an example, when monitoring indicates a situation in which a patient is already suffering from hyperthyroidism and is taking a medicine, it is unnecessary to continuously warn the patient of hyperthyroidism because the patient is already on medication for hyperthyroidism, and also continuous alerts can excessively promote a sense of crisis for the patient.

As another example, when monitoring indicates a situation in which a patient is at risk for hypothyroidism while already suffering from hyperthyroidism and taking a medicine, it is necessary to warn the user as soon as possible because the amount of medicine is excessive for the patient.

Therefore, in order to provide thyroid dysfunction monitoring to patients who take medicine, it is important to perform appropriate thyroid dysfunction monitoring based on a user's medication. Therefore, a medication-based thyroid function monitoring system according to an embodiment of the present application will be described below.

4.1 Reception of Medication Information (S4100)

Figure 25:
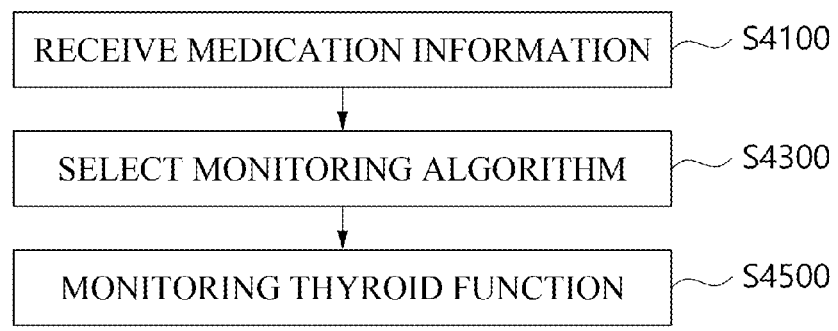
FIG. 25 is a diagram illustrating a medication-based thyroid function monitoring method according to an embodiment of the present application.

FIG. 25 is a diagram illustrating a medication-based thyroid function monitoring method S400 according to an embodiment of the present application.

The medication-based thyroid function monitoring method S400 may include medication information reception S4100, monitoring algorithm selection S4300, and thyroid function monitoring S4500. According to an embodiment, the operations S4100, S4300, and S4500 may be performed by the monitoring server 3000.

The monitoring server 3000 may receive medication information from the user terminal 2000 (S4100). The server communication unit 3100 may receive medication information from the user terminal 2000 (S4100). The medication information may be information acquired through the terminal input unit 2100. The medication information may be information that is transmitted to the monitoring server 3000 on the basis of a user's prescription information when the prescription information is acquired through the terminal input unit 2100. The medication information may be information that is transmitted to the monitoring server 3000 on the basis of a user's prescription information of the wearable device 1000 acquired from a separate server that manages the prescription information.

The user terminal 2000 may receive at least one of a medicine prescription date, a medicine name, a medicine type, a medicine dose, or a medication interval which is related to the user's thyroid function. As an example, the information may be received through the terminal input unit 2100 by the user's physical input (e.g., a touch input). As another example, the information may be received through the terminal input unit 2100 by imaging a prescription sheet or the like.

The user terminal 2000 may transmit medication information including at least one of the medicine prescription date, the medicine name, the medicine type, the medicine dose, or the medication interval which are related to the user's thyroid function to the monitoring server 3000.

4.2 Selection of Monitoring Algorithm (S4300)

When the medication information is received by the monitoring server 3000, the monitoring server 3000 may select a monitoring algorithm (S4300). When the medication information is received, the server control unit 3300 may select a monitoring algorithm (S4300).

Figure 26:
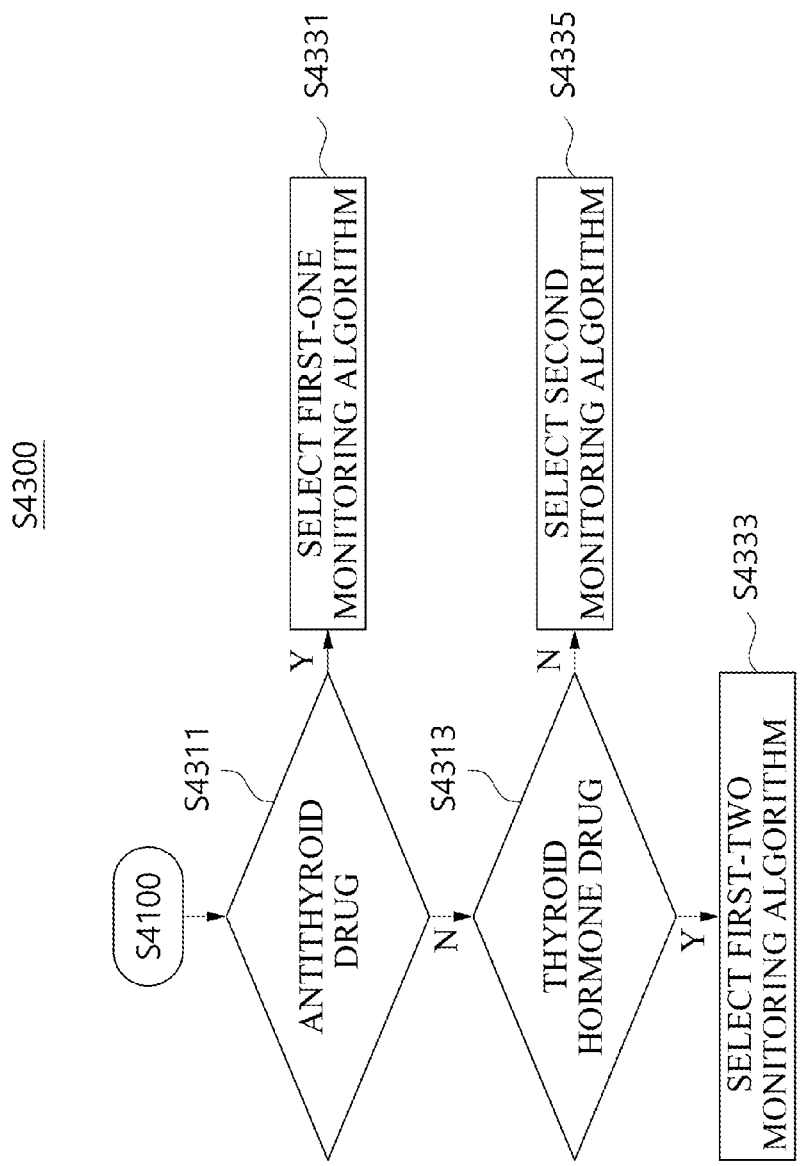
FIG. 26 is a flowchart illustrating a monitoring algorithm selection method according to an embodiment of the present application.

FIG. 26 is a flowchart illustrating a method for monitoring algorithm selection S4300 according to an embodiment of the present application.

When the medication information is received, the monitoring server 3000 may select a monitoring algorithm to be used to determine a user's thyroid dysfunction (S4300).

The monitoring server 3000 may check whether a medicine classified as an "antithyroid drug" is included in medicine that the user takes (S4311). When a medicine classified as an "antithyroid drug" is included in the medicine that the user takes, the monitoring server 3000 may select a first-one monitoring algorithm so that operation S4500 is performed according to the first-one monitoring algorithm (S4331).

When a medicine classified as an "antithyroid drug" is not included in the medicine that the user takes, the monitoring server 3000 may check whether a medicine classified as a "thyroid hormone drug" is included in the medicine that the user takes (S4313). When a medicine classified as a "thyroid hormone drug" is included in the medicine that the user takes, the monitoring server 3000 may select a first-two monitoring algorithm so that operation S4500 is performed according to the first-two monitoring algorithm (S4333).

When a medicine classified as a "thyroid hormone drug" is not included in the medicine that the user takes, the monitoring server 3000 may select a second monitoring algorithm so that operation S4500 is performed according to the second monitoring algorithm (S4335).

The monitoring server 3000 may allow operations S4311 and S4313 to be performed in reverse order or simultaneously. In this case, when it is determined that the user takes both of an "antithyroid drug" and a "thyroid hormone drug" on the basis of the medication information, the monitoring server 3000 may select the first-one monitoring algorithm so that operation S4500 is performed according to the first-one monitoring algorithm (S4331).

According to an embodiment of the present application, in order for the monitoring server 3000 to check whether a medication corresponding to an "antithyroid drug" and/or a "thyroid hormone drug" is included on the basis of the medication information, information with medicine names and medicine types mapped to each other may be stored in the server database 3200. The monitoring server 3000 may check whether a medicine corresponding to an "antithyroid drug" and/or a "thyroid hormone drug" is in the medication information with reference to the stored information with the medicine names and the medicine types.

According to another embodiment of the present application, the monitoring server 3000 may confirm a medicine type from the medication information and check whether the medicine type corresponds to an "anti-thyroid drug" and/or a "thyroid hormone drug" to check whether a medicine corresponding to the "anti-thyroid drug" and/or the "thyroid hormone drug" is in the medication information.

According to an embodiment of the present application, the monitoring server 3000 may further acquire the user's diagnosis information on the basis of the medication information. As an example, the monitoring server 3000 may classify the user into a hyperthyroidism treatment group or a hypothyroidism treatment group on the basis of the medication information.

In operation S4311, when it is determined that the medicine corresponding to the "anti-thyroid drug" is included in the medication information, the monitoring server 3000 may determine that the user is included in the hyperthyroidism treatment group. When it is determined that the user is included in the hyperthyroidism treatment group, the monitoring server 3000 may select the first-one monitoring algorithm so that operation S4500 is performed according to the first-one monitoring algorithm (S4331).

In operation S4313, when it is determined that the medicine corresponding to the "thyroid hormone drug" is included in the medication information, the monitoring server 3000 may determine that the user is included in the hypothyroidism treatment group. When it is determined that the user is included in the hypothyroidism treatment group, the monitoring server 3000 may select the first-two monitoring algorithm so that operation S4500 is performed according to the first-two monitoring algorithm (S4333).

When it is determined that no medicine corresponding to an "antithyroid drug" and a "thyroid hormone drug" is in the medication information, the monitoring server 3000 may select the second monitoring algorithm so that operation S4500 is performed according to the second monitoring algorithm (S4335). If necessary, the monitoring server 3000 may request information necessary to confirm the user's past medical history from the user terminal 2000. If necessary, the monitoring server 3000 may confirm data stored in the server database 3200 in order to confirm the user's past medical history.

4.3 Monitoring of Thyroid Dysfunction (S4500)

Continuing from FIG. 25, the monitoring server 3000 may perform thyroid function monitoring S4500 according to the selected algorithm. The server control unit 3300 may perform thyroid function monitoring S4500 on the basis of the selected monitoring algorithm.

Figure 27:
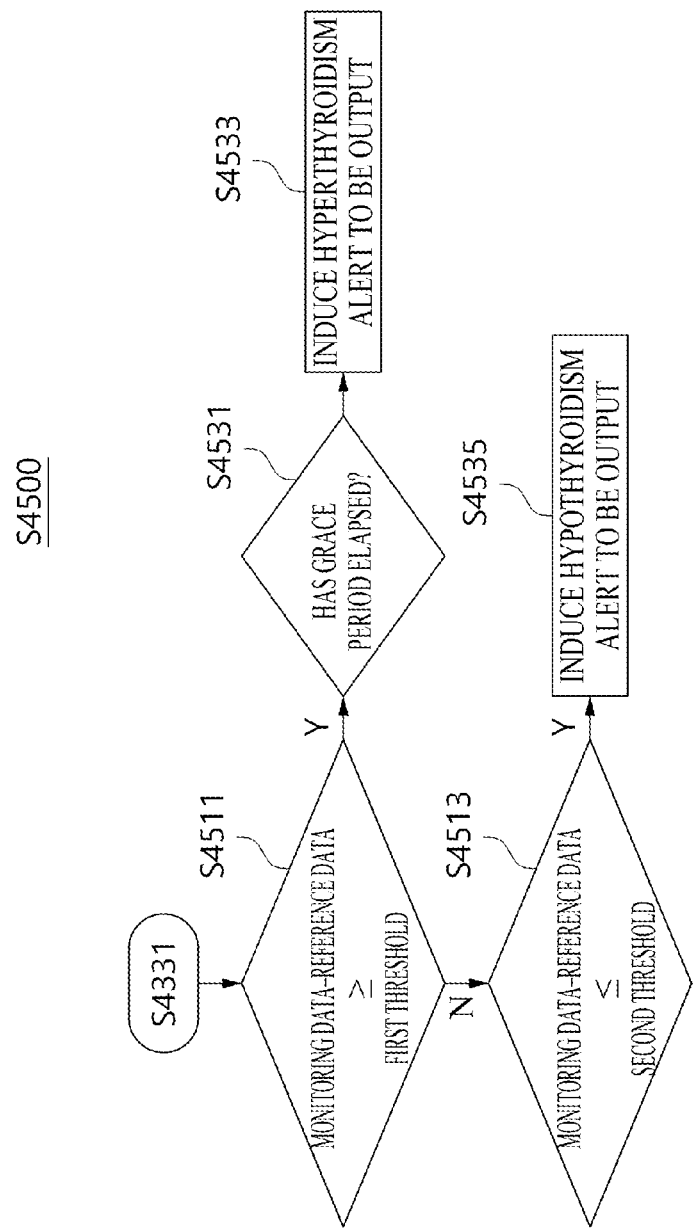
FIG. 27 is a flowchart illustrating a thyroid function monitoring method corresponding to the selection of a first-one monitoring algorithm according to an embodiment of the present application.

FIG. 27 is a flowchart illustrating a method for thyroid function monitoring S4500 corresponding to the selection of the first-one monitoring algorithm (S4331) according to an embodiment of the present application.

Referring to FIG. 27, the thyroid function monitoring S4500 may be performed by comparing monitoring data and reference data. The following description assumes that the monitoring data is a monitoring heart rate and the reference data is a reference heart rate.

The monitoring server 3000 may compare the monitoring data and the reference data. The monitoring server 3000 may compare whether the monitoring data is greater than the reference data by a first threshold or more (S4511).

When the monitoring data is greater than the reference data by the first threshold or more, the monitoring server 3000 may determine that the user's thyroid function is abnormal. As an example, when a monitoring heart rate is greater than a reference heart rate by a first threshold (e.g., 10) or more, the monitoring server 3000 may determine that the user's thyroid function is abnormal. The monitoring server 3000 may predict the user's hyperthyroidism.

However, when the first-one monitoring algorithm is selected, the user has already been diagnosed with hyperthyroidism and is taking a medicine for hyperthyroidism treatment, so it is not appropriate to continuously output an alert about visiting a hospital because hyperthyroidism is suspected.

Accordingly, when the first-one monitoring algorithm is selected and the monitoring data is greater than the reference data by the first threshold, the monitoring server 3000 may determine whether a grace period has elapsed on the basis of the medicine prescription date (S4531). When the grace period has elapsed, the monitoring server 3000 may induce an alert related to hyperthyroidism to be output (S4533). As an example, the grace period may be three months from the medicine prescription date. As another example, the grace period may be one month from the medicine prescription date. The grace period may be determined by the monitoring server 3000 that has received the medication information.

When, in operation S4533, it is determined that the user's hyperthyroidism persists, the monitoring server 3000 may transmit a signal to the user terminal 2000 (S4533) so that an alert related to the user's thyroid dysfunction is output through the terminal output unit 2200 of the user terminal 2000. As an example, the monitoring server 3000 may transmit a signal to the user terminal 2000 so that an alert about "visiting a hospital because there is a need to increase the dose of medicine" or "visiting a hospital and consulting with a doctor" is output through the terminal output unit 2200.

When the monitoring data is not greater than the reference data by the first threshold or more, the monitoring server 3000 may compare whether the monitoring data is smaller than the reference data by a second threshold or more (S4513).

When the monitoring data is smaller than the reference data by the second threshold or more, the monitoring server 3000 may determine that the user's thyroid function is abnormal. As an example, when a monitoring heart rate is smaller than a reference heart rate by a second threshold (e.g., 8 beats) or more, the monitoring server 3000 may determine that the user's thyroid function is abnormal. The monitoring server 3000 may predict the user's hypothyroidism.

When the monitoring data is smaller than the reference data by the second threshold or more, the monitoring server 3000 may induce an alert related to hypothyroidism to be output (S4535).

When, in operation S4535, it is determined that hypothyroidism has developed in the user, the monitoring server 3000 may transmit a signal to the user terminal 2000 (S4535) so that an alert related to the user's thyroid dysfunction is output through the terminal output unit 2200 of the user terminal 2000. As an example, the monitoring server 3000 may transmit a signal to the user terminal 2000 so that an alert about "visiting a hospital because the dose of medicine is determined as being excessive" or "visiting a hospital and consulting with a doctor" is output through the terminal output unit 2200.

Figure 28:
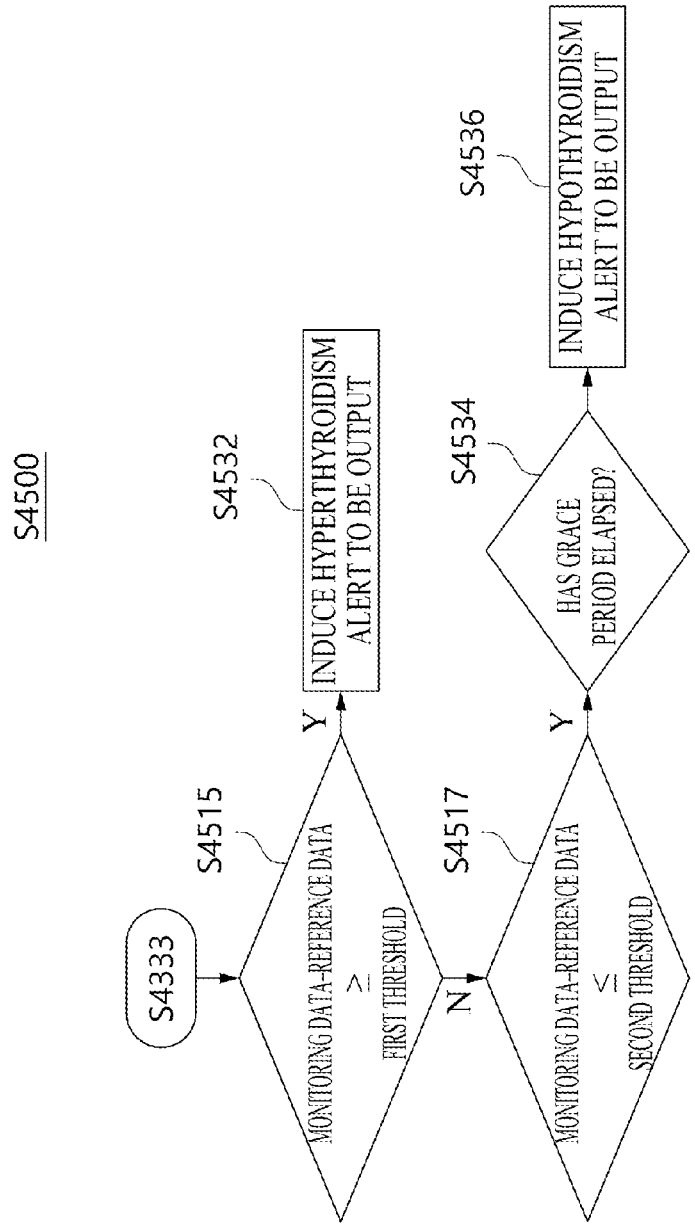
FIG. 28 is a flowchart illustrating a thyroid function monitoring method corresponding to the selection of a first-two monitoring algorithm according to an embodiment of the present application.

FIG. 28 is a flowchart illustrating a method for thyroid function monitoring S4500 corresponding to the selection of the first-two monitoring algorithm (S4333) according to an embodiment of the present application. According to an embodiment, the operation of FIG. 28 may be performed by the server control unit 3300.

Referring to FIG. 28, the thyroid function monitoring S4500 may be performed by comparing monitoring data and reference data. The following description assumes that the monitoring data is a monitoring heart rate and the reference data is a reference heart rate.

The monitoring server 3000 may compare the monitoring data and the reference data. The monitoring server 3000 may compare whether the monitoring data is greater than the reference data by a first threshold or more (S4511).

When the monitoring data is greater than the reference data by the first threshold or more, the monitoring server 3000 may determine that the user's thyroid function is abnormal. As an example, when a monitoring heart rate is greater than a reference heart rate by a first threshold (e.g., 10 beats) or more, the monitoring server 3000 may determine that the user's thyroid function is abnormal. The monitoring server 3000 may predict the user's hyperthyroidism.

When the monitoring data is greater than the reference data by the first threshold or more, the monitoring server 3000 may determine that the user's thyroid function is abnormal. The monitoring server 3000 may predict the user's hyperthyroidism.

When the monitoring data is greater than the reference data by the first threshold or more, the monitoring server 3000 may induce an alert related to hyperthyroidism to be output (S4532).

When, in operation S4515, it is determined that hyperthyroidism develops in the user, the monitoring server 3000 may transmit a signal to the user terminal 2000 (S4532) so that an alert related to the user's thyroid dysfunction is output through the terminal output unit 2200 of the user terminal 2000. As an example, the monitoring server 3000 may transmit a signal to the user terminal 2000 so that an alert about "visiting a hospital because the dose of medicine is determined as being excessive" or "visiting a hospital and consulting with a doctor" is output through the terminal output unit 2200.

When the monitoring data is not greater than the reference data by the first threshold or more, the monitoring server 3000 may compare whether the monitoring data is smaller than the reference data by a second threshold or more (S4513).

When the first-two monitoring algorithm is selected and the monitoring data is smaller than the reference data by the second threshold or more, the monitoring server 3000 may determine whether a grace period has elapsed on the basis of the medicine prescription date (S4534). When the grace period has elapsed, the monitoring server 3000 may induce an alert related to hyperthyroidism to be output (S4536). As an example, the grace period may be three months from the medicine prescription date. As another example, the grace period may be one month from the medicine prescription date. The grace period may be determined by the monitoring server 3000 that has received the medication information.

When, in operation S4534, it is determined that the user's hypothyroidism persists, the monitoring server 3000 may transmit a signal to the user terminal 2000 (S4536) so that an alert related to the user's thyroid dysfunction is output through the terminal output unit 2200 of the user terminal 2000. As an example, the monitoring server 3000 may transmit a signal to the user terminal 2000 so that an alert about "visiting a hospital because there is a need to increase the dose of medicine" or "visiting a hospital and consulting with a doctor" is output through the terminal output unit 2200.

According to an embodiment of the present application, when the second monitoring algorithm is selected (S4335), monitoring may be performed in the same manner as before the medication information is input to the monitoring server 3000.

As an example, when the second monitoring algorithm is selected (S4335), the monitoring server 3000 may output the alert when the monitoring heart rate is greater than the reference heart rate by the first threshold or more and may output the alert when the monitoring heart rate is smaller than the reference heart rate by the second threshold or more. When the second monitoring algorithm is selected (S4335), the thyroid function monitoring may be performed similarly to that described with reference to FIG. 11. Therefore, a redundant description will be omitted.

So far, the medication-based thyroid dysfunction monitoring S400 according to an embodiment of the present application has been described. However, the medication-based thyroid dysfunction monitoring S400 has been described using an example of performing risk determination on both of hypothyroidism and hyperthyroidism. However, the thyroid dysfunction monitoring may be performed by monitoring only hypothyroidism or by monitoring only hyperthyroidism.

Therefore, the scope of the present application should not be construed as being limited to the specific examples described for understanding in this specification, and the scope of the present application should be interpreted according to the interpretation of the claims of the present application.

Figure 29:
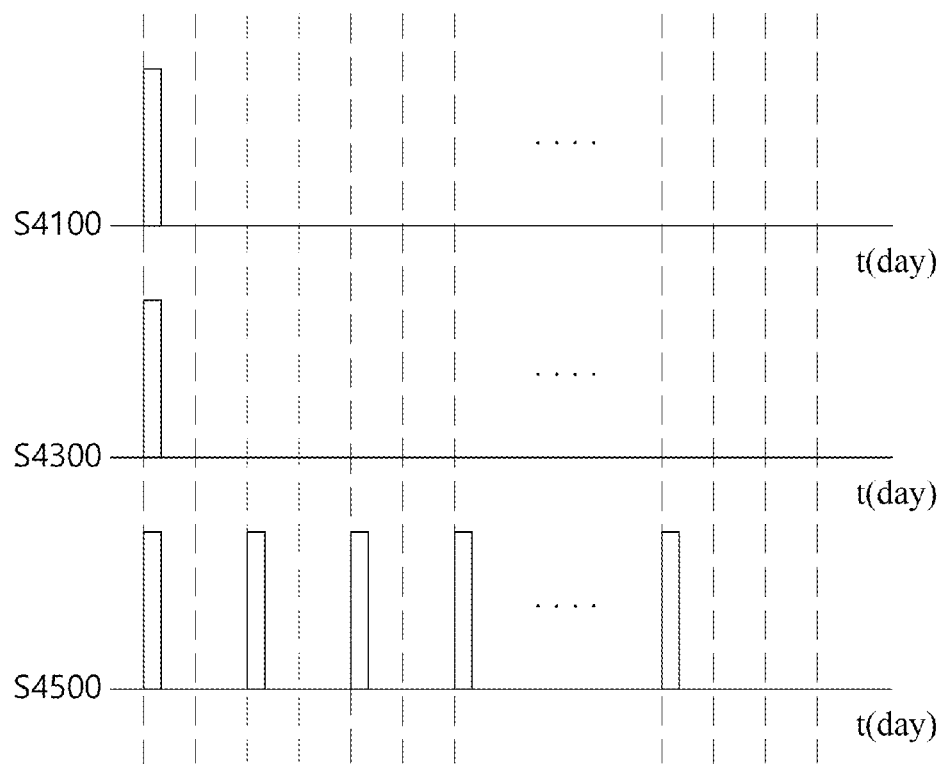
FIG. 29 is a diagram illustrating an operation timing of a thyroid dysfunction monitoring method S400 according to an embodiment of the present application.

FIG. 29 is a diagram illustrating an operation timing of a thyroid dysfunction monitoring method S400 according to an embodiment of the present application.

According to an embodiment of the present application, a monitoring algorithm may be selected (S4300) using the reception of medication information (S4100) as a trigger. When the medication information is received (S4100), the monitoring server 3000 may select a monitoring algorithm (S4300).

The number of times the monitoring server 3000 selects a monitoring algorithm (S4300) may correspond to the number of times the monitoring server 3000 receives medication information (S4100). Alternatively, the number of times the monitoring server 3000 selects a monitoring algorithm (S4300) may be greater than or equal to the number of times the monitoring server 3000 receives medication information (S4100).

After the monitoring server 3000 selects a monitoring algorithm (S4300), the monitoring server 3000 may perform thyroid function monitoring (S4500) corresponding to the monitoring algorithm. Until a new event is generated after the monitoring server 3000 selects a monitoring algorithm (S4300), the monitoring server 3000 may perform thyroid function monitoring (S4500) corresponding to the monitoring algorithm at monitoring intervals.

The number of times the monitoring server 3000 performs thyroid function monitoring (S4500) may be greater than the number of times the monitoring server 3000 receives medication information (S4100). The number of times the monitoring server 3000 performs thyroid function monitoring (S4500) may be greater than the number of times the monitoring server 3000 selects a monitoring algorithm (S4300).

As an example, when a patient inputs prescription information to the user terminal 2000 after visiting a hospital, the user terminal 2000 may transmit the input information to the monitoring server 3000. When medication information (e.g., including some information included in the prescription information) is received by the monitoring server 3000, the monitoring server 3000 may select a monitoring algorithm (S4300). When a monitoring algorithm is selected (S4300), the monitoring server 3000 may perform the thyroid function monitoring (S4500) at monitoring intervals. As a specific example, after a monitoring algorithm is selected (S4300), the monitoring server 3000 may perform thyroid function monitoring (S4500) once a day.

When the thyroid function monitoring is performed (S4500), information regarding reference data (e.g., a reference heart rate) may be stored in the monitoring server 3000. The reference data stored in the monitoring server 3000 may be calculated in response to the reception of the user's thyroid state information (S2100). A reference data calculation interval of the monitoring server 3000 and a monitoring algorithm selection interval of the monitoring server 3000 may be independent of each other. The reference data calculation interval of the monitoring server 3000 and a monitoring algorithm selection time point of the monitoring server 3000 may have an overlapping period.

5. Medication Management

According to an embodiment of the present application, the monitoring server 3000 may provide a medication notification on the basis of the received medication information. The monitoring server 3000 may induce a medication notification to be output on the basis of a medication interval included in the medication information.

In order to provide a medication notification to a user, the monitoring server 3000 may transmit a signal to the user terminal 2000. As an example, the user terminal 2000 may inform the user that it is time to take the medicine on the basis of the signal received from the monitoring server 3000.

Figure 30:
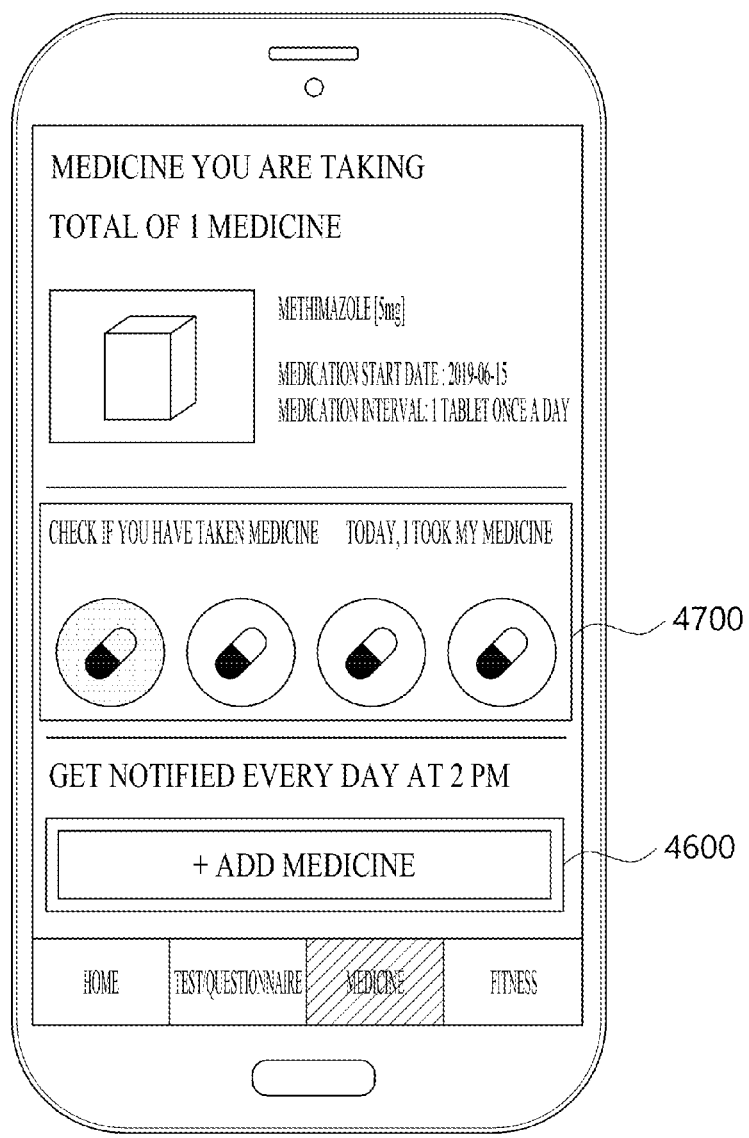
FIG. 30 is a diagram illustrating a user interface of a user terminal that provides a medication recommendation according to an embodiment of the present application.

FIG. 30 is a diagram illustrating a user interface 400 of a user terminal 2000 that provides a medication recommendation according to an embodiment of the present application.

Referring to FIG. 30, the user terminal 2000 may output a user interface 400 including a medicine information input interface 4600 and a medication notification interface 4700.

The medicine information input interface 4600 may be an interface for receiving prescription information from a user. When the user selects the medicine information input interface 4600, a specific interface for receiving medicine information may be further output to the user terminal 2000. As an example, an interface for receiving medication information including at least one of a medicine prescription date, a medicine name, a medicine type, a medicine dose, or a medication interval which are related to a thyroid function may be provided. As another example, the user terminal 2000 may be provided with an interface for taking a picture of the user's prescription sheet. As another example, in order to receive a user's prescription information from a separate server, the user terminal 2000 may be provided with an interface for receiving user authentication information.

The medication notification interface 4700 may include an interface for checking that a medicine is taken after medication is administered. The medication notification interface 4700 may include an interface for indicating a medication time and inducing the user to take a medicine at the medication time.

As an example, the user terminal 2000 may be provided with an interface for providing a notification so that the user can take a medicine at the medication time. The corresponding interface may be a screen that can be checked when a program for thyroid function monitoring is being output to the user terminal 2000. The corresponding interface may be a screen that is provided in the form of a popup when another program is running on the user terminal 2000.

As an example, the monitoring server 3000 may output a medication recommendation more frequently than the thyroid dysfunction monitoring S4500 is performed. As an example, when the thyroid dysfunction monitoring S4500 is performed once a day, a medication recommendation may be performed three times a day.

As another example, the monitoring server 3000 may output a medication recommendation as many times as the number of times the thyroid dysfunction monitoring S4500 is performed. As an example, when the thyroid dysfunction monitoring S4500 is performed once a day, a medication recommendation may be performed once a day.

So far, a thyroid dysfunction monitoring method according to some embodiments when a thyroid function monitoring system 100 includes a wearable device 1000, a user terminal 2000, and a monitoring server 3000 has been specifically disclosed.

However, the thyroid function monitoring system 100 may be modified and implemented within a scope that is easy for those skilled in the art.

According to an embodiment of the present application, the above-described thyroid dysfunction monitoring method may be provided in the form of a recording medium where a program for performing the method is recorded and where code readable and executable by a computer is stored.

According to an embodiment of the present application, the above-described thyroid dysfunction monitoring method may be provided in the form of a wearable device 1000, a user terminal 2000, and/or a monitoring server 3000 for performing the corresponding method.

According to an embodiment of the present application, the above-described thyroid dysfunction monitoring method may be provided in the form of a thyroid function monitoring system 100 including at least one of a wearable device 1000, a user terminal 2000, and/or a monitoring server 3000 for performing the corresponding method.

As an example, the thyroid function monitoring system 100 may be implemented by including only the wearable device 1000 and the monitoring server 3000. In this case, information to be output through the user terminal 2000 may be output through the wearable device 1000. Information input through the user terminal 2000 may be input through the wearable device 1000. Information regarding a user's thyroid dysfunction determined by the monitoring server 3000 may be output through the wearable device 1000. The wearable device 1000 may function as an input interface for receiving specific information such as thyroid state information and medication information from a user.

As another example, the thyroid function monitoring system 100 may be implemented by including only the wearable device 1000 and the user terminal 2000. In this case, the user terminal 2000 may perform the above-described operation of the monitoring server 3000 by executing a program stored in the terminal memory unit 2400.

As another example, the thyroid function monitoring system 100 may be implemented by including the wearable device 1000, the monitoring server 3000 communicating with the wearable device 1000, and the user terminal 2000 communicating with the monitoring server 3000. In this case, the wearable device 1000 may transmit acquired biometric information to the monitoring server 3000, and the monitoring server 3000 may perform thyroid function monitoring using the acquired biometric information. The monitoring server 3000 may perform an operation of transmitting the biometric information received from the wearable device 1000 to the user terminal 2000 in order to output heart rate information to the user terminal.

In addition, the thyroid function monitoring system 100 may be implemented in various forms.

The thyroid dysfunction determination method using skin conductance according to the present invention will be described below.

6. Thyroid Dysfunction Monitoring Method Using Skin Conductance

Figure 31:
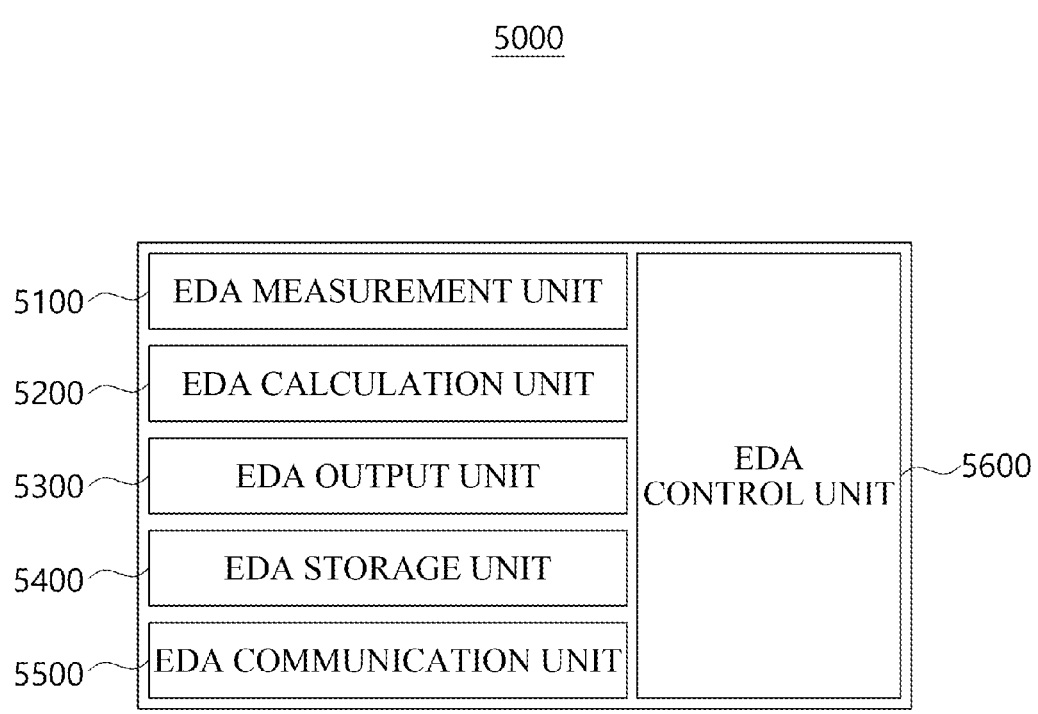
FIG. 31 is a diagram showing a block diagram of a skin conductance measurement sensor according to an embodiment.

FIG. 31 is a diagram showing a block diagram of a skin conductance measurement sensor. The skin conductance measurement sensor according to an embodiment may be expressed as an electrodermal activity (EDA) sensor.

Referring to FIG. 31, an EDA sensor 5000 may include an EDA measurement unit 5100, an EDA calculation unit 5200, an EDA output unit 5300, an EDA storage unit 5400, an EDA communication unit 5500, and an EDA control unit 5600. However, the components shown in FIG. 31 are not essential, and the EDA sensor 5000 may have more components or fewer components.

The EDA sensor 5000 may be included in an electronic device. The EDA sensor 5000 may be included in the wearable device 1000. For example, the EDA sensor 5000 may be included in a smartwatch, a smart ring, a detachable patch, etc., but the present invention is not limited thereto.

For example, the EDA sensor 5000 may measure the skin conductance of a user who wears the wearable device 1000. In this case, the EDA measurement unit 5100 included in the EDA sensor 5000 may measure the user's skin conductance.

According to an embodiment of the present application, the EDA sensor 5000 may be integrated with the wearable device 1000. As an example, the EDA sensor 5000 may be a sensor included in the device sensor unit 1400. In this case, the EDA sensor 5000 may be controlled by the device control unit 1600.

As a specific example, the device control unit 1600 may control the EDA measurement unit 5100 to measure skin conductance and control the device communication unit 1300 to transmit the measured skin conductance to the user terminal 2000.

The EDA measurement unit 5100 may measure the user's skin conductance through an electrode. Also, the EDA measurement unit 5100 may include a plurality of electrodes capable of coming in contact with the user's skin. For example, the EDA measurement unit 5100 may include two electrodes serving as a positive electrode and a negative electrode.

According to an embodiment, the distance between the electrodes may be designed to vary depending on the thickness of the user's stratum corneum. For example, the distance between the electrodes may be designed to be greater than the thickness of the user's stratum corneum.

In this case, a user with a thin stratum corneum may use a wearable device 1000 including an EDA sensor 5000 having a smaller distance between electrodes than a user with a thick stratum corneum.

According to an embodiment, the EDA measurement unit 5100 may measure the user's skin conductance by allowing a current less than a predetermined value to flow to the user's skin through two electrodes.

For example, the EDA measurement unit 5100 may measure the user's skin conductance by allowing DC current or AC current to flow to the user's skin through an electrode.

In this case, measurement accuracy may be higher when DC current flows than when AC current flows, but in this case, the possibility of hair root destruction may be high.

Conversely, measurement accuracy may be lower when AC current flows than when DC current flows, but in this case, the possibility of hair root destruction may be low.

According to an embodiment, the EDA measurement unit 5100 may include a virtual ground, a current source, and a low-pass filter. Also, the EDA measurement unit 5100 may further include an amplifier, but the present invention is not limited thereto. In this case, the low-pass filter or the amplifier may be included in the EDA measurement unit 5100 or may be included in the EDA calculation unit 5200.

The EDA measurement unit 5100 may acquire a result value obtained by sensing the user's skin conductance through a current source connected to the electrode. Also, the EDA measurement unit 5100 may increase the accuracy of skin conductance data through the low-pass filter.

The EDA measurement unit 5100 may transmit the measured result value to the EDA calculation unit 5200, the EDA communication unit 5500, or the EDA storage unit 5400.

Also, when the EDA sensor 5000 is not physically the same as the wearable device 1000, the EDA measurement unit 5100 may transmit the measured result value (e.g., skin conductance data) to the device input unit 1100 through the EDA communication unit 5500.

The EDA calculation unit 5200 may receive the result value of the EDA measurement unit 5100. The EDA calculation unit 5200 may process the result value of the EDA measurement unit 5100. The EDA calculation unit 5200 may obtain skin conductance data on the basis of the result value of the EDA measurement unit 5100.

As another example, the EDA calculation unit 5200 may obtain the result value as the skin conductance data without processing the result value. In this case, the EDA measurement unit 5100 and the EDA calculation unit 5200 may not be distinct from each other and may be one unit or module.

According to an embodiment, the EDA calculation unit 5200 may filter the result value of the EDA measurement unit 5100 using a filter. For example, the EDA calculation unit 5200 may filter the result value of the EDA measurement unit 5100 using a Schmitt trigger filter or a recursive moving filter. However, the present invention is not limited thereto, and the EDA calculation unit 5200 may use other filters.

According to another embodiment, the EDA calculation unit 5200 may process the result value of the EDA measurement unit 5100.

For example, the EDA calculation unit 5200 may convert the result value of the EDA measurement unit 5100 into another value through Ohm's law. As a specific example, when the result value of the EDA measurement unit 5100 is resistance, the EDA calculation unit 5200 may convert the result value into a voltage or a current through Ohm's law. An example of changing voltage into current or resistance and an example of changing current into resistance or voltage are possible.

For example, the EDA calculation unit 5200 may divide the result value of the EDA measurement unit 5100 into Tonic EDA and Phasic EDA. Details of the Tonic EDA and the Phasic EDA will be described below.

Also, for example, the EDA calculation unit 5200 may convert the result value of the EDA measurement unit 5100 into skin conductance level (SCL). In this case, the SCL may be a log value of the result value.

Also, for example, the EDA calculation unit 5200 may use the result value of the EDA measurement unit 5100 to extract parameters such as skin conductance fluctuation rate (SCFr), skin conductance response rate (SCRr), skin conductance response habitation (SCRh), skin conductance response magnitude (SCRm), skin conductance response onset latency (SCRol), skin conductance response peak latency (SCRpl), skin conductance response duration (SCRd), skin conductance response peak rate (SCRpr), skin conductance response recovery rate (SCRrr), etc. The listed parameters may be understood in more detail through the description of FIG. 34, and a detailed descriptions thereof will be omitted herein.

Also, for example, the EDA calculation unit 5200 may calculate the average, median, and standard deviation of the result value of the EDA measurement unit 5100.

Also, for example, the EDA calculation unit 5200 may calculate the average, median, and standard deviation of SCL, SCFr, SCRr, SCRh, SCRm, SCRol, SCRpl, SCRd, SCRpr, and SCRrr.

The EDA calculation unit 5200 may transmit the skin conductance data, which is a result of the calculation, to the EDA output unit 5300, the EDA storage unit 5400, and the EDA communication unit 5500.

Also, when the EDA sensor 5000 is not physically the same as the wearable device 1000, the EDA calculation unit 5200 may transmit the calculation result to the device input unit 1100 through the EDA communication unit 5500.

The EDA output unit 5300 may receive the skin conductance data, which is the calculation result of the EDA calculation unit 5200. The EDA output unit 5300 may output the skin conductance data. The EDA output unit 5300 may be configured to provide visual, audible, and/or tactile output. However, the present invention is not limited thereto, and the EDA output unit 5300 may be formed in various forms.

For example, the EDA output unit 5300 may be implemented as a display for outputting images, a speaker for outputting sounds, a haptic device for generating vibration, and/or various other types of output means.

The EDA output unit 5300 may be implemented in the form of an output interface for connecting an external output device for outputting information to the wearable device 1000 instead of a device for outputting information to the outside.

The EDA output unit 5300 may be connected to the device output unit 1200 of the wearable device 1000. For example, the EDA output unit 5300 may be connected to the device output unit 1200 to communicate with the device through the EDA communication unit 5500.

In this case, the device output unit 1200 may output the result value of the EDA output unit 5300 through the display, speaker, haptic device, or various other types of output means of the wearable device 1000.

The EDA output unit 5300 may perform the same function as the above-described device output unit 1200.

According to an embodiment, the EDA output unit 5300 may be provided in the form of the same component as the device output unit 1200 of the wearable device 1000.

The EDA storage unit 5400 may receive skin conductance data, which is the calculation result of the EDA calculation unit 5200. The EDA storage unit 5400 may store the skin conductance data.

The EDA storage unit 5400 may store various kinds of data and programs required for the EDA sensor 5000 to operate. The EDA storage unit 5400 may store information that the EDA sensor 5000 acquires.

The EDA storage unit 5400 may temporarily or semi-permanently store data. Examples of the EDA storage unit 5400 may include an HDD, an SSD, a flash memory, a ROM, a RAM, or a cloud storage. However, the present invention is not limited thereto, and the EDA storage unit 5400 may be implemented as various modules for storing data.

The EDA storage unit 5400 may be built into or detachable from the EDA sensor 5000.

The EDA storage unit 5400 may perform the same function as the above-described device memory unit 1500. As an example, the EDA storage unit 5400 may store the skin conductance data until the skin conductance data is transmitted through the device communication unit 1300.

According to an embodiment, the EDA storage unit 5400 may be provided in the form of the same component as the device memory unit 1500 of the wearable device 1000.

Also, when the EDA sensor 5000 is not physically the same as the wearable device 1000, the EDA storage unit 5400 may transmit a stored value to the device memory unit 1500 through the EDA communication unit 5500.

The EDA communication unit 5500 may serve to enable the EDA sensor 5000 to transmit data to or receive data from an external device. For example, the EDA communication unit 5500 may serve to enable the EDA sensor 5000 to transmit data to or receive data from the wearable device 1000.

The EDA communication unit 5500 may include one or more modules that enable communication. The EDA communication unit 5500 may include a module for communicating with an external device in a wired manner. Alternatively, the EDA communication unit 5500 may include a module for communicating with an external device in a wireless manner.

Alternatively, the EDA communication unit 5500 may include a module that enables communication with an external device in a wireless manner and a module that enables communication with an external device in a wired manner.

As a specific example, the EDA communication unit 5500 may be a wired communication module that accesses the Internet through a LAN, a mobile communication module, such as LTE, that accesses a mobile communication network through a mobile communication base station to transmit and receive data, a short-range communication module that uses a communication scheme based on a WLAN such as Wi-Fi or a communication scheme based on a WPAN such as Bluetooth and Zigbee, a satellite communication module that uses a GNSS such as GPS, or a combination thereof.

The EDA communication unit 5500 may perform the same function as the above-described device communication unit 1300. As an example, the EDA communication unit 5500 may communicate with the user terminal 2000 and/or the monitoring server 3000.

According to an embodiment, the EDA communication unit 5500 may be provided in the form of the same component as the device communication unit 1300 of the wearable device 1000.

The EDA control unit 5600 may perform a function of overseeing and controlling the overall operation of the EDA sensor 5000. The EDA control unit 5600 may compute and process various kinds of information and may control operation of the elements of the terminal.

The EDA control unit 5600 may be implemented with a computer or the like in hardware, software, or a combination thereof. The EDA control unit 5600 in hardware may be provided in the form of an electronic circuit for processing electrical signals to perform a control function, such as a central processing unit (CPU) chip, and the EDA control unit 5600 in software may be provided in the form of a program for driving the EDA control unit 5600 in hardware.

According to an embodiment, the EDA control unit 5600 may perform control such that current flows to skin through an electrode in order for the EDA measurement unit 5100 to measure a user's skin conductance. Also, the EDA control unit 5600 may control the EDA measurement unit 5100 to transmit a result value to the EDA calculation unit 5200, the EDA communication unit 5500, or the EDA storage unit 5400.

Also, according to an embodiment, the EDA control unit 5600 may control the EDA calculation unit 5200 to receive the result value of the EDA measurement unit 5100. Also, the EDA control unit 5600 may control the EDA calculation unit 5200 to obtain skin conductance data. Also, the EDA control unit 5600 may control the EDA calculation unit 5200 to transmit the skin conductance data to the EDA output unit 5300, the EDA storage unit 5400, and the EDA communication unit 5500.

Also, according to an embodiment, the EDA control unit 5600 may control the EDA output unit 5300 to receive skin conductance data, which is the calculation result of the EDA calculation unit 5200. Also, the EDA control unit 5600 may control the EDA output unit 5300 to output the skin conductance data.

Also, according to an embodiment, the EDA control unit 5600 may control the EDA storage unit 5400 to receive the skin conductance data. Also, the EDA control unit 5600 may control the EDA storage unit 5400 to store the skin conductance data.

Also, according to an embodiment, the EDA control unit 5600 may control the EDA communication unit 5500 to communicate with an external device.

The EDA control unit 5600 may perform the same function as the above-described device control unit 1600.

According to an embodiment, the EDA control unit 5600 may be provided in the form of the same component as the device control unit 1600 of the wearable device 1000.

In the following description, unless otherwise specified, the operation of the EDA sensor 5000 may be interpreted as being performed by control of the EDA control unit 5600.

Figure 32A:
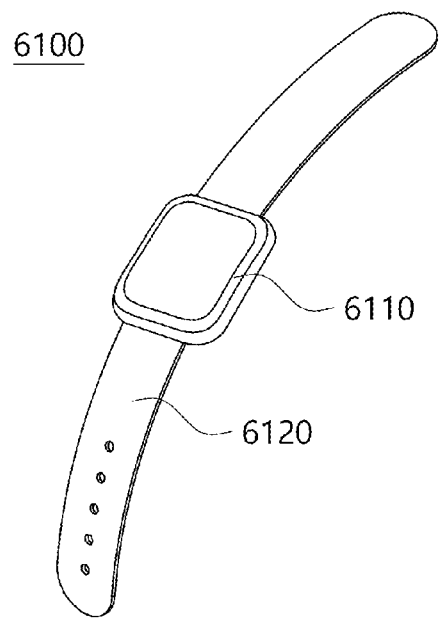
FIGS. 32A and 32B are showing devices for measuring skin conductance according to an embodiment.
Figure 32B:
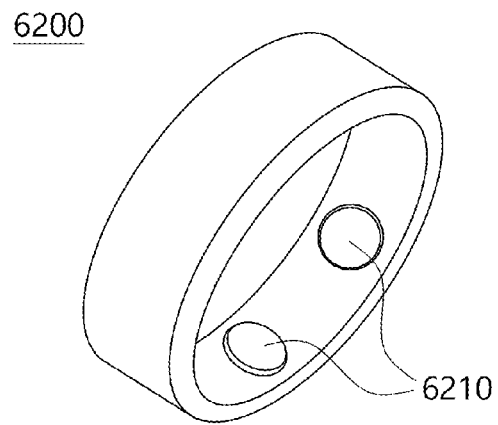

FIGS. 32A and 32B are showing devices for measuring skin conductance according to an embodiment.

Referring to FIGS. 32A and 32B, FIG. 32A shows a smart watch 6100, which is a wearable device, and FIG. 32B is a diagram showing a smart ring 6200, which is a wearable device. The smart watch 6100 and/or the smart ring 6200 may be the same as, or perform the same role as, the wearable device 1000.

Although only the smart watch 6100 and the smart ring 6200 are shown as devices capable of measuring skin conductance in FIGS. 32A and 32B, these are only described with reference to some embodiments for convenience of description, and the present invention is not limited thereto.

For example, a device that measures skin conductance may be a wristband that is worn on a user's wrist, wearable socks that are worn on a user's feet in the form of socks, a wearable patch that is attached to a user's skin, a wearable headband that is worn on a user's head, a device that is worn on a user's ear in the form of an earring, a device that is fitted in the form of an earphone, and a device that is inserted into a user's eye in the form of a lens. The device is not limited to the examples listed in the present application and may be implemented in various forms.

The wearable devices of FIGS. 32A and 32B may include the EDA sensor 5000 of FIG. 31.

According to an embodiment, a smart watch 6100 of FIG. 32A may include the EDA sensor 5000 in a main body 6110. For example, the main body 6110 of the smart watch 6100 may include an EDA measurement unit 5100 at a part to be brought into contact with the user's skin to measure the user's skin conductance.

Specifically, an electrode of the EDA measurement unit 5100 may be disposed on the back of the main body 6110 to enable a current to flow to the user's skin in order to measure the user's skin conductance.

According to another embodiment, the smart watch 6100 of FIG. 32A may include some elements of the EDA sensor 5000 in the main body 6110 and the other elements of the EDA sensor 5000 in a band region 6120. For example, the band region 6120 of the smart watch 6100 may include the EDA measurement unit 5100 at a part to be brought into contact with the user's skin to measure the user's skin conductance.

Specifically, the electrode of the EDA measurement unit 5100 may be disposed on the back of the band region 6120 to enable a current to flow to the user's skin in order to measure the user's skin conductance.

According to an embodiment, a smart ring 6200 of FIG. 32B may include the EDA sensor 5000. For example, the smart ring 6200 may include an EDA measurement unit 5100 at a part to be brought into contact with the user's skin to measure the user's skin conductance.

Specifically, an electrode 6210 of the EDA measurement unit 5100 may be disposed on an inner region of the smart ring 6200 to enable a current to flow to the user's skin in order to measure the user's skin conductance.

Figure 33:
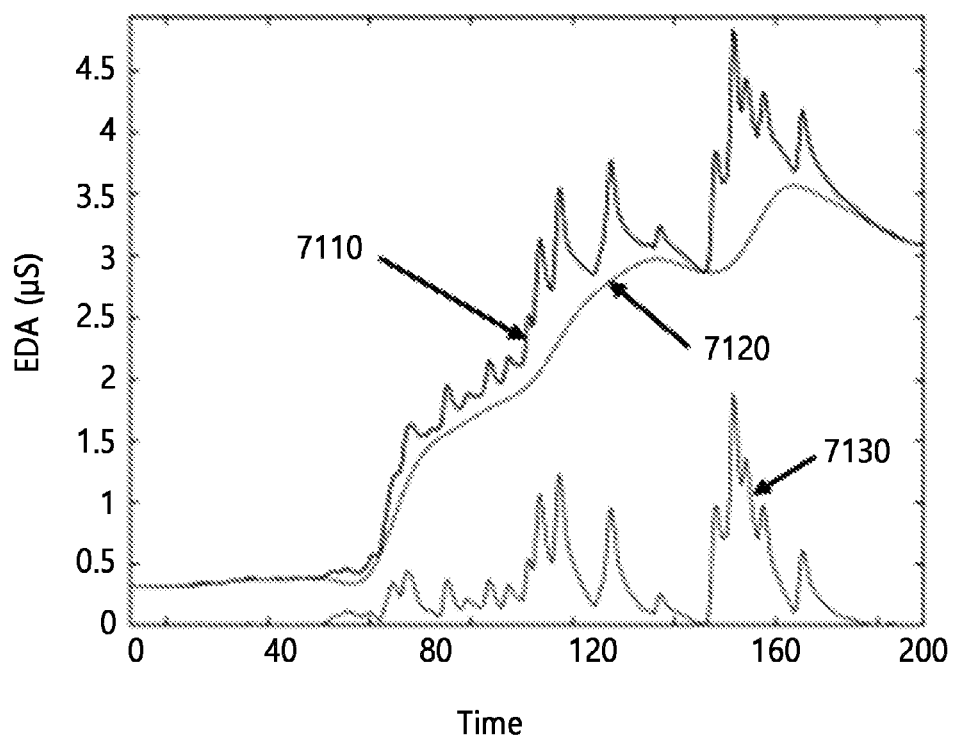
FIG. 33 is a diagram showing a skin conductance graph according to an embodiment.

FIG. 33 is a diagram showing a skin conductance graph according to an embodiment.

Referring to FIG. 33, the skin conductance graph may show skin conductance data 7110 over time. The skin conductance data 7110 may include a tonic component 7120 and a phasic component 7130.

According to an embodiment, the skin conductance data 7110 may be data acquired by the EDA sensor 5000.

According to an embodiment, the skin conductance data 7110 may include the sum of the tonic component 7120 and the phasic component 7130.

For example, the tonic component 7120 may be skin conductance data associated with an external environment (e.g., an ambient temperature) among the skin conductance data 7110. Alternatively, for example, the tonic component 7120 may be a portion of skin conductance data indicating a skin conductance level (SCL).

Also, for example, the phasic component 7130 may be skin conductance data associated with an external stimulus, an environmental stimulus, or a short-term event.

Alternatively, for example, the phasic component 7130 may be a portion of skin conductance data indicating a skin conductance response (SCR).

For example, the tonic component 7120 may be obtained by excluding the phasic component 7130 from the skin conductance data 7110. Also, the phasic component 7130 may be obtained by excluding the tonic component 7120 from the skin conductance data 7110.

Also, for example, the phasic component 7130 may be obtained by a convolution operation between a response function and the skin conductance data 7110.

Also, the tonic component 7120 and the phasic component 7130 may be converted into the unit of current, resistance, or voltage by Ohm's law.

According to an embodiment, the tonic component 7120 and the phasic component 7130 may be acquired through the arithmetic operation of the EDA calculation unit 5200 of the EDA sensor 5000. According to an embodiment, the tonic component 7120 and the phasic component 7130 may be acquired through the arithmetic operation of the server control unit 3300 of the monitoring server 3000 which receives the skin conductance data. According to an embodiment, the tonic component 7120 may be used as an indicator indicating the trend of occurrence or the magnitude of the skin conductance. The user's biometric information may be inferred using the trend of occurrence or the magnitude of the skin conductance. For example, the monitoring server 3000 may detect a change in skin temperature or body temperature on the basis of the overall change in the tonic component 7120.

Also, the phasic component 7130 may be used as an indicator indicating a storm expressed by the degree of change in skin conductance, the amount of change in skin conductance, or the first derivative of the skin conductance. For example, the monitoring server 3000 may predict the user's change in feelings, stress, excitement level, or autonomic nervous system through the overall change of the phasic component 7130.

According to an embodiment of the present application, the monitoring server 3000 may acquire the tonic component 7120 and/or the phasic component 7130 on the basis of the skin conductance data and may perform the user's thyroid dysfunction monitoring with reference to the acquired tonic component 7120 and/or phasic component 7130.

As an example, the monitoring server 3000 may calculate monitoring skin conductance on the basis of the tonic component 7120 corresponding to a resting period. When the calculated monitoring skin conductance is higher than reference skin conductance, the monitoring server 3000 may determine that the user has thyroid dysfunction.

Figure 34:
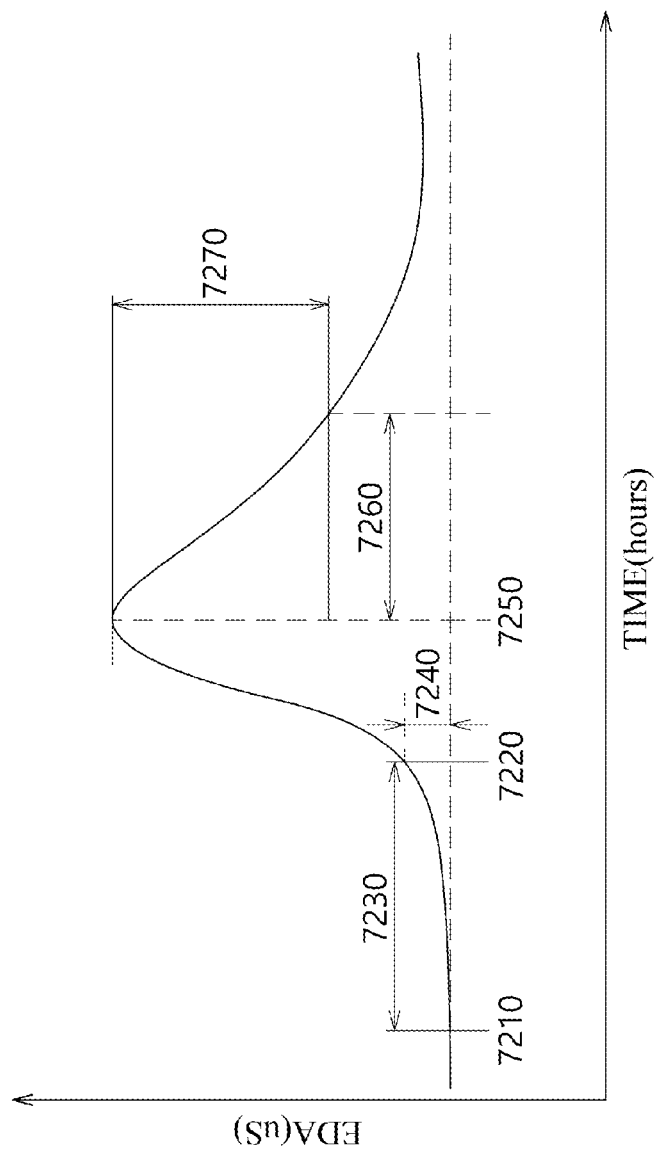
FIG. 34 is a diagram showing a skin conductance graph according to another embodiment.

FIG. 34 is a diagram showing a skin conductance graph according to another embodiment.

Referring to FIG. 34, several parameters that may be acquired through an analysis of the skin conductance data graph are shown.

The monitoring server 3000 may confirm a stimulus onset 7210, a response onset 7220, a latency 7230, a response threshold 7240, a peak response 7250, a recovery time 7260, and/or an amplitude 7270 on the basis of the skin conductance data graph.

For example, the stimulus onset 7210 may be a time point at which the skin conductance data starts to increase. Also, for example, the response onset 7220 may be a time point at which the magnitude is greater than or equal to a predetermined value from the stimulus onset 7210. In this case, the difference in magnitude between the stimulus onset 7210 and the response onset 7220 may be the response threshold 7240.

Also, for example, the latency 7230 may be calculated through the stimulus onset 7210 and the response onset 7220. Specifically, the latency 7230 may be a period from the stimulus onset 7210 to the response onset 7220.

According to an embodiment, the monitoring server 3000 may determine the degree of change of the user's skin conductance and the user's change in feelings, stress, or autonomic nervous system through the length of the latency 7230. For example, when the latency 7230 is short, the monitoring server 3000 may determine that the change in the user's skin conductance is rapid.

Also, for example, when the latency 7230 is short, the monitoring server 3000 may determine that the user's feelings change rapidly, the user is stressed, or the user's autonomic nervous system changes rapidly.

According to an embodiment, the monitoring server 3000 may adjust the sensitivity of the amount of change in skin conductance by adjusting the response threshold 7240. For example, by decreasing the response threshold 7240, the change frequency of skin conductance may increase. Also, for example, by increasing the response threshold 7240, the monitoring server 3000 may determine that the change frequency of skin conductance decreases and the skin conductance changes with only relatively large changes.

Also, for example, the peak response 7250 may be a time point at which the skin conductance data has the largest value after the stimulus onset 7210 or after the response onset 7220. Alternatively, the peak response 7250 may be a time point at which the first derivative of the skin conductance data is zero. Alternatively, the peak response 7250 may be a time point at which the first derivative of the skin conductance data is zero and the second derivative is negative.

According to an embodiment, through the peak response 7250, the monitoring server 3000 may recognize the maximum of the skin conductance data for a predetermined period and may determine the user's change in feelings, stress, or autonomic nervous system. For example, when the peak response 7250 is large, the monitoring server 3000 may determine that the user's change in feelings, stress, or autonomic nervous system is large.

Also, for example, the recovery time 7260 may refer to a time taken for the skin conductance data to reach a predetermined value from the peak response 7250.

In this case, a magnitude from the peak response 7250 to the predetermined value may be the amplitude 7270 of the skin conductance data. However, the amplitude 7270 may be a magnitude from the peak response 7250 to a value not related to the recovery time 7260 rather than the predetermined value related to the recovery time 7260.

In this case, the recovery time 7260 may be associated with a period from the latency 7230 or the response onset 7220 to the peak response 7250.

For example, when the period from the latency 7230 or the response onset 7220 to the peak response 7250 is shortened, the recovery time 7260 may also be shortened. Also, for example, when the period from the latency 7230 or the response onset 7220 to the peak response 7250 is lengthened, the recovery time 7260 may also be lengthened.

According to an embodiment, through the recovery time 7260 or the amplitude 7270, the monitoring server 3000 may determine the user's change in feelings, stress, or autonomic nervous system. For example, when the recovery time 7260 is short, the monitoring server 3000 may determine that the user's feelings change rapidly, the user is highly stressed, or the user's autonomic nervous system changes rapidly.

Also, for example, when the amplitude 7270 is large, the monitoring server 3000 may determine that the user's feelings change rapidly, the user is highly stressed, or the user's autonomic nervous system changes rapidly.

According to an embodiment of the present application, the monitoring server 3000 can acquire the above-described parameters on the basis of the skin conductance data and can confirm a period of high stress or rapid changes in autonomic nervous system on the basis of the acquired parameters.

As an example, the monitoring server 3000 may calculate monitoring skin conductance with reference to the parameters that have been described in FIG. 34 when thyroid function monitoring is performed. A period that is used to calculate the monitoring skin conductance and a period in which stress is excessively high or an autonomic nervous system changes rapidly may not overlap each other.

The monitoring server may calculate SCFr, SCRm, SCRpl, SCRd, SCRpr, and/or SCRrr on the basis of the parameters that have been described in FIG. 34.

For example, SCFr may be an indicator of a period from the magnitude of the stimulus onset 7210 to the magnitude of the peak response 7250. Also, for example, SCRr may be an indicator related to the latency 7230.

Also, for example, SCRm may be an indicator related to the response onset or the response threshold 7240. Also, for example, SCRol may be an indicator related to the stimulus onset 7210.

Also, for example, SCRpl may be an indicator related to the response onset 7220. Also, SCRpl may be an indicator related to the stimulus onset 7210 or the peak response 7250. Also, for example, SCRd may be an indicator related to the response onset 7220 or the latency 7230.

Also, for example, SCRpr may be an indicator related to the peak response 7250 or the recovery time 7260. Also, for example, SCRrr may be an indicator related to the recovery time 7260 or the amplitude 7270.

According to an embodiment of the present application, the monitoring server 3000 may calculate SCFr, SCRm, SCRpl, SCRd, SCRpr, and/or SCRrr and perform thyroid function monitoring with reference to the calculated parameters.

As an example, the monitoring server 3000 may perform the thyroid function monitoring on the basis of the skin conductance data 7110 and may more accurately perform the thyroid function monitoring using the calculated SCFr, SCRm, SCRpl, SCRd, SCRpr, and/or SCRrr as secondary reference data.

In describing the skin conductance-related parameters so far, the monitoring server 3000 has been described as determining and calculating various indicators of skin conductance data. However, the present invention is not limited thereto, and the EDA calculation unit 5200 may serve as the monitoring server 3000.

Figure 35:
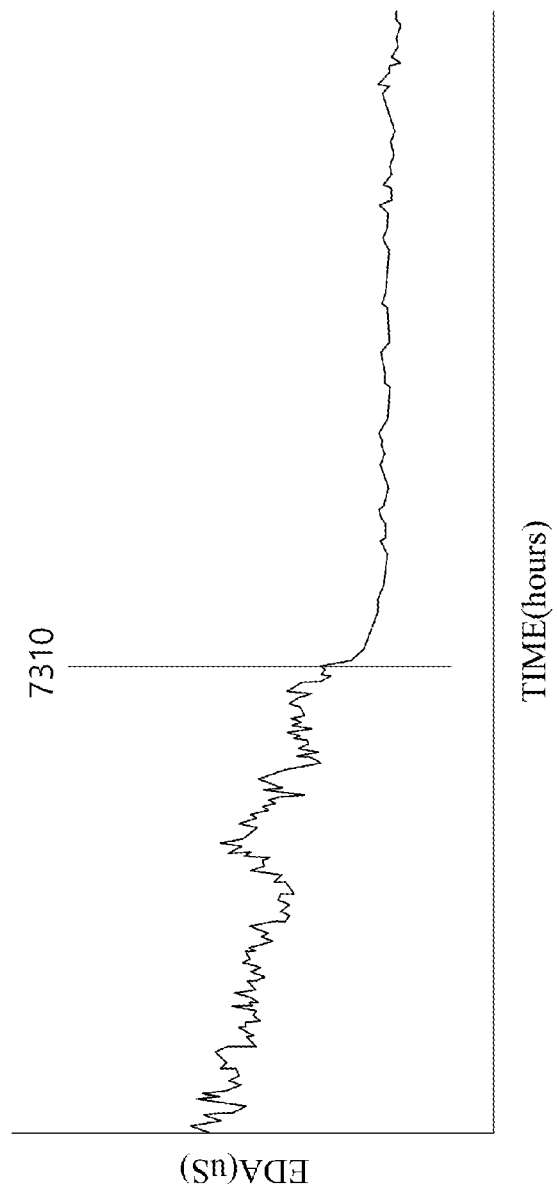
FIG. 35 is a diagram showing a skin conductance data graph according to an embodiment.

FIG. 35 is a diagram showing a skin conductance data graph according to an embodiment.

Through skin conductance data, the monitoring server 3000 may recognize the user's change in feelings, stress, or autonomic nervous system. Also, the skin conductance data may be used to determine whether a user has made a false statement. Also, the skin conductance data may be used to analyze a criminal's action or statement.

According to an embodiment, through the skin conductance data, the monitoring server 3000 may determine whether the user's thyroid function is abnormal.

For example, through a user's skin conductance data, the monitoring server 3000 may determine whether the user has hyperthyroidism or hypothyroidism. Also, for example, through a user's skin conductance data, the monitoring server 3000 may detect thyroid diseases such as thyroid cancer and thyroid inflammation through the user's skin conductance data.

For example, the function of the autonomic nervous system of a user suffering from hyperthyroidism may be excited. Also, the function of the autonomic nervous system of a user suffering from hypothyroidism may be reduced. In this case, when the excited state of the autonomic nervous system is determined through the skin conductance data, the monitoring server 3000 may determine whether the user has hyperthyroidism or hypothyroidism.

In detail, when the user's skin conductance data is greater than or equal to a predetermined value for a predetermined period (e.g., a monitoring period), the monitoring server 3000 may determine that the function of the user's autonomic nervous system is excessively excited compared to a normal person and thus may determine that the user suffers from hyperthyroidism.

Also, specifically, when the user's skin conductance data is less than or equal to a predetermined value for a predetermined period, the monitoring server 3000 may determine that the function of the user's autonomic nervous system is excessively reduced compared to a normal person and thus may determine that the user suffers from hypothyroidism.

A method of determining whether a user's thyroid function is abnormal using skin conductance data will be described in detail below.

When whether a user's thyroid function is abnormal is determined through skin conductance data, it is possible to determine the thyroid dysfunction in a non-invasive manner without a hormone test for the user.

Also, when whether a user's thyroid function is abnormal is determined through skin conductance data, it is possible to naturally determine the thyroid dysfunction in the user's daily life.

For example, a conventional test method (e.g., hormone test) for examining a user's thyroid function may affect the result by causing the user to be nervous, but the method for determining whether the thyroid function is abnormal according to the present invention can prevent the user from being nervous.

Referring to FIG. 35, skin conductance data may be distinguished with respect to a sleep start point 7310.

According to an embodiment, the sleep start point 7310 may be a time point determined by a user's input through a wearable device 1000. For example, the user may input information on a sleep start to the wearable device 1000, and the sleep start point 7310 may be a time point that is determined through the information.

According to another embodiment, the sleep start point 7310 may be a time point that is determined through determination by the wearable device 1000. For example, the sleep start point 7310 may be a time point that is determined through a plurality of sensors of the wearable device 1000 that can recognize the user's motion.

Specifically, the sleep start point 7310 may be determined by a period in which the number of steps extracted from a pedometer of the wearable device 1000 is less than or equal to a predetermined value. Also, specifically, the sleep start point 7310 may be determined by a period in which a GPS result of the wearable device 1000 is in a predetermined range.

Also, specifically, the sleep start point 7310 may be determined by a period in which a heart rate extracted from a heart rate monitor of the wearable device 1000 is less than or equal to a predetermined value. Also, specifically, the sleep start point 7310 may be determined by a period in which a result of a gyroscope of the wearable device 1000 is less than or equal to a predetermined value.

Also, specifically, the sleep start point 7310 may be determined by a user's sleep pattern determined through the wearable device 1000. For example, the sleep start point 7310 may be a time point at which the user's sleep pattern enters a non-waking period (e.g., REM, non-REM, SWS) from an awake period.

According to another embodiment, the sleep start point 7310 may be a time point at which the skin conductance data begins to decrease rapidly.

Specifically, the sleep start point 7310 may be a time point at which the skin conductance data begins to decrease by more than 1 μS.

Also, specifically, the sleep start point 7310 may be a time point at which a decreasing period 7440 begins. The decreasing period 7440 will be described in detail below.

The sleep start point 7310 is a time point at which a user can be regarded as entering a sleep period, and the present invention is not limited to the examples proposed herein.

Referring to FIG. 35, the aspect of skin conductance data may vary with respect to the sleep start point 7310.

For example, the change frequency of the skin conductance data before the sleep start point 7310 may be greater than the change frequency of the skin conductance data after the sleep start point 7310.

Also, for example, the average of the skin conductance data before the sleep start point 7310 may be greater than the average of the skin conductance data after the sleep start point 7310.

Also, for example, the maximum of the skin conductance data before the sleep start point 7310 may be greater than the maximum of the skin conductance data after the sleep start point 7310.

Also, for example, the minimum of the skin conductance data before the sleep start point 7310 may be greater than the minimum of the skin conductance data after the sleep start point 7310.

Figure 36:
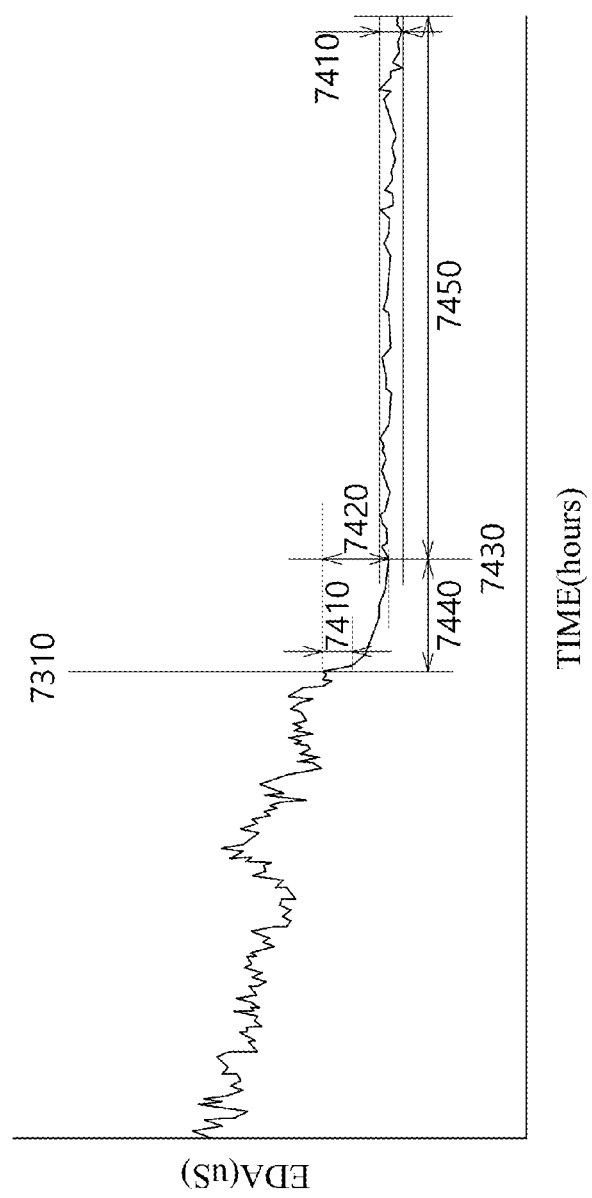
FIG. 36 is a diagram illustrating a resting period in a skin conductance data graph according to an embodiment.

FIG. 36 is a diagram illustrating a resting period in the skin conductance data graph according to an embodiment. Referring to FIG. 36, the skin conductance data after the sleep start point 7310 may be decreased compared to before the sleep start point 7310.

According to an embodiment, the skin conductance data after the sleep start point 7310 may include a decreasing period 7440 and a resting period 7450. In this case, the resting period 7450 may be a period that begins after the decreasing period 7440.

According to an embodiment, the resting period 7450 may be a period in which the fluctuation of the skin conductance data is within a predetermined range 7410. For example, the resting period 7450 may be a period in which the fluctuation of the skin conductance data is within a first range 7410.

For example, the size of the first range 7410 may be 3 μS. As a preferred example, the size of the first range 7410 may be 2 μS. As a preferred example, the size of the first range 7410 may be 1 μS. However, a different optimal value may be selected for the first range 7410 according to the characteristics of a user's skin, and thus the first range 7410 is not limited to the above-described numerical value.

The decreasing period 7440 may be a period in which the skin conductance data decreases beyond a second range after the sleep start point 7310. In this case, the second range may be greater than the first range. As an example, the second range may be 2 µS, and the first range 7410 may be 1 µS.

The decreasing period 7440 may be a period in which the skin conductance data decreases beyond the first range 7410 after the sleep start point 7310. For example, the decreasing period 7440 may be a period in which the skin conductance data decreases by more than 1 µS or 2 µS after the sleep start point 7310. However, the present invention is not limited thereto, and the decreasing period 7440 may be a period in which the skin conductance data decreases by more than another value.

Also, the decreasing period 7440 and the resting period 7450 may be distinguished by a resting period start point 7430.

According to an embodiment, the resting period start point 7430 may be an entry time point at which the skin conductance data begins to increase while the fluctuation of the skin conductance data is within the first range 7410. For example, the resting period start point 7430 may be the earliest time point in which the slope is positive while the fluctuation of the skin conductance data is within 1 µS.

In this case, a difference 7420 between the skin conductance data at the sleep start point 7310 and the skin conductance data at the resting period start point 7430 may be greater than the size of the first range 7410.

In this case, the calculated resting period 7450 may be determined as a user's true sleep period. Also, monitoring skin conductance may be calculated through the skin conductance data in the resting period 7450. The monitoring skin conductance may be determined according to the average, median, standard deviation, moving average, or the like of the skin conductance data in the resting period 7450. The monitoring server 3000 may compare the monitoring skin conductance and reference skin conductance to determine whether the user's thyroid function is abnormal.

According to an embodiment, the end point of the resting period 7450 may be a time point at which the fluctuation range of the skin conductance data becomes out of the first range. Alternatively, the end point of the resting period 7450 may be a time point at which the size of the skin conductance data becomes above or below a predetermined value.

Figure 37:
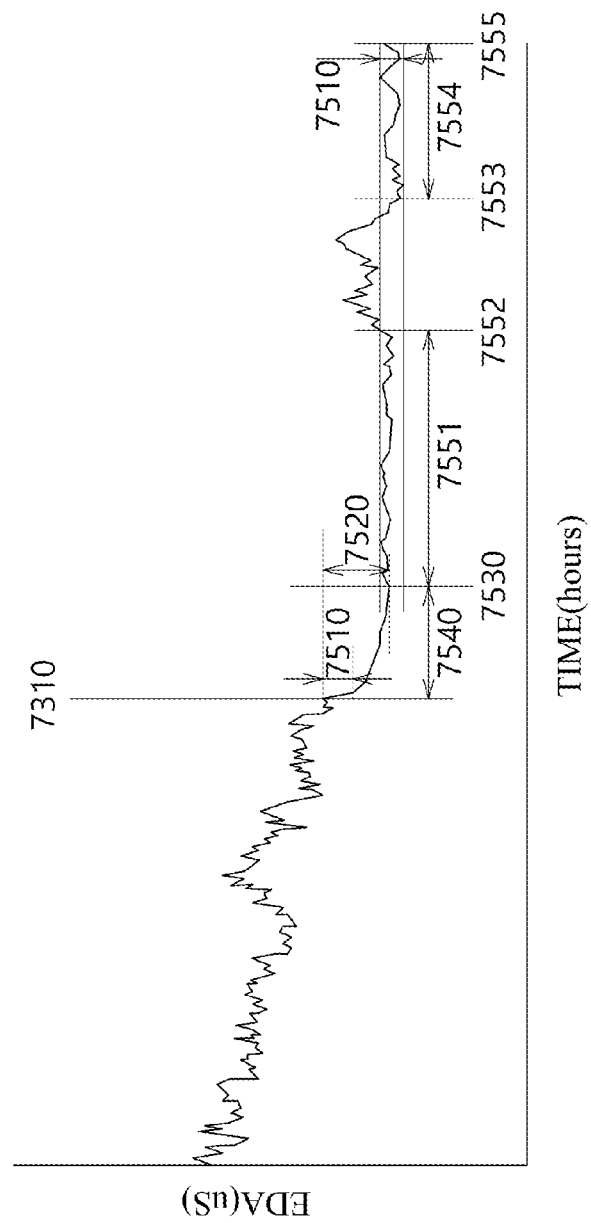
FIG. 37 is a diagram illustrating a resting period in a skin conductance data graph according to another embodiment.

FIG. 37 is a diagram illustrating a resting period in the skin conductance data graph according to an embodiment. Referring to FIG. 37, a plurality of resting periods 7551 and 7554 may be present after the sleep start point 7310. The monitoring server 3000 may confirm the plurality of resting periods 7551 and 7554 after the sleep start point 7310.

According to an embodiment, the skin conductance data after the sleep start point 7310 may include a decreasing period 7540, a first resting period 7551, and a second resting period 7554. In this case, the first resting period 7551 and the second resting period 7554 may be periods that begin after the decreasing period 7540.

According to an embodiment, the first resting period 7551 and the second resting period 7554 may be periods in which the fluctuation of the skin conductance data is within a predetermined range 7510.

For example, the first resting period 7551 and the second resting period 7554 may be periods in which the fluctuation of the skin conductance data is within a first range 7510. As a specific example, the size of the first range 7510 may be 1 µS or 2 µS. However, the present invention is not limited thereto, and the size of the first range 7510 may have other values.

The decreasing period 7540 may be a period in which the skin conductance data decreases beyond a second range after the sleep start point 7310. In this case, the second range may be greater than the first range. As an example, the second range may be 2 µS, and the first range 7510 may be 1 µS. The decreasing period 7540 may be a period in which the skin conductance data decreases beyond the first range 7510 after the sleep start point 7310. For example, the decreasing period 7540 may be a period in which the skin conductance data decreases by more than 1 µS or 2 µS after the sleep start point 7310. However, the present invention is not limited thereto, and the decreasing period 7440 may be a period in which the skin conductance data decreases by more than another value.

The first resting period 7551 may include a first resting period start point 7530 and a first resting period end point 7552. The monitoring server 3000 may distinguish the decreasing period 7540 and the first resting period 7551 on the basis of the first resting period start point 7530.

The second resting period 7554 may include a second resting period start point 7553 and a second resting period end point 7555. The monitoring server 3000 may not extract a period between the first resting period end point 7552 and the second resting period start point 7553 as a resting period.

According to an embodiment, the first resting period start point 7530 and the second resting period start point 7553 may be entry time points at which the skin conductance data begins to increase while the fluctuation of the skin conductance data is within the first range 7510.

For example, the first resting period start point 7530 and the second resting period start point 7553 may be the earliest time points at which the slope is positive while the fluctuation of the skin conductance data is within 2 µS.

In this case, a difference 7520 between the skin conductance data at the sleep start point 7310 and the skin conductance data at the first resting period start point 7530 and the second resting period start point 7553 may be greater than the size of the first range 7510.

According to an embodiment, the first resting period end point 7552 and the second resting period end point 7555 may be time points at which fluctuation of the skin conductance data deviates from the first range 7510. Alternatively, the first resting period end point 7552 and the second resting period end point 7555 may be time points at which the size of the skin conductance data becomes greater than or equal to a predetermined value.

In this case, the monitoring server 3000 may determine the calculated first resting period 7551 and second resting period 7554 as the user's true sleep periods. Also, through the skin conductance data in the plurality of resting periods 7551 and 7554, the monitoring server 3000 may determine whether the user's thyroid function is abnormal.

For example, through the average, median, standard deviation, or moving average of the skin conductance data in the plurality of resting periods 7551 and 7554, the monitoring server 3000 may determine whether the user's thyroid function is abnormal.

For example, the monitoring server 3000 may use the average of the skin conductance data of the entirety of the first resting period 7551 and the second resting period 7554 or may use the average of the first resting period 7551 and the average of the second resting period 7554.

Figure 38:
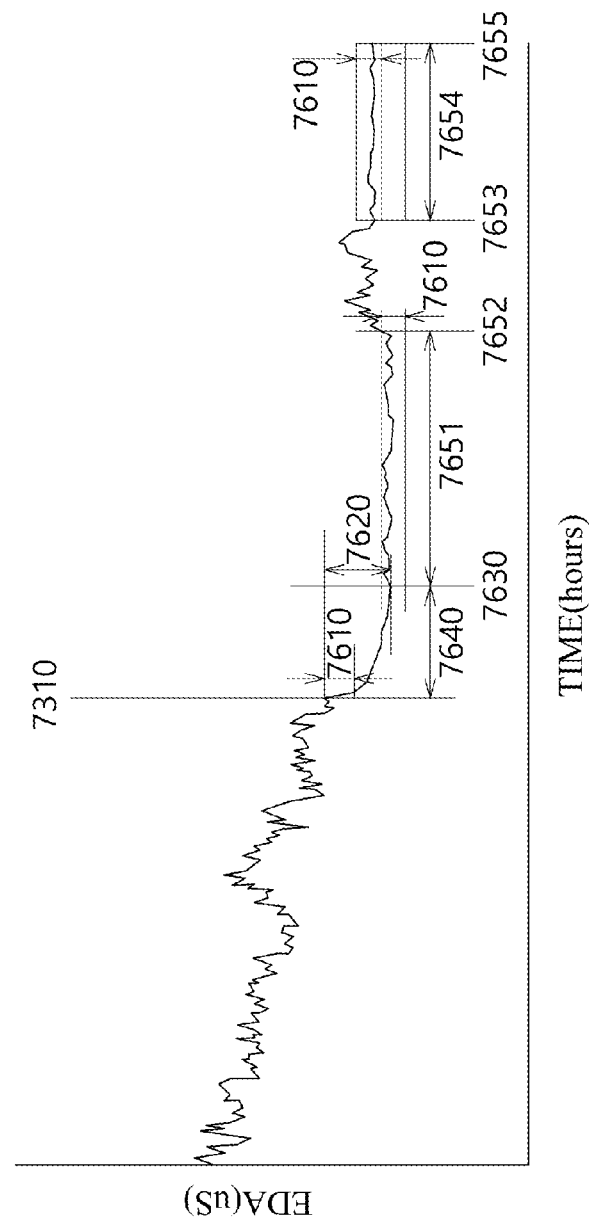
FIG. 38 is a diagram illustrating a resting period in a skin conductance data graph according to another embodiment.

FIG. 38 is a diagram illustrating a resting period in the skin conductance data graph according to another embodiment. Referring to FIG. 38, a plurality of resting periods 7651 and 7654 may be present after the sleep start point 7310.

A description of a decreasing period 7640 may overlap the description of the decreasing period 7540 of FIG. 37, and thus a detailed description thereof will be omitted.

Also, a description of a first resting period 7651 and a second resting period 7654 may overlap the description of the first resting period 7551 and the second resting period 7554 of FIG. 37, and thus a detailed description will be omitted.

Also, a description of a first range 7610 may overlap the description of the first range 7510 of FIG. 37, and thus a detailed description thereof will be omitted.

Also, a description of a first resting period start point 7630, a first resting period end point 7652, a second resting period start point 7653, and a second resting period end point 7655 may overlap the description of the first resting period start point 7530, the first resting period end point 7552, the second resting period start point 7553, and the second resting period end point 7555 of FIG. 37, and thus a detailed description thereof will be omitted.

According to an embodiment, the arithmetic operation value of the skin conductance data in the first resting period 7651 may be different from the arithmetic operation value of the skin conductance data in the second resting period 7654.

As an example, the maximum skin conductance of the first resting period 7651 may be smaller than the maximum skin conductance of the second resting period 7654. As another example, the minimum skin conductance of the first resting period 7651 may be smaller than the minimum skin conductance of the second resting period 7654. As another example, the average skin conductance of the first resting period 7651 may be smaller than the average skin conductance of the second resting period 7654.

Also, the present invention is not limited thereto, and a numerical value that may be calculated based on the skin conductance data in the first resting period 7651 may be different from a numerical value that may be calculated based on the skin conductance data in the second resting period 7654.

According to an embodiment, a numerical range of the skin conductance data in the first resting period 7651 may be different from a numerical range of the skin conductance data in the second resting period 7654.

As an example, the numerical range of the skin conductance data in the first resting period 7651 may not overlap the numerical range of the skin conductance data in the second resting period 7654. As another example, the numerical range of the skin conductance data in the first resting period 7651 may partially overlap the numerical range of the skin conductance data in the second resting period 7654.

As a specific example, the skin conductance data of the first resting period 7651 may have a numerical value of 1 µS or 2 µS. Also, the skin conductance data of the second resting period 7654 may have a numerical value of 2 µS or 3 µS.

In this case, the fluctuation of the first resting period 7651 and the fluctuation of the second resting period 7654 may be within a range of 1 µS, but the numerical range of the first resting period 7651 and the numerical range of the second resting period 7654 may be different from each other.

The monitoring server 3000 may determine the calculated first resting period 7651 and second resting period 7654 as the user's true sleep periods. Also, through the skin conductance data in the plurality of resting periods 7551 and 7554, the monitoring server 3000 may determine whether the user's thyroid function is abnormal.

Figure 39:
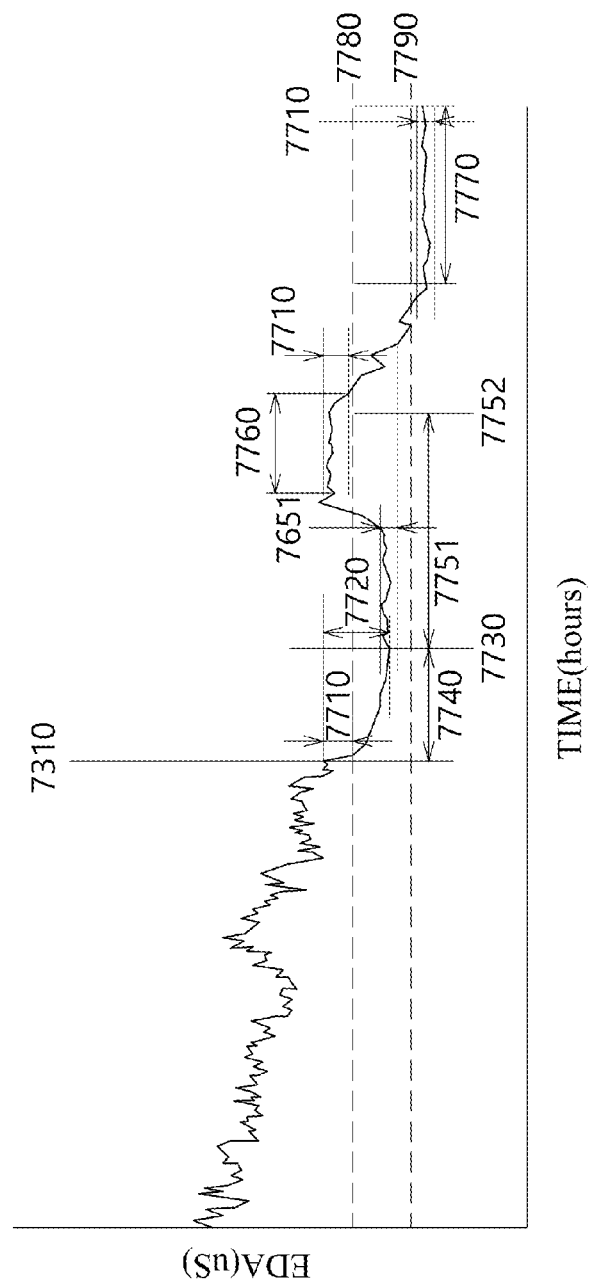
FIG. 39 is a diagram illustrating a resting period in a skin conductance data graph according to another embodiment.

FIG. 39 is a diagram illustrating a resting period in the skin conductance data graph according to another embodiment. A description of a decreasing period 7740 may overlap the description of the decreasing period 7440 of FIG. 36, and thus a detailed description thereof will be omitted.

Also, a description of a resting period 7751 may overlap the description of the resting period 7450 of FIG. 36, and thus a detailed description thereof will be omitted.

Also, a description of a first range 7710 may overlap the description of the first range 7410 of FIG. 36, and thus a detailed description thereof will be omitted.

Referring to FIG. 39, a resting period 7751 and a noise period 7760 may be present after the sleep start point 7310. For example, a first noise period 7760 and a second noise period 7770 may be present after the sleep start point 7310.

According to an embodiment, the fluctuation of the first noise period 7760 and the fluctuation of the second noise period 7770 may be within the first range 7710.

However, when determining whether a user's thyroid function is abnormal, the monitoring server 3000 may use the skin conductance data of the resting period 7751 and may not use the skin conductance data of the noise periods 7760 and 7770.

The skin conductance data of the noise periods 7760 and 7770 may be data to be removed when the monitoring server 3000 determines whether the user's thyroid function is abnormal because the noise periods may be difficult to consider as the user's true sleep period.

According to an embodiment, the fluctuation of the first noise period 7760 may be within the first range 7710 like the fluctuation of the resting period 7751, but a numerical range of the first noise period 7760 may be different from a numerical range of the resting period 7751.

In this case, the minimum of the first noise period 7760 may be greater than a first threshold 7780. Accordingly, when the fluctuation of skin conductance data of a predetermined period is within the first range 7710 and the minimum of the predetermined period is greater than or equal to the first threshold 7780, the predetermined period may be calculated as a noise period.

Also, in this case, the average of the first noise period 7760 may be greater than the first threshold 7780. Accordingly, when the fluctuation of skin conductance data of a predetermined period is within the first range 7710 and the average of the predetermined period is greater than or equal to the first threshold 7780, the predetermined period may be calculated as a noise period.

According to an embodiment, the fluctuation of the second noise period 7770 may be within the first range 7710 like the fluctuation of the resting period 7751, but a numerical range of the second noise period 7770 may be different from a numerical range of the resting period 7751.

In this case, the maximum of the second noise period 7770 may be smaller than a second threshold 7790. Accordingly, when the fluctuation of skin conductance data of a predetermined period is within the first range 7710 and the maximum of the predetermined period is less than or equal to the second threshold 7790, the predetermined period may be calculated as a noise period.

Also, in this case, the average of the second noise period 7770 may be smaller than the second threshold 7790. Accordingly, when the fluctuation of skin conductance data of a predetermined period is within the first range 7710 and the average of the predetermined period is less than or equal to the second threshold 7790, the predetermined period may be calculated as a noise period.

However, the present invention is not limited thereto, and when the fluctuation of skin conductance data of a predetermined period is within the first range 7710 and an absolute value of the predetermined period is a numerical value at which the predetermined period cannot be seen as the user's true sleep period, the predetermined period may be extracted as a noise period.

The skin conductance data of periods extracted as noise periods may be excluded from the resting period although the fluctuation is within the first range 7710.

When the monitoring server 3000 confirms a resting period for the calculation of monitoring skin conductance, the monitoring server 3000 may confirm, as a resting period, a period in which skin conductance fluctuates within the first range 7710 and which begins after a period in which skin conductance decreases beyond the first range 7710.

When an arithmetic operation value of a portion of the confirmed period deviates from a predetermined reference, the monitoring server 3000 may exclude the portion of the period from the resting period and may calculate the monitoring skin conductance on the basis of skin conductance data corresponding to the resting period.

Figure 40:
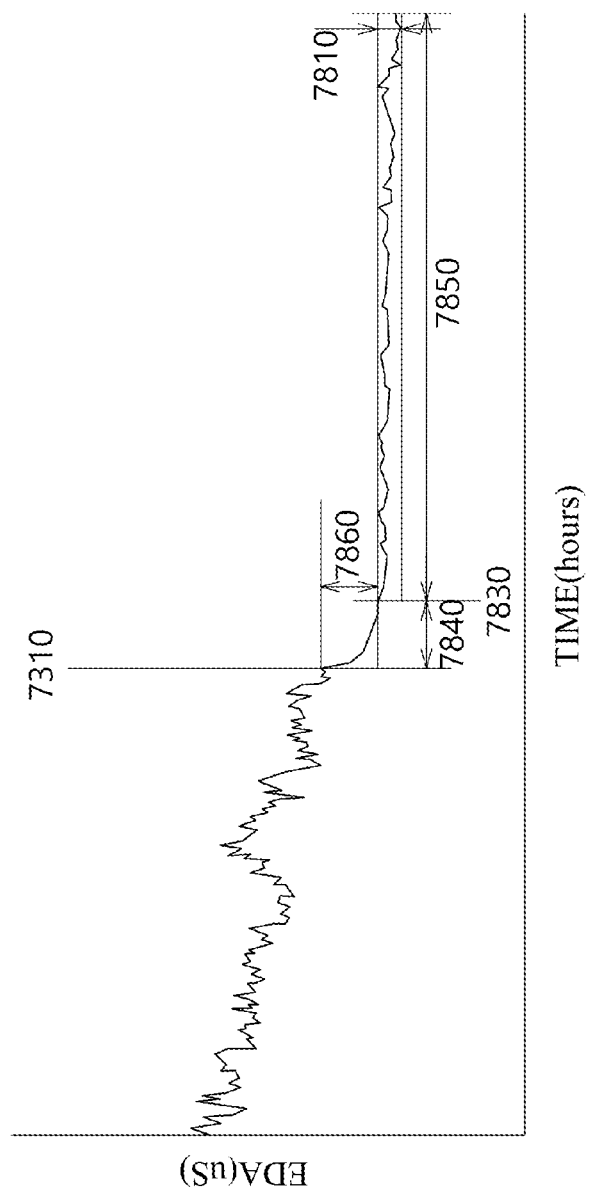
FIG. 40 is a diagram illustrating a resting period in a skin conductance data graph according to another embodiment.

FIG. 40 is a diagram illustrating a resting period in the skin conductance data graph according to another embodiment. A description of a decreasing period 7840 may overlap the description of the decreasing period 7440 of FIG. 36, and thus a detailed description thereof will be omitted.

Also, a description of a resting period 7850 may overlap the description of the resting period 7450 of FIG. 36, and thus a detailed description thereof will be omitted.

Also, a description of a first range 7810 may overlap the description of the first range 7410 of FIG. 36, and thus a detailed description thereof will be omitted.

Referring to FIG. 40, a decreasing period 7840 and a resting period 7850 may be present after the sleep start point 7310. The decreasing period 7840 and the resting period 7850 may be distinguished with respect to a resting period start point 7830.

Unlike the resting period start point 7430 of FIG. 36, the resting period start point 7830 of FIG. 40 may be defined by a different criterion.

According to an embodiment, the resting period start point 7830 may be the earliest time point in a predetermined period in which the fluctuation of the skin conductance data is within the first range 7810. In this case, the skin conductance data in the resting period start point 7830 may be less than or equal to a predetermined value.

In this case, a difference 7860 between the skin conductance data at the sleep start point 7310 and the skin conductance data at the resting period start point 7830 may be greater than the size of the first range 7810.

Also, the resting period 7850 may include a resting period end point, which is the latest time point, in the predetermined period. The skin conductance data at the resting period end point may have a value which is above or below a predetermined value and which is difficult to consider as a user's true sleep period.

Figure 41:
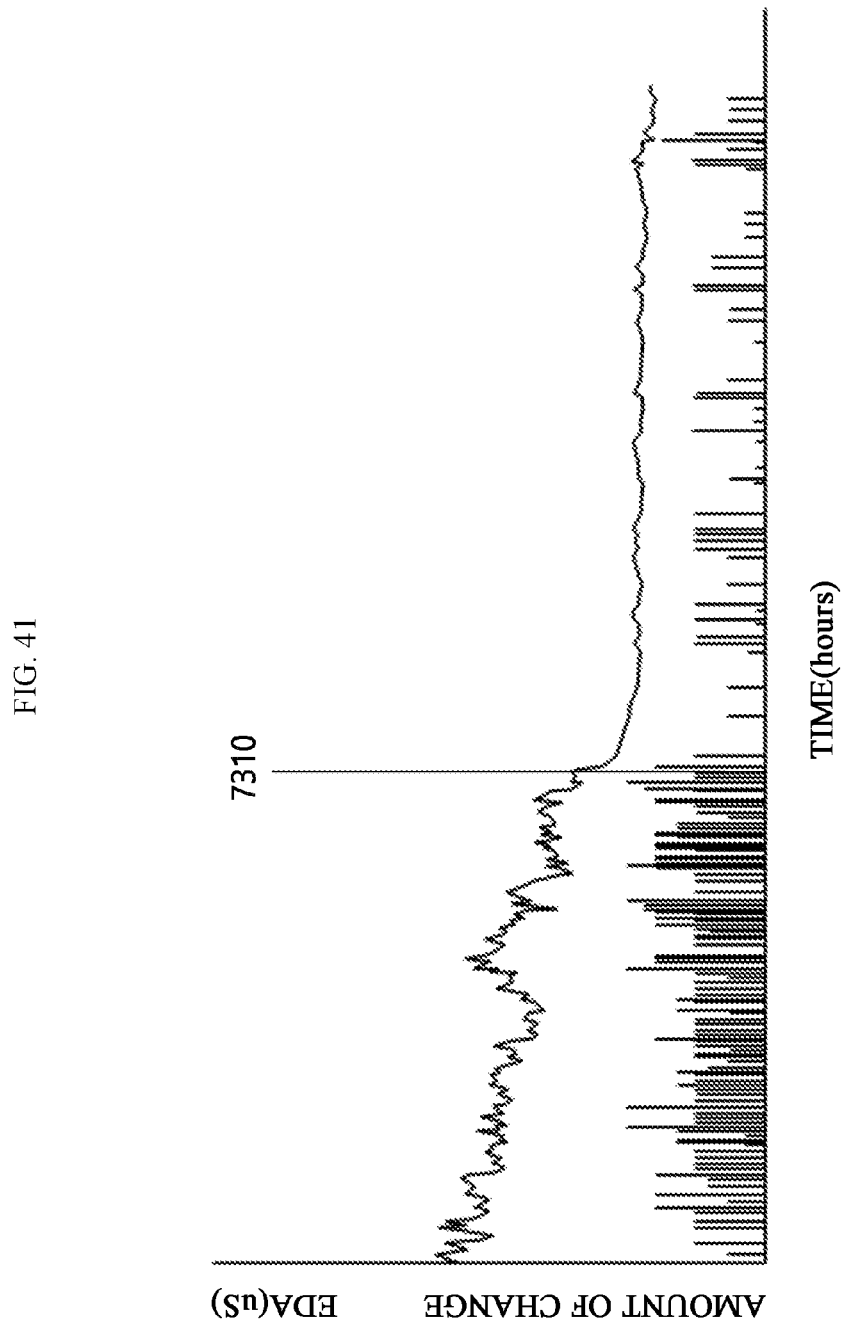
FIG. 41 is a diagram illustrating a resting period in a skin conductance data graph according to another embodiment.

FIG. 41 is a diagram illustrating a resting period in the skin conductance data graph according to another embodiment.

Referring to FIG. 41, the monitoring server 3000 may calculate the amount of change in skin conductance data through the skin conductance data.

According to an embodiment, the amount of change in skin conductance data may be obtained through the first-order differentiation of the skin conductance data. For example, the amount of change in skin conductance data may be obtained based on the slope of the skin conductance data.

The amount of change in skin conductance data may vary with respect to the sleep start point 7310. For example, the average of the amounts of change before the sleep start point 7310 may be greater than the average of the amounts of change after the sleep start point 7310.

According to an embodiment, a storm region of the skin conductance data may vary with respect to the sleep start point 7310. In this case, the storm region may be calculated based on the degree of change frequency of skin conductance data.

Also, in this case, the storm region may be a region with a high frequency. For example, the storm region may refer to a region having 4 to 10 peaks/min.

For example, the number of storm regions before the sleep start point 7310 may be greater than the number of storm regions after the sleep start point 7310. Also, for example, the frequency of the storm region before the sleep start point 7310 may be greater than the frequency of the storm region after the sleep start point 7310.

Also, for example, the average of peaks of the storm region before the sleep start point 7310 may be greater than the average of peaks of the storm region after the sleep start point 7310.

In this case, through the average of the amounts of data change, the frequency of data change, the number of storm regions, or the occurrence frequency of storm regions, the monitoring server 3000 may determine whether the user's thyroid function is abnormal.

For example, when the above parameters are greater than or equal to a predetermined value, the monitoring server 3000 may determine that the user is suffering from hyperthyroidism. Also, for example, when the above parameters are less than or equal to a predetermined value, the monitoring server 3000 may determine that the user is suffering from hypothyroidism.

According to an embodiment, the extraction of a resting period after the sleep start point 7310 may be related to the user's sleep pattern. In this case, the user's sleep pattern may be information obtained from an external device or the wearable device 1000.

For example, the user's sleep pattern may be obtained through polysomnography (PSG). Also, for example, the user's sleep pattern may be obtained by the sensing of a plurality of sensors (e.g., accelerometer, etc.) included in a smart watch.

In this case, the user's sleep pattern may be divided into REM, non-REM1 (N-REM1), non-REM2 (N-REM2), or Slow-wave sleep (SWS), but the present invention is not limited thereto.

For example, the REM period, the N-REM1 period, or a combination thereof in the user's sleep pattern may be extracted as a resting period, but the present invention is not limited thereto. The monitoring server 3000 may extract, as a resting period, a period in which it is determined that the user's sleep pattern is stable.

Also, for example, the probability of the storm region occurring in the N-REM2 period or the SWS period may be high. In this case, the monitoring server 3000 may exclude the N-REM2 period or the SWS period from the resting period. Alternatively, in this case, the monitoring server 3000 may reduce the ratio of the N-REM2 period or the SWS period to the resting period.

According to another embodiment, in the method of extracting a resting period, a user's sleep pattern may be considered in addition to skin conductance data.

For example, the monitoring server 3000 may primarily extract a resting period from skin conductance data after the sleep start point 7310 through the method described with reference to FIGS. 36 to 40.

Also, for example, the monitoring server 3000 may obtain information on the user's sleep pattern from an external device or the wearable device 1000. In this case, the information on the user's sleep pattern may be obtained through a motion sensor or a heart rate sensor of an external device or the wearable device 1000.

In this case, the monitoring server 3000 may secondarily extract a resting period by excluding a part in which the user's sleep pattern is in an SWS period and/or an N-REM2 period from the primarily extracted resting period.

Alternatively, in this case, the monitoring server 3000 may secondarily extract, as a resting period, parts in which the user's sleep pattern is an REM period from the primarily extracted resting period.

Accordingly, by setting the secondarily extracted resting period as a true resting period, the monitoring server 3000 may determine a user's thyroid dysfunction through skin conductance data in the resting period.

Figure 42:
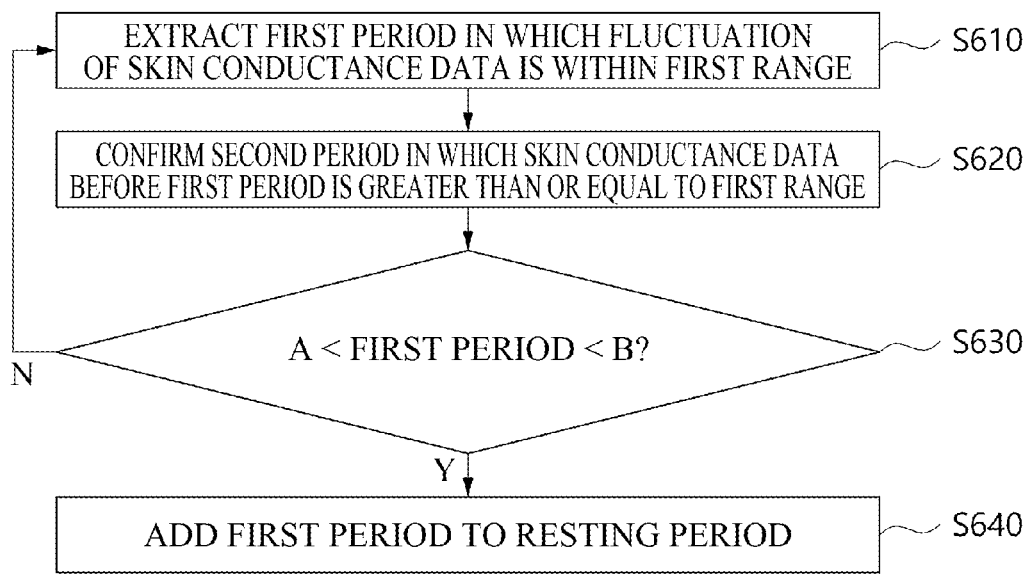
FIG. 42 is a diagram showing a flowchart of a resting period extraction method according to an embodiment.

FIG. 42 is a diagram showing a flowchart of a resting period extraction method according to an embodiment.

Referring to FIG. 42, the resting period extraction method according to an embodiment may include operations of extracting a first period (S610), confirming a second period (S620), comparing the size of the first period to a predetermined numerical value (S630), and adding the first period to a resting period (S640).

According to an embodiment, a monitoring server 3000 may perform the operation of extracting a first period (S610). In this case, the operation of extracting a first period (S610) may include an operation of extracting, as the first period, a period in which the fluctuation of skin conductance data is within a first range.

For example, the monitoring server 3000 may receive the skin conductance data from a wearable device 1000 or an EDA sensor 5000 to extract the first period.

According to another embodiment, an EDA calculation unit 5200 may receive the skin conductance data from an EDA measurement unit 5100 to extract the first period.

In this case, the difference between the maximum and the minimum of the extracted first period may be smaller than or equal to the size of the first range. For example, the difference between the maximum and the minimum of the first period may be 3 μS or less. Specifically, the difference between the maximum and the minimum of the first period may be 2 μS.

Also, in this case, a start point of the extracted first period may be the resting period start point 7430 described with reference to FIG. 36 or the resting period start point 7830 described with reference to FIG. 40.

According to another embodiment, the monitoring server 3000 or the EDA calculation unit 5200 may extract the first period using a phasic component 7130 of the skin conductance data.

For example, the first period may be a period in which the fluctuation or derivative of the phasic component 7130 is within the first range. Also, for example, the first period may be a period in which the maximum of the phasic component 7130 is less than or equal to a predetermined numerical value. Specifically, the first period may be a period in which the maximum of the phasic component 7130 is less than or equal to 2 μS.

According to an embodiment, the monitoring server 3000 or the EDA calculation unit 5200 may perform the operation of confirming a second period (S620). In this case, the operation of confirming a second period may include an operation of confirming a period in which skin conductance data before the first period decreases beyond the size of the first range.

In this case, the second period may be the decreasing period 7440 described with reference to FIG. 36. Also, in this case, a start point of the second period may be the sleep start point 7310 described with reference to FIG. 36.

Also, in this case, an end point of the second period may be the resting period start point 7430 described with reference to FIG. 36. Alternatively, the end point of the second period may be a time point before the resting period start point 7430 of FIG. 36.

Also, in this case, the difference in skin conductance data between the start point and the end point of the second period may be greater than or equal to the size of the first range.

According to an embodiment, the monitoring server 3000 or the EDA calculation unit 5200 may perform an operation of comparing numerical values of the first period. In this case, the operation of comparing the size of the first period and a predetermined numerical value (S630) may include an operation of checking whether the size of the first period is greater than a first value A and smaller than a second value B.

For example, operation S630 may include an operation in which the monitoring server 3000 or the EDA calculation unit 5200 checks whether the minimum of the first period is greater than the first value A. For example, operation S630 may include an operation in which the monitoring server 3000 or the EDA calculation unit 5200 checks whether the minimum of the first period is greater than the second value B.

According to another embodiment, the monitoring server 3000 or the EDA calculation unit 5200 may confirm the size of the first period using a tonic component 7120 of the skin conductance data.

For example, the monitoring server 3000 or the EDA calculation unit 5200 may check whether the minimum of the tonic component 7120 during the first period is greater than the first value A. Also, for example, the method may include an operation in which the monitoring server 3000 or the EDA calculation unit 5200 checks whether the maximum of the tonic component 7120 during the first period is smaller than the second value B.

Also, for example, the monitoring server 3000 or the EDA calculation unit 5200 may check whether the average of the tonic component 7120 during the first period may be between the first value A and the second value B.

When operation S630 is not performed, it may be impossible to extract the resting period from the user's true sleep period.

For example, when a user wakes up due to a hot external environment and is awake but does not move, the fluctuation in the first period may be within the first range, and the second period may be before the first period.

In this case, a numerical value of the first period may be greater than the second value B. In this case, the user is awake rather than asleep, and thus this period may have to be excluded from the resting period.

Also, for example, similarly, when a user wakes up due to a cold external environment and is awake but does not move, a numerical value of the first period may be smaller than the first value A. Even in this case, the user is awake, and thus this period may have to be excluded from the resting period.

Operation S640 may be performed when the numerical value of the first period falls within a predetermined numerical range, and operation S610, which is for extracting a new first period, may be performed when the numerical value does not fall within the predetermined numerical range.

According to an embodiment, the monitoring server 3000 may add the first period confirmed through operations S610 to S630 to the resting period.

After the operation of adding the first period to the resting period, an operation of checking whether the user's thyroid function is abnormal may be performed through the skin conductance data in the resting period.

According to an embodiment, the user's thyroid function may be monitored through the skin conductance data. In this case, the thyroid function monitoring method of FIG. 5 may be followed.

According to an embodiment, when skin conductance information is acquired through the EDA sensor 5000 (S1100), monitoring data may be calculated (S1300), and whether the user's thyroid function is abnormal may be determined (S1500).

The wearable device 1000 may acquire the user's skin conductance information. The wearable device 1000 may acquire skin conductance information of a user who wears the wearable device 1000. In this case, the acquisition of the skin conductance information may be performed at predetermined intervals.

For example, the device sensor unit 1400 of the wearable device 1000 may include the EDA sensor 5000, and the user's skin conductance information may be acquired using the EDA sensor 5000 at first intervals.

Also, for example, the device sensor unit 1400 of the wearable device 1000 may include a motion sensor, and the user's motion information may be acquired using the motion sensor at second intervals.

In this case, the first period and the second period may be the same or different from each other.

The wearable device 1000 may transmit the user's skin conductance information to a user terminal 2000. For example, as soon as the user's skin conductance information is acquired, the wearable device 1000 may transmit the acquired skin conductance information to the user terminal 2000.

Also, for example, the wearable device 1000 may transmit the user's acquired set of skin conductance information to the user terminal 2000 at predetermined intervals. In this case, the interval at which the wearable device 1000 acquires the user's skin conductance information may be shorter than the interval at which the wearable device 1000 transmits the user's skin conductance information.

The wearable device 1000 may transmit one or more kinds of biometric information of the user to the user terminal 2000. As an example, the biometric information transmitted to the user terminal 2000 may be skin conductance information. As another example, the biometric information transmitted to the user terminal 2000 may be skin conductance information and motion information.

The biometric information transmitted by the wearable device 1000 may be associated with other information. As an example, the biometric information transmitted by the wearable device 1000 may be skin conductance information associated with time.

As another example, the biometric information transmitted by the wearable device 1000 may be skin conductance information associated with time and motion information associated with time. As another example, the biometric information transmitted by the wearable device 1000 may be in a form in which time, skin conductance information, and motion information are associated with each other.

According to an embodiment, the monitoring server 3000 may calculate the monitoring data of FIG. 5 on the basis of the acquired skin conductance information (S1300).

Specifically, when calculating the monitoring data, the monitoring server 3000 may follow the monitoring data calculation method S1300 of FIG. 6.

The monitoring server 3000 may confirm a resting period (S1310). For example, the resting period may include some time points after the sleep start point 7310 of FIG. 35.

Here, a method for resting period confirmation S1310 may be replaced with the resting period calculation method described with reference to FIG. 42.

For example, the predetermined criterion of S1310 may include the conditions of operations S610 to S630 of FIG. 42.

Specifically, the predetermined criterion may include whether the fluctuation of skin conductance data in one period is within the first range. Also, the predetermined criterion may include whether there is a second period in which skin conductance data before one period decreases beyond the first range. Also, the predetermined criterion may include whether the size of one period may be greater than or equal to a first value and smaller than or equal to a second value.

Therefore, a redundant description of a specific operation to be performed in the operation during the resting period confirmation S1310 will be omitted.

According to an embodiment, the monitoring server 3000 may extract skin conductance information corresponding to the resting period (S1330).

For example, the monitoring server 3000 may extract skin conductance information corresponding to one or more confirmed resting periods (S1330). Also, for example, the monitoring server 3000 may extract skin conductance information corresponding to one or more confirmed resting periods included in the monitoring period (S1330).

According to an embodiment, the monitoring server 3000 may calculate monitoring data (S1350). In this case, the monitoring server 3000 may calculate monitoring data on the basis of the extracted skin conductance information (S1350).

In this case, the extracted skin conductance information may be extracted based on the skin conductance data in the resting period of FIGS. 35 to 41.

For example, the monitoring server 3000 may calculate, as the monitoring data, the average of the plurality of pieces of skin conductance data corresponding to the plurality of confirmed resting periods included in the monitoring period.

Also, for example, the monitoring server 3000 may calculate, as the monitoring data, the median of the medians of the plurality of pieces of skin conductance data corresponding to the plurality of resting periods included in the monitoring period.

Also, for example, the monitoring server 3000 may exclude the maximum and the minimum from the plurality of pieces of skin conductance data corresponding to the plurality of resting periods included in the monitoring period and calculate, as the monitoring data, an arithmetic operation value of the remaining skin conductance data.

According to an embodiment, the monitoring server 3000 may use reference data on the basis of the skin conductance data when determining the user's thyroid dysfunction. A basic description of the reference data may overlap that of FIG. 7, and thus a detailed description thereof will be omitted. In this case, the reference data calculation method of FIG. 7 may be followed.

The monitoring server 3000 may receive thyroid state information from the user terminal 2000 (S2100). According to an embodiment, the user terminal 2000 may receive a user's thyroid state information through a terminal input unit 2100.

In this case, the thyroid state information may be information regarding a thyroid hormone level acquired through the user's blood test or the like. Alternatively, the thyroid state information may be information regarding a thyroid state acquired through a questionnaire about the user's symptoms.

The user terminal 2000 may transmit the received thyroid state information to the monitoring server 3000. The monitoring server 3000 may calculate reference data (S2300) when the thyroid state information is received (S2100).

The reference data calculation period may be a period in which the user's thyroid function corresponds to "normal" according to the thyroid state information.

For example, when the received thyroid state information corresponds to a normal range, a predetermined period before and after the thyroid state information is input may be determined as the reference data calculation period.

A detailed description of the thyroid state information may overlap that of FIG. 7, and thus a detailed description thereof will be omitted.

According to an embodiment, the user's thyroid dysfunction may be determined through the reference data. In this case, the reference data calculation method of FIG. 8 may be followed.

The monitoring server 3000 may determine a reference data calculation period (S2310). A description of the reference data calculation period may overlap that of FIG. 8, and thus a detailed description thereof will be omitted.

The monitoring server 3000 may confirm a resting period corresponding to the determined reference data calculation period (S2320).

Here, a method for resting period confirmation S2320 may be replaced with the resting period calculation method described with reference to FIG. 42. Therefore, a redundant description of a specific operation to be performed in the resting period confirmation S2320 will be omitted.

According to an embodiment, the monitoring server 3000 may extract skin conductance information corresponding to the resting period (S2330).

For example, the monitoring server 3000 may extract skin conductance information corresponding to one or more confirmed resting periods (S2330). Also, for example, the monitoring server 3000 may extract skin conductance information corresponding to one or more confirmed resting periods included in the monitoring period (S2330).

According to an embodiment, the monitoring server 3000 may calculate reference data (S2360). In this case, the monitoring server 3000 may calculate the reference data on the basis of the extracted skin conductance information (S2360).

In this case, the extracted skin conductance information may be extracted based on the skin conductance data in the resting period of FIGS. 35 to 41.

For example, the monitoring server 3000 may calculate, as the reference data, the average of the plurality of pieces of skin conductance data corresponding to the plurality of confirmed resting periods included in the monitoring period.

Also, for example, the monitoring server 3000 may calculate, as the reference data, the median of the medians of the plurality of pieces of skin conductance data corresponding to the plurality of resting periods included in the monitoring period.

Also, for example, the monitoring server 3000 may exclude the maximum and the minimum from the plurality of pieces of skin conductance data corresponding to the plurality of resting periods included in the monitoring period and calculate, as the reference data, an arithmetic operation value of the remaining skin conductance data.

According to an embodiment, when the monitoring server 3000 receives thyroid state information outside a normal range, the reference data may be calculated according to the reference data calculation method of FIG. 9.

When the monitoring server 3000 receives thyroid state information outside a normal range, a basic description of the reference data calculation method may overlap that of FIG. 9, and thus a detailed description thereof will be omitted.

The monitoring server 3000 may calculate reference data by correcting the reference period data on the basis of the received thyroid state information (S2350).

For example, the monitoring server 3000 may compute by which ng/dL the user's hormone level corresponding to the received thyroid state information should be increased or decreased in order to match the hormone level to a normal range and may estimate the amount of change in skin conductance corresponding to the increase or the decrease.

In this case, the monitoring server 3000 may calculate the reference data by adding or subtracting the estimated amount of change in skin conductance to or from the reference period data (S2350). The monitoring server 3000 may store data necessary to correct the reference period data.

For example, data on the correlations between skin conductance data and hormone levels of multiple users may be stored in the monitoring server 3000.

Specifically, statistical data on how many µS skin conductance data increases by roughly when the hormone level increases by 0.1 ng/dL may be stored in the monitoring server 3000.

According to an embodiment, the monitoring server 3000 may determine a user's thyroid dysfunction (S1500) by comparing the reference data and the monitoring data calculated through the skin conductance data (1510).

A description of a method of determining the user's thyroid dysfunction (S1500) may overlap that of FIG. 10, and thus a detailed description thereof will be omitted.

According to an embodiment, the monitoring server 3000 may compare the monitoring data and the reference data. A description of a comparison algorithm may overlap that of FIG. 11, and thus a detailed description thereof will be omitted.

Figure 43:
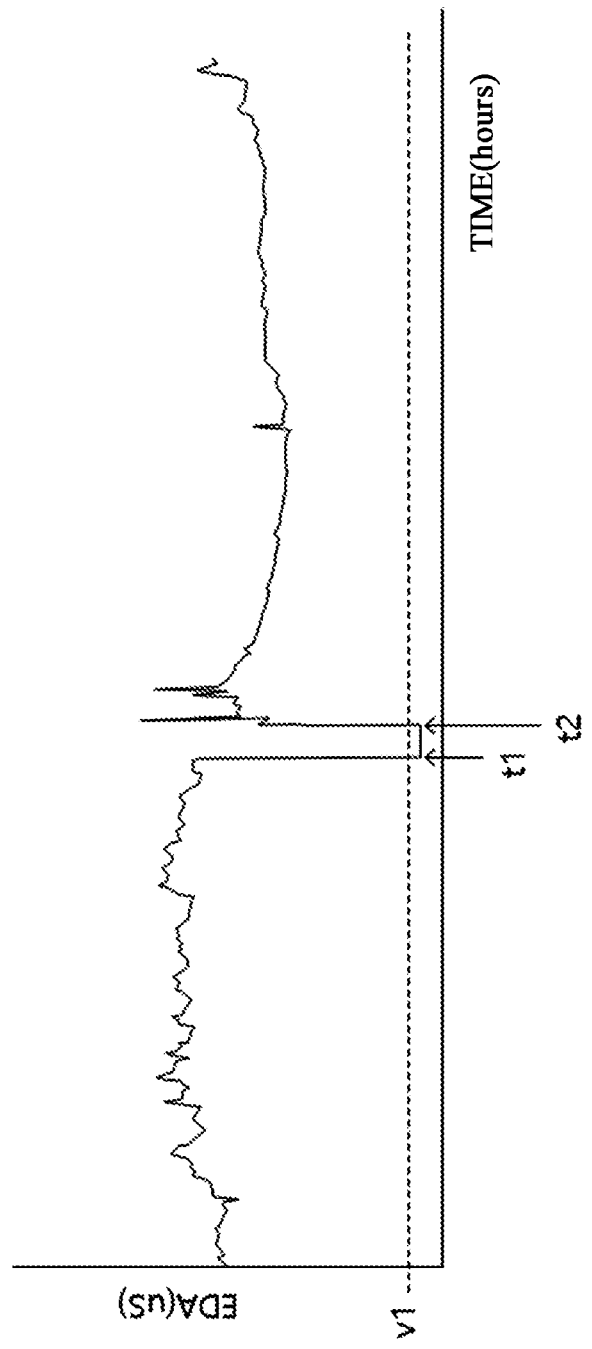
FIG. 43 is a diagram showing a skin conductance data graph corresponding to a wearable device wearing state according to an embodiment.

FIG. 43 is a diagram showing a skin conductance data graph corresponding to a wearing state for a wearable device 1000 according to an embodiment.

Referring to FIG. 43, the skin conductance data may vary depending on the user's wearing state for the wearable device 1000. Through the skin conductance data, the monitoring server 3000 may check or determine whether the user wears the wearable device 1000 or whether the wearable device 1000 is properly worn.

For example, skin conductance data when the user wears the wearable device 1000 and skin conductance data when the user does not wear the wearable device 1000 may have different aspects.

Also, for example, while the user wears the wearable device 1000, skin conductance data when the wearable device 1000 is properly worn and skin conductance data when the wearable device 1000 is not properly won (e.g., an EDA measurement electrode is not in contact with skin) may have different aspects.

Referring to FIG. 43, between a first time point t1 and a second time point t2, the user may not wear the wearable device 1000. Alternatively, between the first time point t1 and the second time point t2, the user wears the wearable device 1000, but the wearable device 1000 may not be properly worn.

For example, the first time point t1 may be a time point at which the user takes off the wearable device 1000, and the second time point t2 may be a time point at which the user puts on the wearable device 1000 again.

In this case, when the user takes off the wearable device 1000, skin conductance data may not be acquired during the non-wearing period.

Also, for example, while an EDA electrode is in contact with the user's skin, the first time point t1 may be a time point at which the EDA electrode is separated from the skin. Also, for example, while an EDA electrode is not in contact with the user's skin, the second time point t2 may be a time point at which the EDA electrode is brought into contact with the skin.

Also, for example, the first time point t1 may be a time point at which the moving average of the skin conductance data decreases rapidly (e.g., by a predetermined numerical value), and the second time point t2 may be a time point at which the moving average of the skin conductance data increases rapidly after the first time point t1.

According to an embodiment, the skin conductance data between the first time point t1 and the second time point t2 may be less than or equal to a predetermined value v1. For example, the skin conductance data between the first time point t1 and the second time point t2 may be less than or equal to 0.01 uS or less than or equal to 0.

According to another embodiment, the fluctuation of the skin conductance data between the first time point t1 and the second time point t2 may be less than or equal to a predetermined numerical value. For example, the slope or derivative of the skin conductance data between the first time point t1 and the second time point t2 may be less than or equal to a predetermined numerical value.

Also, for example, the fluctuation of the skin conductance data between the first time point t1 and the second time point t2 may be smaller than the fluctuation of the skin conductance data before the first time point t1 and/or after the second time point t2.

According to another embodiment, the average or median of the skin conductance data between the first time point t1 and the second time point t2 may be smaller than the average or median of the skin conductance data before the first time point t1 and/or after the second time point t2 by a predetermined value.

According to another embodiment, the average or median of the skin conductance data between the first time point t1 and the second time point t2 may be smaller than the average or median of the skin conductance data in the resting period.

Specifically, the average or median of the skin conductance data between the first time point t1 and the second time point t2 may be different from the average or median of the skin conductance data in the resting period by a value of 2 to 5 µS.

Also, the average or median of the skin conductance data between the first time point t1 and the second time point t2 may be within 1 µS.

In this case, the monitoring server 3000 may perform an operation of calculating the average or median of the skin conductance data between the first time point t1 and the second time point t2 and comparing the calculated average or median to the average or median of the skin conductance data in the resting period.

In this case, when a value of the skin conductance data between the first time point t1 and the second time point t2 is smaller than a value of the skin conductance data in the resting period and is less than or equal to a predetermined numerical value (e.g., 1 µS, 0.1 µS, or 0.01 µS), the period between the first time point t1 and the second time point t2 may be determined as being in a state where the wearable device 1000 is not worn or is not properly worn.

According to an embodiment, before performing the operation of extracting the first period (S610) of FIG. 42, an operation of determining whether the wearable device 1000 is worn or whether the wearable device 1000 is properly worn may be performed.

For example, before performing the operation of extracting the first period (S610), the monitoring server 3000 may determine whether the wearable device 1000 is worn or whether the wearable device 1000 is properly worn.

When the wearable device 1000 is worn or when the wearable device 1000 is properly worn, operations S610 to S640 may be performed. However, when the wearable device 1000 is not worn or when the wearable device 1000 is not properly worn, operation S610 may not be performed.

While the elements and features of the present application have been described with reference to embodiments of the present application, the present application is not limited thereto. It will be obvious to those skilled in the art that various changes or modifications may be made therein without departing from the spirit and scope of the present application. Accordingly, such changes or modifications are intended to fall within the scope of the appended claims.

What is claimed is:

1. A method for treatment for thyroid abnormality, the method comprising:
   obtaining a medication prescription date of a patient diagnosed for hyperthyroidism, wherein the medication prescription date is a prescription date of a hyperthyroidism medication prescribed for the patient;
   obtaining a specific date;
   receiving heart rate measurements of the patient obtained by a wearable device for an extended period comprising a plurality of days during which the patient is supposed to take the hyperthyroidism medication; computing a heart rate index of the patient for the specific date using one or more of the heart rate measurements, wherein the heart rate index is used to monitor hypothyroidism for the patient or both of hypothyroidism and hyperthyroidism for the patient;
   for the specific date, determining whether a predetermined period has passed from the prescription date;
   if it is determined that the predetermined period has passed from the prescription date to the specific date, generating a hypothyroidism alert if the heart rate index is smaller than a first reference value associated with hypothyroidism, and
   generating a hyperthyroidism alert if the heart rate index is greater than a second reference value associated with hyperthyroidism; or
   if it is determined that the predetermined period has not passed from the prescription date to the specific date, generating the hypothyroidism alert if the heart rate index is smaller than the first reference value associated with hypothyroidism, while the hyperthyroidism alert does not generate even if the heart rate index is greater than the second reference value associated with hyperthyroidism; and conducting a blood test on the patient in reply to the hypothyroidism alert or taking the hyperthyroidism medication in adjusted doses by being re-prescribed in reply to the hypothyroidism alert, wherein the heart rate index is a personalized index reflecting attributes of the patient diagnosed for hyperthyroidism, wherein the predetermined period is not set based on attributes of the patient diagnosed for hyperthyroidism, and is set based on a type of the hyperthyroidism medication prescribed for the patient, and wherein as the first reference value is smaller than the second reference value, the hypothyroidism alert and the hyperthyroidism alert are not generated simultaneously.

2. The method of claim 1, further comprising:
receiving drug taking information of the patient; and
classifying the patient into a hyperthyroidism treatment group based on the drug taking information.

3. The method of claim 1, further comprising:
receiving the heart rate measurements of the patient for the extended period comprising the plurality of days during which the patient is supposed to take the hyperthyroidism medication; and
computing the heart rate index of the patient for the specific date using one or more of the heart rate measurements; and
wherein the heart rate measurements comprise resting heart rates, wherein the heart rate index is computed based on the resting heart rates.

4. The method of claim 1,
wherein the hypothyroidism alert is generated if the heart rate index is smaller than the first reference value associated with hypothyroidism compared to a reference heart rate,
wherein the hyperthyroidism alert is generated if the heart rate index is greater than the second reference value associated with hyperthyroidism compared to the reference heart rate, and
wherein the reference heart rate is calculated based on a thyroid hormone level of the patient measured by a blood test and a heart rate of the patient, or is calculated based on heart rates of the patient for a plurality of consecutive days.

5. The method of claim 4, further comprising calculating the reference heart rate, wherein the heart rate measurements comprise resting heart rates,
wherein calculating the reference heart rate comprises:
confirming, if the thyroid hormone level is received, the thyroid hormone level is within a normal range; and
computing, if the thyroid hormone level is in the normal range, the reference heart rate based on the resting heart rates of the plurality of consecutive days including a first test day of the thyroid hormone level.

6. The method of claim 5,
wherein calculating the reference heart rate further comprises:
if the thyroid hormone level is not in the normal range, calculating a current heart rate based on the resting heart rates of the plurality of consecutive days including a second test day of the thyroid hormone level; and
estimating the reference heart rate, when the patient's thyroid function is normal, based on the thyroid hormone level and the current heart rate.

7. The method of claim 1, wherein receiving the heat rate measurements is less frequently than measuring of the heart rate measurements.

8. The method of claim 1, further comprising transmitting a signal to an external device for outputting the hypothyroidism alert or hyperthyroidism alert on a display unit of the external device.

9. The method of claim 1, wherein the predetermined period has passed from the prescription date to the specific date, the heart rate index is smaller than the first reference value associated with hypothyroidism, and the method comprises generating the hypothyroidism alert.

10. The method of claim 1, wherein the predetermined period has passed from the prescription date to the specific date, the heart rate index is greater than the second reference value associated with hyperthyroidism, and the method comprises generating the hyperthyroidism alert.

11. The method of claim 1, wherein the predetermined period has not passed from the prescription date to the specific date, the heart rate index is smaller than the first reference value associated with hypothyroidism, and the method comprises generating the hypothyroidism alert.

12. The method of claim 11, wherein the heart rate index is greater than the second reference value associated with hyperthyroidism, and the hyperthyroidism alert does not generate.

13. A server comprising a communication unit, an input unit, an output unit, at least one processing unit, wherein the server is configured to:
obtain a medication prescription date of a patient diagnosed for hyperthyroidism, wherein the medication prescription date is a prescription date of a hyperthyroidism medication prescribed for the patient,
obtain a specific date,
receive, through the communication unit, heart rate measurements of the hyperthyroidism patient for an extended period comprising a plurality of days during which the hyperthyroidism patient is supposed to take the hyperthyroidism medication,
compute a heart rate index of the patient for the specific date using one or more of the heart rate measurements, wherein the heart rate index is used to monitor hypothyroidism for the patient or both of hypothyroidism and hyperthyroidism for the patient,
for the specific date, determine whether a predetermined period has passed from the prescription date,
if it is determined that the predetermined period has passed from the prescription date to the specific date,
generate a hypothyroidism alert if the heart rate index is smaller than a first reference value associated with hypothyroidism, and
generate a hyperthyroidism alert if the heart rate index is greater than a second reference value associated with hyperthyroidism, or
if it is determined that the predetermined period has not passed from the prescription date to the specific date,
generate the hypothyroidism alert if the heart rate index is smaller than the first reference value associated with hypothyroidism, while the hyperthyroidism alert does not generate even if the heart rate index is greater than the second reference value associated with hyperthyroidism,
inducing to conduct a blood test on the patient in reply to the hypothyroidism alert or take the hyperthyroidism medication in adjusted doses by being re-prescribed in reply to the hypothyroidism alert, wherein the heart rate index is a personalized index reflecting attributes of the patient diagnosed for hyperthyroidism, wherein the predetermined period is not set based on the attributes of the patient diagnosed for hyperthyroidism, and is set based on a type of the hyperthyroidism medication prescribed for the patient, wherein as the first reference value is smaller than the second reference value, the hypothyroidism alert and the hyperthyroidism alert are not generated simultaneously.

14. A user terminal comprising a communication unit, an input unit, an output unit, at least one processing unit, wherein the user terminal is configured to:

obtain a medication prescription date of a patient diagnosed for hyperthyroidism, wherein the medication prescription date is a prescription date of a hyperthyroidism medication prescribed for the patient, obtain a specific date, receive, through the communication unit, heart rate measurements of the hyperthyroidism patient for an extended period comprising a plurality of days during which the hyperthyroidism patient is supposed to take the hyperthyroidism medication, compute a heart rate index of the patient for the specific date using one or more of the heart rate measurements, wherein the heart rate index is used to monitor hypothyroidism for the patient or both of hypothyroidism and hyperthyroidism for the patient, for the specific date, determine whether a predetermined period has passed from the prescription date, if it is determined that the predetermined period has passed from the prescription date to the specific date,
generate a hypothyroidism alert if the heart rate index is smaller than a first reference value associated with hypothyroidism, and generate a hyperthyroidism alert if the heart rate index is greater than a second reference value associated with hyperthyroidism, or if it is determined that the predetermined period has not passed from the prescription date to the specific date,
generate the hypothyroidism alert if the heart rate index is smaller than the first reference value associated with hypothyroidism, while the hyperthyroidism alert does not generated even if the heart rate index is greater than the second reference value associated with hyperthyroidism, inducing to conduct a blood test on the patient in reply to the hypothyroidism alert or take the hyperthyroidism medication in adjusted doses by being re-prescribed in reply to the hypothyroidism alert, wherein the heart rate index is a personalized index reflecting attributes of the patient diagnosed for hyperthyroidism, wherein the predetermined period is not set based on the attributes of the patient diagnosed for hyperthyroidism, and is set based on a type of the hyperthyroidism medication prescribed for the patient, wherein as the first reference value is smaller than the second reference value, the hypothyroidism alert and the hyperthyroidism alert are not generated simultaneously.

* * * * *